(12) United States Patent
Lee et al.

(10) Patent No.: US 12,077,699 B2
(45) Date of Patent: Sep. 3, 2024

(54) DOPANT FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Sangshin Lee, Suwon-si (KR); Mounggon Kim, Suwon-si (KR); Eun Sun Yu, Suwon-si (KR); Jun Yeob Lee, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 363 days.

(21) Appl. No.: 15/573,977

(22) PCT Filed: Oct. 26, 2015

(86) PCT No.: PCT/KR2015/011321
§ 371 (c)(1),
(2) Date: Nov. 14, 2017

(87) PCT Pub. No.: WO2016/186269
PCT Pub. Date: Nov. 24, 2016

(65) Prior Publication Data
US 2018/0291264 A1 Oct. 11, 2018

(30) Foreign Application Priority Data

May 15, 2015 (KR) .......................... 10-2015-0068121

(51) Int. Cl.
*C07D 209/62* (2006.01)
*C07D 265/38* (2006.01)
(Continued)

(52) U.S. Cl.
CPC ............ *C09K 11/06* (2013.01); *C07D 209/62* (2013.01); *C07D 265/38* (2013.01);
(Continued)

(58) Field of Classification Search
CPC . C09K 11/06; C09K 2211/1018; C09K 11/00; C09K 11/07; C09K 3/00;
(Continued)

(56) References Cited

U.S. PATENT DOCUMENTS 7,270,893 B2 * 9/2007 Fukuda .................. C09K 11/06
257/102
2014/0027754 A1 * 1/2014 Ueoka .................. C07D 401/10
585/27
(Continued)

FOREIGN PATENT DOCUMENTS

CN 103664909 A 3/2014
JP 2010-260815 A 11/2010
(Continued)

OTHER PUBLICATIONS

KR-20130075949—translation (Year: 2013).*
(Continued)

*Primary Examiner* — Jennifer A Boyd
*Assistant Examiner* — Rachel Simbana
(74) *Attorney, Agent, or Firm* — Lee IP Law, P.C.

(57) ABSTRACT

The present invention relates to: a dopant for an organic optoelectronic device, represented by chemical formula 1; an organic optoelectronic device including the dopant; and a display device.

2 Claims, 4 Drawing Sheets

(51) Int. Cl.
*C07D 403/14* (2006.01)
*C07D 413/14* (2006.01)
*C09K 11/06* (2006.01)
*H10K 50/11* (2023.01)
*H10K 85/60* (2023.01)

(52) U.S. Cl.
CPC ......... *C07D 403/14* (2013.01); *C07D 413/14* (2013.01); *H10K 85/654* (2023.02); *H10K 85/6572* (2023.02); *C09K 2211/1007* (2013.01); *C09K 2211/1018* (2013.01); *H10K 50/11* (2023.02)

(58) Field of Classification Search
CPC ........ C09K 2211/1007; H01L 51/0067; H01L 51/0072; H01L 51/5012; H01L 51/00; H01L 51/0032; H01L 51/005; H01L 51/0052; H01L 51/0054; H01L 51/0058; H01L 51/0062; H01L 51/0065; H01L 51/0068; H01L 51/0069; H01L 51/0071; H01L 51/0064; H01L 51/0051; C07D 209/62; C07D 265/38; C07D 403/14; C07D 413/14; H10K 85/615; H10K 85/6572; H10K 85/626; H10K 85/654; H10K 50/11
See application file for complete search history.

(56) References Cited

U.S. PATENT DOCUMENTS

| | | | | |
|---|---|---|---|---|
| 2015/0053933 A1* | 2/2015 | Lee | ..................... | H01L 51/0067 257/40 |
| 2015/0105564 A1* | 4/2015 | Adachi | ............... | H01L 51/0072 548/440 |
| 2015/0207079 A1* | 7/2015 | Cho | .................. | H10K 85/6572 257/40 |
| 2015/0318487 A1* | 11/2015 | Ito | ....................... | H01L 51/5076 257/40 |
| 2016/0072076 A1* | 3/2016 | Stoessel | ............... | C07D 413/10 257/40 |
| 2016/0164000 A1* | 6/2016 | Li | ........................ | C07D 209/82 548/440 |
| 2016/0211466 A1* | 7/2016 | Ogiwara | ............... | C07D 405/14 |

FOREIGN PATENT DOCUMENTS

| | | | | |
|---|---|---|---|---|
| JP | 2011-153276 A | 8/2011 | | |
| JP | 2011-256143 A | 12/2011 | | |
| JP | 2013-035752 A | 2/2013 | | |
| JP | 2014-511564 A | 5/2014 | | |
| KR | 10-2011-0088457 A | 8/2011 | | |
| KR | 2012031684 A * | 4/2012 | ........... | C07D 209/82 |
| KR | 20130075949 A * | 7/2013 | ........... | C07D 219/02 |
| KR | 10-2014-0000259 A | 1/2014 | | |
| KR | 10-2014-0043043 A | 4/2014 | | |
| KR | 10-2014-0064655 A | 5/2014 | | |
| KR | 10-2015-0024491 A | 3/2015 | | |
| KR | 10-2015-0030660 A | 3/2015 | | |
| KR | 10-2015-0035317 A | 4/2015 | | |
| KR | 10-2015-0036600 A | 4/2015 | | |
| KR | 10-2015-0037093 A | 4/2015 | | |
| KR | 10-2015-0039131 A | 4/2015 | | |
| WO | WO-2011132684 A1 * | 10/2011 | ........... | C07D 403/14 |
| WO | WO 2012/002221 A | 1/2012 | | |
| WO | WO 2012/023947 A | 2/2012 | | |
| WO | WO 2012/108881 A | 8/2012 | | |
| WO | WO 2013/154064 A | 10/2013 | | |
| WO | WO-2014092481 A1 * | 6/2014 | ........... | C07D 487/04 |
| WO | WO-2015008580 A1 * | 1/2015 | ........... | C07D 209/82 |

OTHER PUBLICATIONS

KR-20130075949-A—Translated (Year: 2013).*
WO 2014/092481 A1—translated (Year: 2014).*
WO-2011132684-A1—translated (Year: 2011).*
WO 2011/132684 A1—updated translation (Year: 2011).*
WO-2015008580-A1—translation (Year: 2015).*
Meng, H.; Herron, N. Organic Small Molecule Materials for Organic Light-Emitting Diodes. In Organic Light Emitting Materials and Devices, 2nd Ed.; Shijan, S; Herron, N.; Meng, H. Taylor & Francis Group; 2015; pp. 296-395). (Year: 2015).*
KR-2012031684-A—translation (Year: 2012).*

* cited by examiner

DOPANT FOR ORGANIC OPTOELECTRONIC DEVICE, ORGANIC OPTOELECTRONIC DEVICE, AND DISPLAY DEVICE

CROSS REFERENCE TO RELATED APPLICATIONS

This is the U.S. national phase application based on PCT Application No. PCT/KR2015/011321, filed Oct. 26, 2015, which is based on Korean Patent Application No. 10-2015-0068121, filed May 15, 2015, the entire contents of all of which are hereby incorporated by reference.

TECHNICAL FIELD

A dopant for an organic optoelectronic device, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode.

Performance of an organic light emitting diode may be affected by characteristics of the organic layer, and among them, may be mainly affected by characteristics of an organic material in the organic layer. Particularly, a high efficiency light emitting material is required to develop for a large-sized organic light emitting diode, and accordingly, a phosphorescent dopant is being widely used. However, the phosphorescent dopant should inevitably use for example a complex compound including a metal or a heavy metal such as iridium, platinum, copper, beryllium, or the like and costs high.

DISCLOSURE

Technical Problem

According to an embodiment, a dopant for an organic optoelectronic device capable of substituting a complex compound including a metal or a heavy metal and having high efficiency is provided.

An organic optoelectronic device including the dopant is provided.

According to another embodiment, a display device including the organic optoelectronic device is provided.

Technical Solution

According to an embodiment, a dopant for an organic optoelectronic device represented by Chemical Formula 1 is provided.

[Chemical Formula 1]

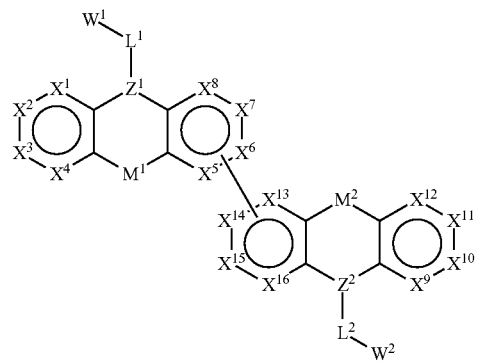

In Chemical Formula 1,
$W^1$ and $W^2$ are independently a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a substituted or unsubstituted aromatic heterocyclic group having at least one nitrogen; or a combination thereof, $L^1$ and $L^2$ are independently a substituted or unsubstituted C6 to C30 arylene group or a substituted or unsubstituted pyridinyl group, $X^1$ to $X^{16}$ are independently N or $CR^a$, $Z^1$ and $Z^2$ are independently N, B, $CR^b$, or $SiR^c$, $M^1$ and $M^2$ are independently a single bond, $CR^dR^e$, $SiR^fR^g$, $NR^h$, O, or S, $R^a$ is hydrogen, deuterium, a substituted or unsubstituted C1 to 010 alkyl group, a substituted or unsubstituted C1 to 010 alkenyl group, a substituted or unsubstituted C1 to 010 alkoxy group, a substituted or unsubstituted C6 to C30 aryl group, or a substituted or unsubstituted C3 to C30 heterocyclic group, and $R^b$ to $R^h$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof.

According to another embodiment, an organic optoelectronic device includes an anode and a cathode facing each other and an organic layer disposed between the anode and the cathode, wherein the organic layer includes the dopant.

According to another embodiment, a display device including the organic optoelectronic device is provided.

Advantageous Effects

A dopant for an organic optoelectronic device capable of replacing a complex compound including a metal or a heavy metal and having high efficiency is provided.

BEST MODE

Figure 1:
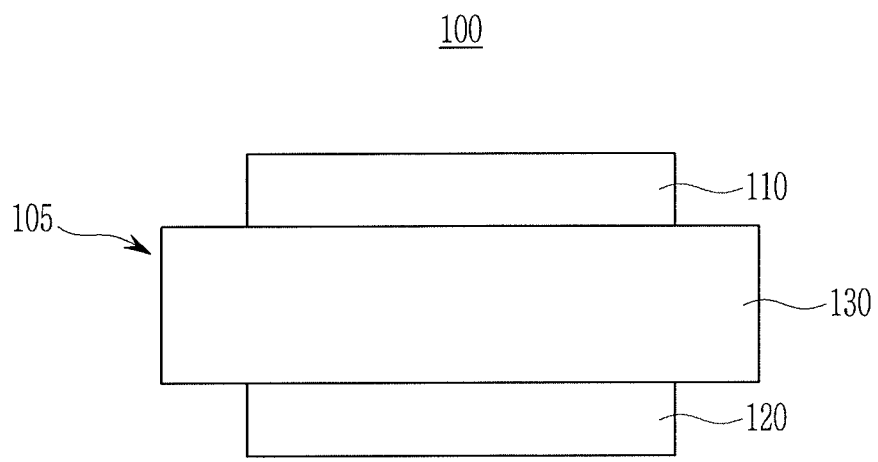
FIG. 1 is a cross-sectional view of an organic light emitting diode according to an embodiment.

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 aryl group, a C2 to C30 heterocyclic group, a C1 to C20 alkoxy group, a C1 to C10 trifluoroalkyl group such as a trifluoromethyl group, or a cyano group.

In addition, two adjacent substituents of the substituted halogen, a hydroxy group, an amino group, C1 to C20 amine group, a nitro group, C3 to C40 silyl group, C1 to C30 alkyl group, C1 to C10 alkylsilyl group, C6 to C30 aryl group, C3 to C30 heterocyclic group, C1 to C20 alkoxy group, C1 to C10 trifluoroalkyl group such as trifluoromethyl group, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom and remaining carbons in one functional group. The heteroatom may be selected from N, O, S, P, and Si.

In the present specification, "aryl group" refers to a group including at least one hydrocarbon aromatic moiety, and includes hydrocarbon aromatic moieties linked by a single bond and hydrocarbon aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification, "heterocyclic group" is a concept including a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

More specifically, the substituted or unsubstituted aryl group and/or the substituted or unsubstituted heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quaterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a combination thereof, or a combined fused ring of the foregoing groups, but is not limited thereto.

In the present specification, the substituted or unsubstituted arylene group or the substituted or unsubstituted heteroarylene group or the substituted or unsubstituted divalent heterocyclic group has two linking groups in the substituted or unsubstituted aryl group or the substituted or unsubstituted heterocyclic group, and may be, for example, a substituted or unsubstituted phenylene group, a substituted or unsubstituted naphthalene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quarterphenylene group, a substituted or unsubstituted chrysenylene group, a substituted or unsubstituted triperylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolene group, a substituted or unsubstituted imidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolene group, a combination thereof, or a fused form of combinations thereof, but are not limited thereto.

In one example of the present invention, the substituted or unsubstituted arylene group or the substituted or unsubstituted heteroarylene group or the substituted or unsubstituted divalent heterocyclic group may be one of a substituted or unsubstituted phenylene group, a substituted or unsubstituted biphenylene group, a substituted or unsubstituted terphenylene group, a substituted or unsubstituted quaterphenylene group, a substituted or unsubstituted naphthalene group, and a substituted or unsubstituted pyrimidylene group, or a combination thereof.

In the specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

In the present specification, a dopant is a light emitting material in a specific wavelength region by being doped in a host and receiving energy or carrier from a host and is different from a host that is an energy or carrier source.

Hereinafter, a dopant for an organic optoelectronic device according to an embodiment is described.

A dopant for an organic optoelectronic device according to an embodiment is represented by Chemical Formula 1.

[Chemical Formula 1]

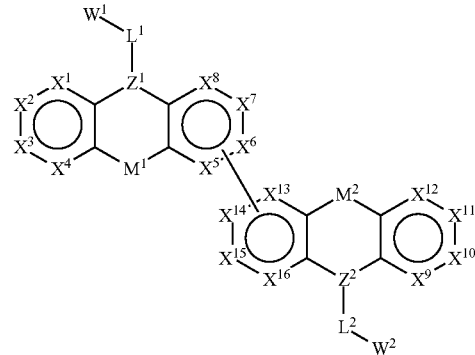

In Chemical Formula 1, $W^1$ and $W^2$ are independently an electron withdrawing group, for example a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a substituted or unsubstituted aromatic heterocyclic group having at least one nitrogen; or a combination thereof, $L^1$ and $L^2$ are independently a substituted or unsubstituted C6 to C30 arylene group or a substituted or unsubstituted pyridinyl group, $X^1$ to $X^{16}$ are independently N or $CR^a$ $Z^1$ and $Z^2$ are independently N, B, $CR^b$, or $SiR^c$, $M^1$ and $M^2$ are independently a single bond, $CR^dR^e$, $SiR^fR^g$, $NR^h$, O, or S, $R^a$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group, or a substituted or unsubstituted C3 to C30 heterocyclic group, and $R^b$ to $R^h$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof.

Since the dopant represented by Chemical Formula 1 has a chromophore having a structure that an electron donating core is substituted with an electron withdrawning group, HOMO-LUMO may be easily separated, and an energy gap between singlet energy ($S^1$) and triplet energy ($T^1$) may be effectively reduced. Accordingly, since a reverse intersystem crossing (RIC) from the triplet exited state (T1) to the singlet exited state (S1) easily occurs, the dopant may all use fluorescence occurring through the reverse intersystem crossing (RIC) from the triplet exited state (T1) to the singlet exited state (S1) as well as fluorescence of the singlet exited state (S1) and thus increase luminous efficiency.

For example, the dopant represented by Chemical Formula 1 may have an energy gap ($|S^1-T^1|$) between singlet energy and triplet energy of less than or equal to about 0.35 eV. For example, the dopant represented by Chemical Formula 1 may have an energy gap between singlet energy and triplet energy of about 0.01 eV to 0.35 eV.

Furthermore, the dopant represented by Chemical Formula 1 includes two of the chromophore and thus may be variously designed to use double chromophores. Accordingly, the dopant may realize a color with high color purity by adjusting a full width at half maximum (FWHM) of a chromophore wavelength region as well as with variety from a short wavelength to a long wavelength by adjusting the chromophore wavelength region depending on a bonding position and the number of an electron donor core and an electron withdrawing group. Herein, the full width at half maximum (FWHM) is a width of a wavelength region corresponding to a half of maximum light emitting wavelength, and when the full width at half maximum (FWHM) is narrow, the dopant may selectively emit light in a narrow wavelength region and thus accomplish high wavelength selectivity and high color purity.

In addition, the dopant may realize much higher external quantum efficiency due to the double chromophores.

Accordingly, the dopant represented by Chemical Formula 1 may be used as a fluorescent dopant having high efficiency and high color purity and replacing a conventional phosphorescent dopant including a heavy metal such as iridium, platinum, copper, or the like.

For example, $L^1$ and $L^2$ of Chemical Formula 1 may independently be a substituted or unsubstituted C6 to C30 arylene group, or a substituted or unsubstituted pyridinyl group, wherein 'substituted' may for example refer to substitution with a cyano group, a halogen, carbazolyl group, a C1 to C5 trifluoroalkyl group, or a combination thereof.

For example, at least one of $X^1$ to $X^{16}$, $Z^1$, $Z^2$, $M^1$, and $M^2$ of Chemical Formula 1 may include nitrogen (N). For example, at least one of $Z^1$, $Z^2$, $M^1$, and $M^2$ of Chemical Formula 1 may include nitrogen (N). For example, $Z^1$ and $Z^2$ of Chemical Formula 1 may be nitrogen (N).

For example, in the definition of $W^1$ and $W^2$ of Chemical Formula 1, the substituted or unsubstituted aromatic heterocyclic group having at least one nitrogen may be for example a substituted or unsubstituted triazinyl group; a substituted or unsubstituted pyrimidinyl group; a substituted or unsubstituted pyridinyl group; a substituted or unsubstituted quinazolinyl group; a substituted or unsubstituted quinoxalinyl group; or a combination thereof.

For example, the substituted or unsubstituted aromatic heterocyclic group having at least one nitrogen may be selected from a triazinyl group substituted with a C6 to C30 aryl group or a C3 to C30 heterocyclic group; a pyrimidinyl group substituted with a C6 to C30 aryl group or a C3 to C30 heterocyclic group; a pyridinyl group substituted with a C6 to C30 aryl group or a C3 to C30 heterocyclic group; a quinazolinyl group substituted with a C6 to C30 aryl group or a C3 to C30 heterocyclic group; a quinoxalinyl group substituted with a C6 to C30 aryl group or a C3 to C30 heterocyclic group; or a combination thereof.

For example, the substituted or unsubstituted aromatic heterocyclic group having at least one nitrogen may be a group represented by Chemical Formula A.

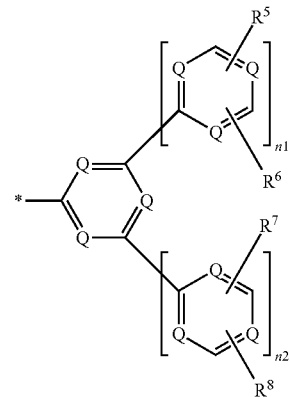

[Chemical Formula A]

In Chemical Formula A,
Q is independently N, C, or $CR^i$,
at least one of Q's is N,
$R^5$ to $R^8$ and $R^i$ are independently hydrogen, deuterium, a substituted or unsubstituted C1 to C10 alkyl group, a substituted or unsubstituted C6 to C30 aryl group, or a substituted or unsubstituted C3 to C30 heterocyclic group, or a combination thereof,
$R^5$ and $R^6$ are independently present or linked with each other to form a ring,
$R^7$ and $R^8$ are independently present or linked with each other to form a ring,
n1 and n2 are independently 0 or 1, and
is a linking point with $L^1$ or $L^2$ of Chemical Formula 1.
In Chemical Formula A, each of $R^5$ to $R^8$ may be for example hydrogen.
In Chemical Formula A, for example, each of n1 and n2 may be 1, and for example each of $R^5$ to $R^8$ may be hydrogen.
For example, in Chemical Formula A, 1 to 5 of Q's may be N and the remainder may be $CR^i$.
For example, Chemical Formula A may be represented by Chemical Formula A-1 according to a position and the number of nitrogen.

[Chemical Formula A-1]

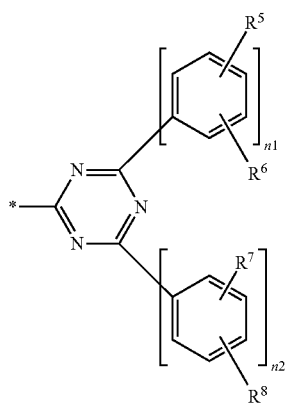

In Chemical Formula A-1, $R^1$ to $R^8$, $n^1$, and $n^2$ are the same as described above.

In Chemical Formula A-1, each of $R^5$ to $R^8$ may be for example hydrogen.

In Chemical Formula A-1, each of n1 and n2 may be 1 and each of $R^5$ to $R^8$ may be for example hydrogen.

For example, $W^1$ and $W^2$ of Chemical Formula 1 may independently be selected from a cyano group; a halogen; a C1 to C10 alkyl group substituted with a cyano group or a halogen; a C6 to C30 aryl group substituted with a cyano group or a halogen; a C3 to C30 heterocyclic group substituted with a cyano group or a halogen; a triazinyl group substituted with a C6 to C30 aryl group or a C3 to C30 heterocyclic group; a pyrimidinyl group substituted with a C6 to C30 aryl group or a C3 to C30 heterocyclic group; a pyridinyl group substituted with a C6 to C30 aryl group or a C3 to C30 heterocyclic group; a quinazolinyl group substituted with a C6 to C30 aryl group or a C3 to C30 heterocyclic group; a quinoxalinyl group substituted with a C6 to C30 aryl group or a C3 to C30 heterocyclic group; or a combination thereof.

For example, $W^1$ and $W^2$ of Chemical Formula 1 may independently be selected from a cyano group; a halogen; a C1 to C10 alkyl group substituted with a cyano group or a halogen; a C6 to C30 aryl group substituted with a cyano group or a halogen; a C3 to C30 heterocyclic group substituted with a cyano group or a halogen; a group represented by Chemical Formula A; a carbazolyl group; or a combination thereof.

The dopant may be for example represented by Chemical Formula 1-I.

[Chemical Formula 1-I]

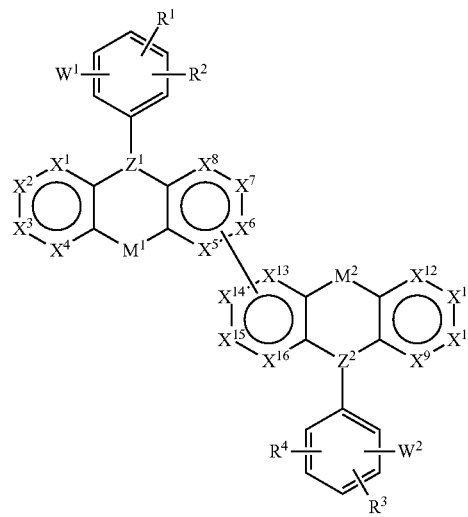

In Chemical Formula 1-I,
$W^1$, $W^2$, $X^1$ to $X^{16}$, $Z$, $Z^2$, $M^1$, and $M^2$ are the same as described above, and
$R^1$ to $R^4$ are independently hydrogen; deuterium; a cyano group; a nitro group; an amide group; a sulfonyl group; a phosphine group; a phosphoryl group; a halogen; a C1 to C10 alkyl group substituted with a cyano group, a nitro group, an amide group, a sulfonyl group, a phosphine group, a phosphoryl group, or a halogen; a C6 to C30 aryl group substituted with a cyano group, a nitro group, an amide group, a sulfonyl group, a phosphine group, a phosphoryl group, or a halogen; a C3 to C30 heterocyclic group substituted with a cyano group, a nitro group, an amide group, a sulfonyl group, a phosphine group, a phosphoryl group, or a halogen; a substituted or unsubstituted aromatic heterocyclic group having at least one nitrogen; or a group represented by Chemical Formula B.

[Chemical Formula B]

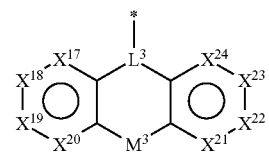

In Chemical Formula B,
$X^{17}$ to $X^{24}$ are independently N or $CR^j$,
$L^3$ is N, B, $CR^k$, or $SiR^l$,
$M^3$ is a single bond, $CR^mR^n$, $SiR^oR^p$, $NR^q$, O, or S,
$R^j$ is hydrogen, deuterium, a substituted or unsubstituted C1 to C10 alkyl group, a substituted or unsubstituted C1 to C10 alkenyl group, a substituted or unsubstituted C1 to C10 alkoxy group, a substituted or unsubstituted C6 to C30 aryl group, or a substituted or unsubstituted C3 to C30 heterocyclic group,
$R^k$ to $R^q$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 heterocyclic group, a substituted or unsubstituted amine group, a substituted or unsubstituted C1 to C30 alkoxy group, a substituted or unsubstituted C1 to C30 carbonyl group, a substituted or unsubstituted C1 to C30 carbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C1 to C30 ureide group, a halogen, a cyano group, a hydroxyl group, an amino group, a nitro group, a carboxyl group, or a combination thereof, and is a linking point with Chemical Formula 1-I.

For example, in Chemical Formula 1-I, $R^1$ may be hydrogen or the same as $W^1$ and $R^3$ may be hydrogen or the same as $W^2$.

For example, in Chemical Formula 1-I, $R^2$ may be hydrogen or the group represented by Chemical Formula B and $R^4$ may be hydrogen or the group represented by Chemical Formula B.

For example, in Chemical Formula 1-I, each of $R^1$, $R^2$, $R^3$, and $R^4$ may be hydrogen.

For example, in Chemical Formula 1-I, each of $R^1$, $R^2$, $R^3$, and $R^4$ may be hydrogen and $W^1$ and $W^2$ may independently be the group represented by Chemical Formula A.

For example, in Chemical Formula 1-I, each of $R^1$ and $R^3$ may be the same as $W^1$ and $W^2$ and $R^2$ and $R^4$ may be the group represented by Chemical Formula B.

For example, in Chemical Formula 1-I, each of $R^1$ and $R^3$ may be selected from a cyano group; a halogen; a C1 to C10 alkyl group substituted with a cyano group or a halogen; a C6 to C30 aryl group substituted with a cyano group or a halogen; a C3 to C30 heterocyclic group substituted with a cyano group or a halogen and $R^2$ and $R^4$ may be the group represented by Chemical Formula B.

For example, Chemical Formula B may be one of Chemical Formulae B-1 to B-6.

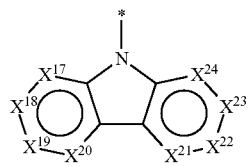

[Chemical Formula B-1]

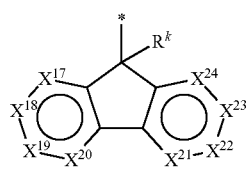

[Chemical Formula B-2]

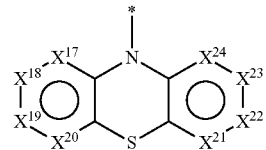

[Chemical Formula B-3]

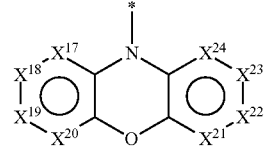

[Chemical Formula B-4]

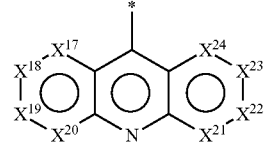

[Chemical Formula B-5]

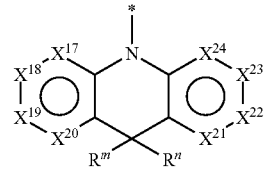

[Chemical Formula B-6]

In Chemical Formulae B-1 to B-6, $X^{17}$ to $X^{24}$, $R^k$, $R^m$, and $R^n$ are the same as described above.

The dopant represented by Chemical Formula 1 may be for example represented by one of Chemical Formulae 2 to 7.

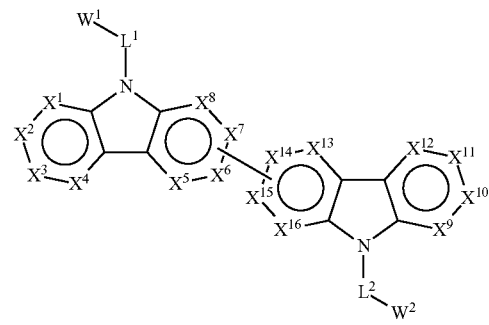

[Chemical Formula 2]

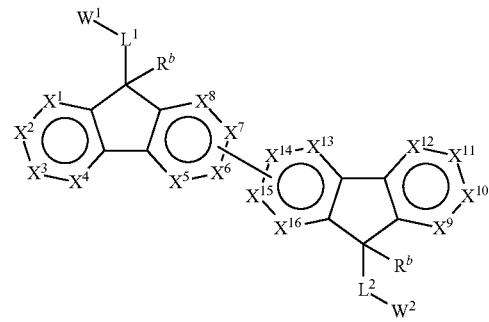

[Chemical Formula 3]

[Chemical Formula 4]

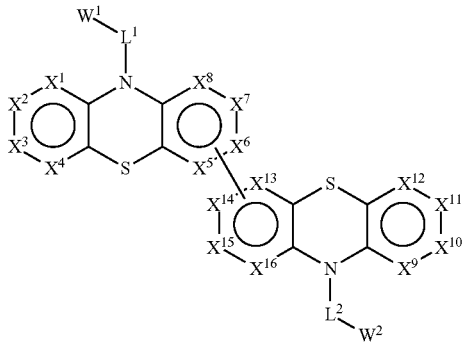

[Chemical Formula 5]

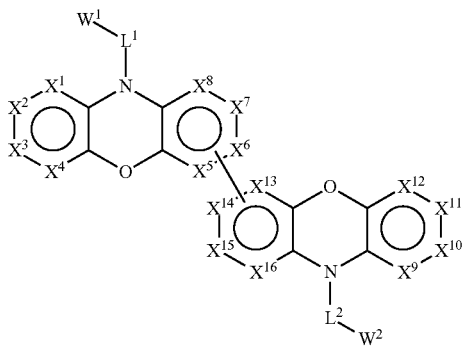

[Chemical Formula 6]

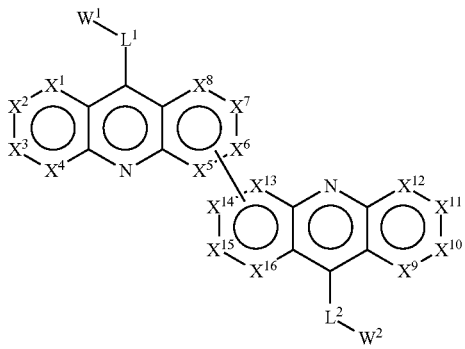

[Chemical Formula 7]

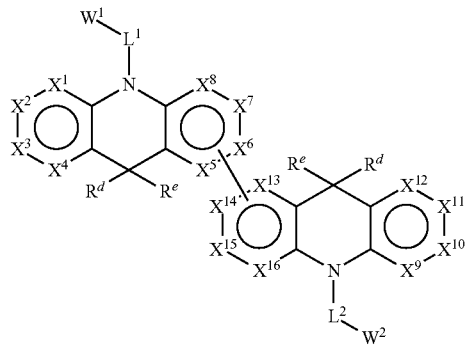

In Chemical Formulae 2 to 7, $W^1$, $W^2$, $L^1$, $L^2$, $X^1$ to $X^{16}$, $R^b$, $R^d$, and $R^e$ are the same as described above.

For example, in Chemical Formulae 2 to 7, $X^1$ to $X^{16}$ may be C or CH.

For example, in Chemical Formulae 2 to 7, one of $X^1$ to $X^{16}$ may be N and the remainder may be CH.

For example, in Chemical Formulae 2 to 7, $X^1$ to $X^{16}$ may be CH and $L^1$ and $L^2$ may be a substituted or unsubstituted phenylene group.

For example, in Chemical Formulae 2 to 7, one of $X^1$ to $X^{16}$ may be N and the remainder may be CH, and $L^1$ and $L^2$ may be a substituted or unsubstituted phenylene group.

For example, in Chemical Formulae 2 to 7, $X^1$ to $X^{16}$ may be CH and $L^1$ and $L^2$ may be a substituted or unsubstituted phenylene group wherein 'substituted' refers to substitution with one selected from a cyano group; a carbazolyl group; a halogen; or a C1 to C5 alkyl group substituted with a halogen.

For example, in Chemical Formulae 2 to 7, one of $X^1$ to $X^{16}$ may be N and the remainder may be CH, and $L^1$ and $L^2$ may be a substituted or unsubstituted phenylene group wherein 'substituted' refers to substitution with one selected from a cyano group; a carbazolyl group; a halogen; or a C1 to C5 alkyl group substituted with a halogen.

For example, in Chemical Formulae 2 to 7, $X^1$ to $X^{16}$ may be CH and $L^1$ and $L^2$ may be a substituted or unsubstituted phenylene group wherein 'substituted' refers to substitution with two selected from a cyano group; a carbazolyl group; a halogen; or a C1 to C5 alkyl group substituted with a halogen.

For example, in Chemical Formulae 2 to 7, one of $X^1$ to $X^{16}$ may be N and the remainder may be CH, and $L^1$ and $L^2$ may be a substituted or unsubstituted phenylene group wherein 'substituted' refers to substitution with two selected from a cyano group; a carbazolyl group; a halogen; or a C1 to C5 alkyl group substituted with a halogen.

The dopant may be for example one of compounds of Group 1, but is not limited thereto.

[Group 1]
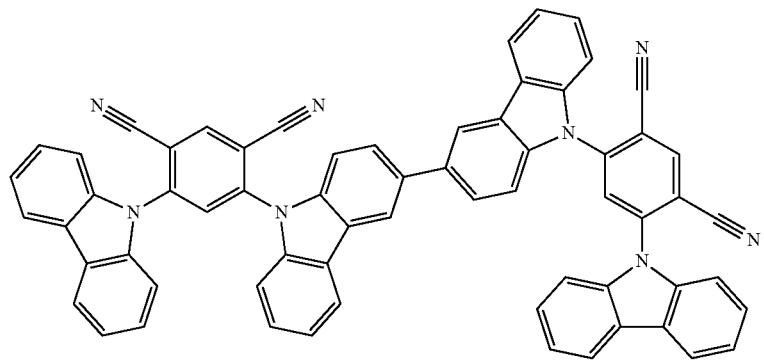
1
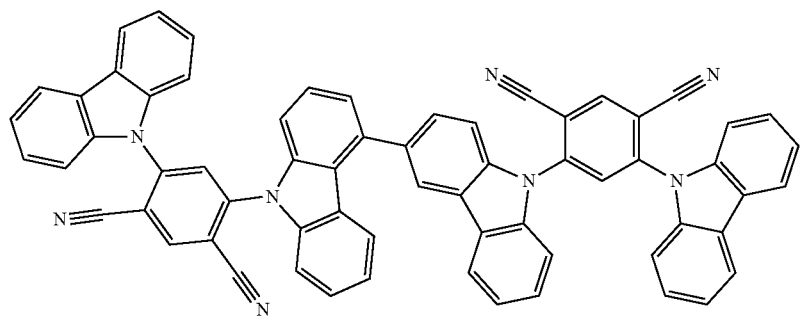
2
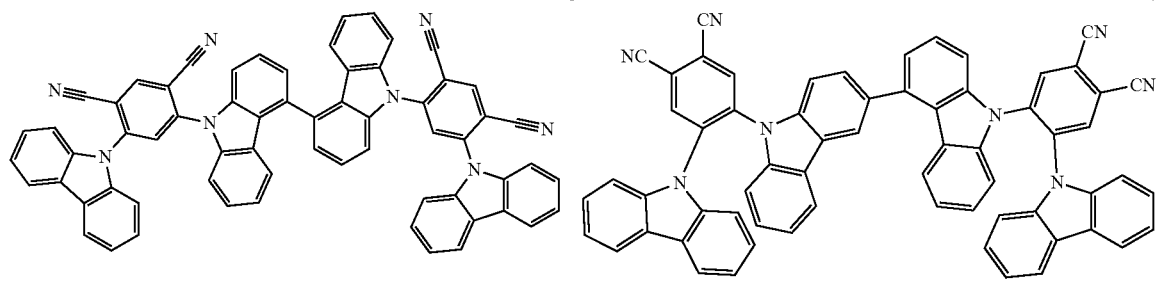
3        4
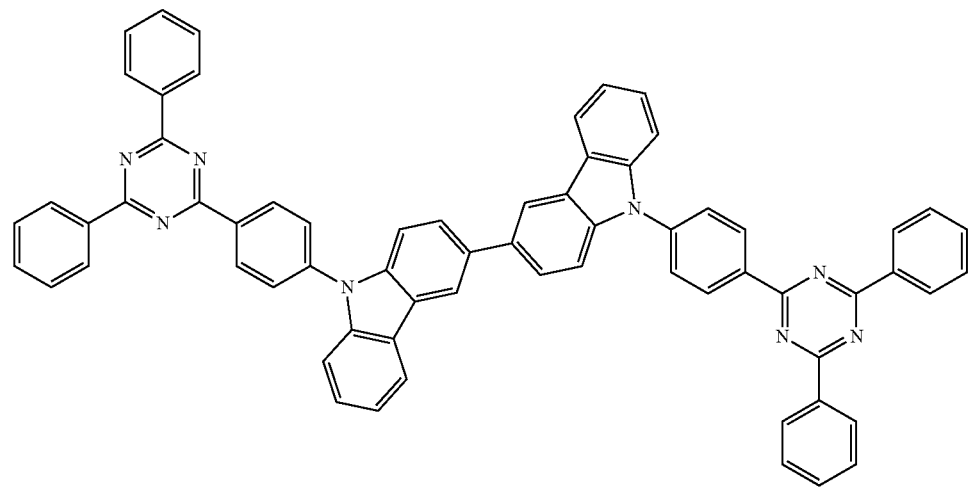
5

6
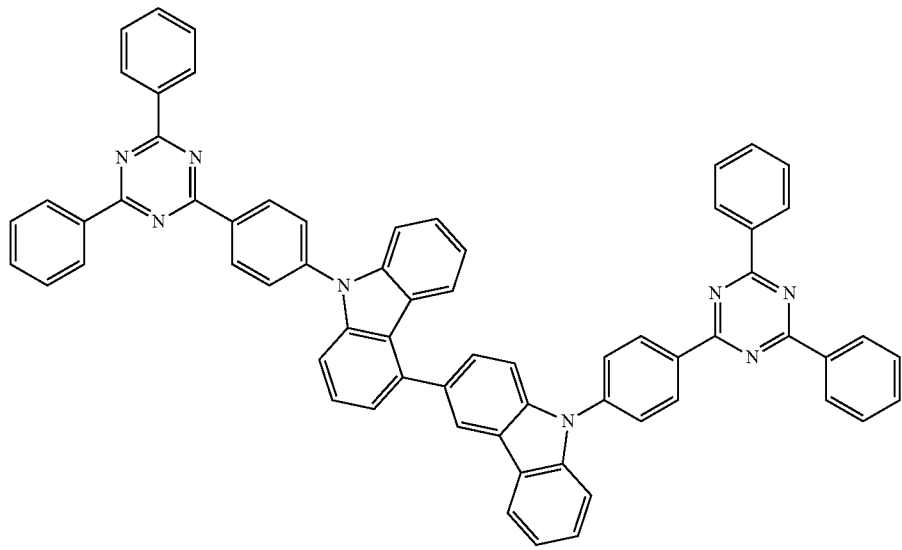
7
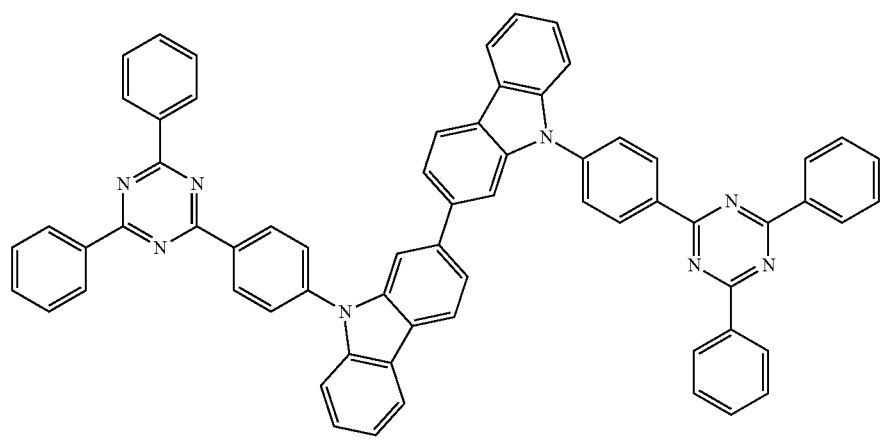
8
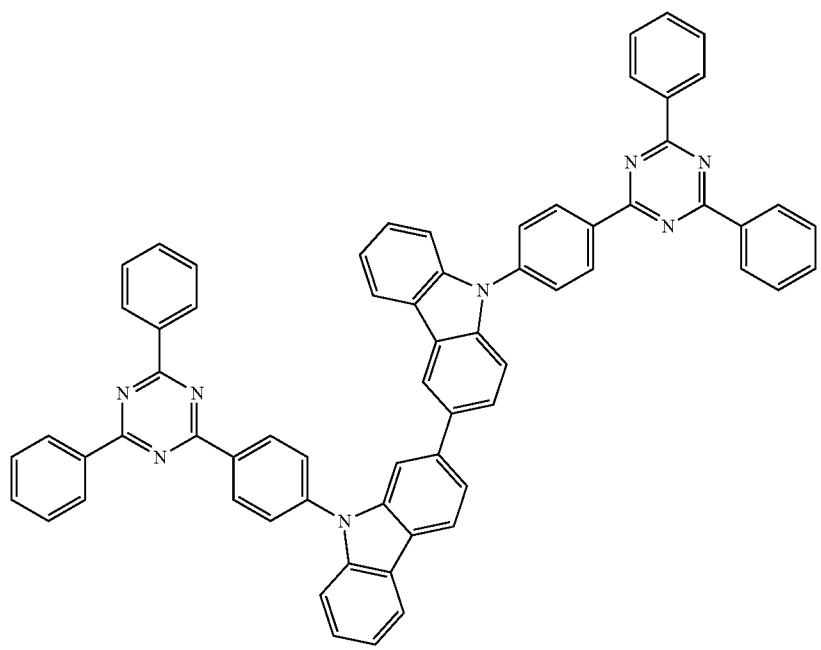

-continued
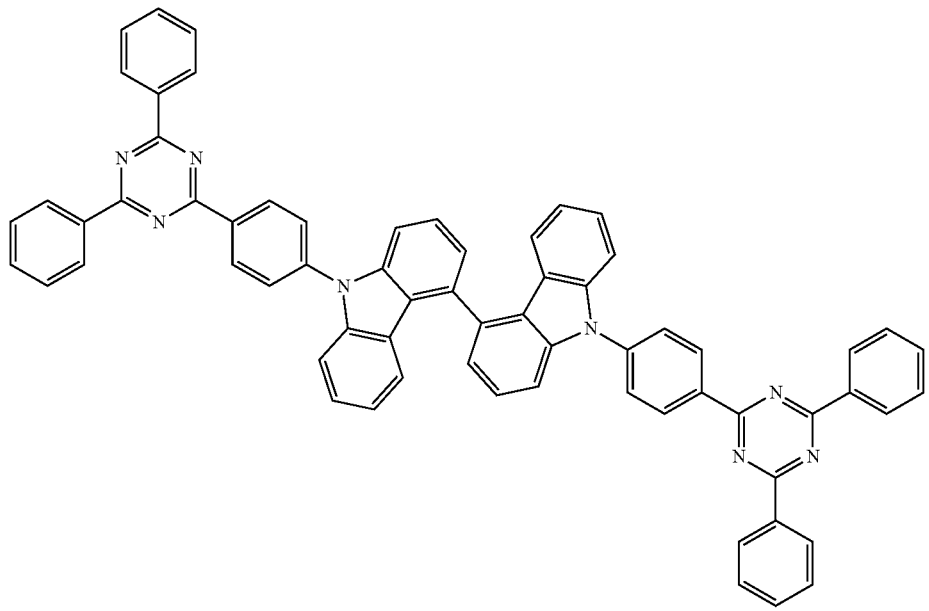
9
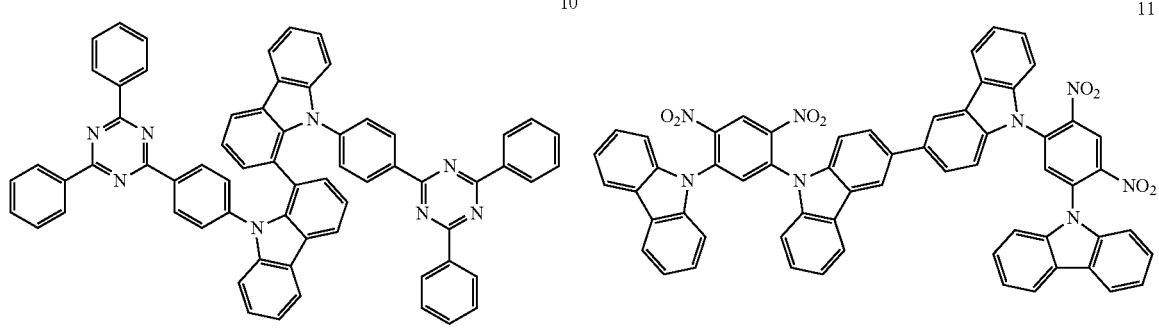
10 11
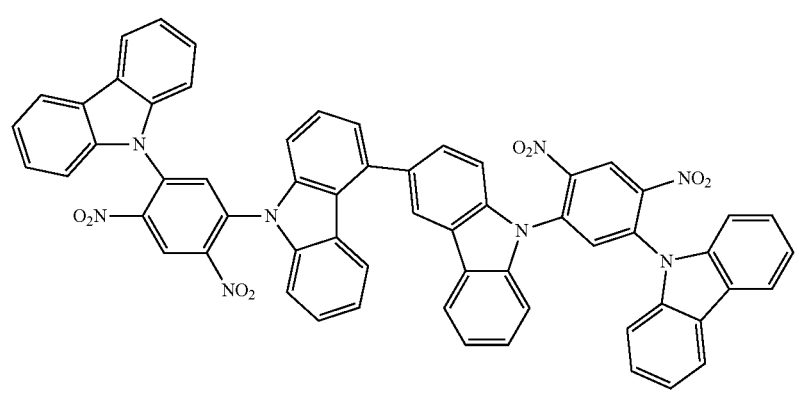
12
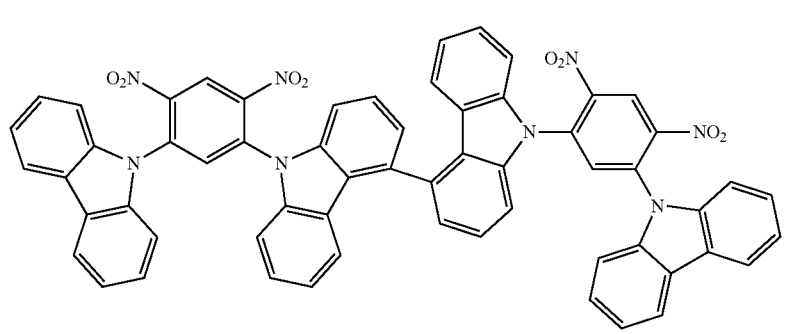
13

-continued
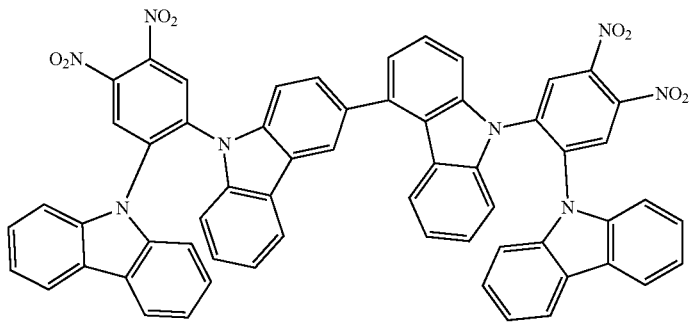
14
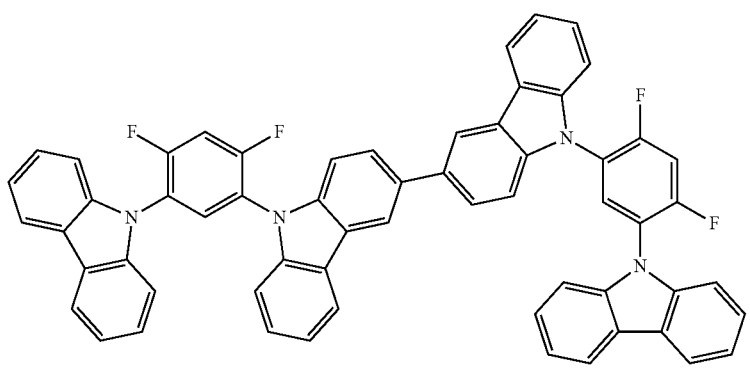
15
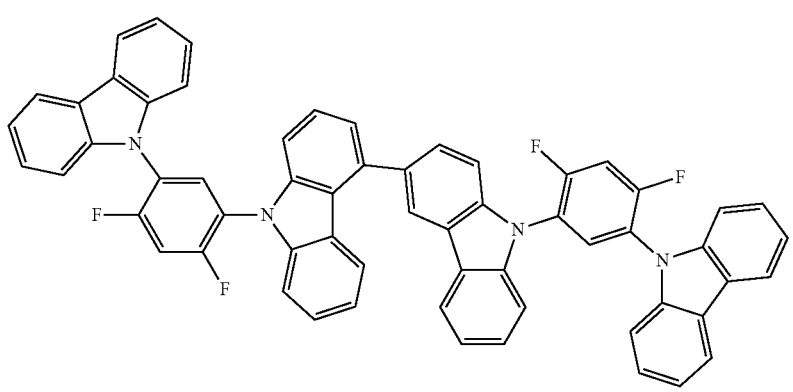
16
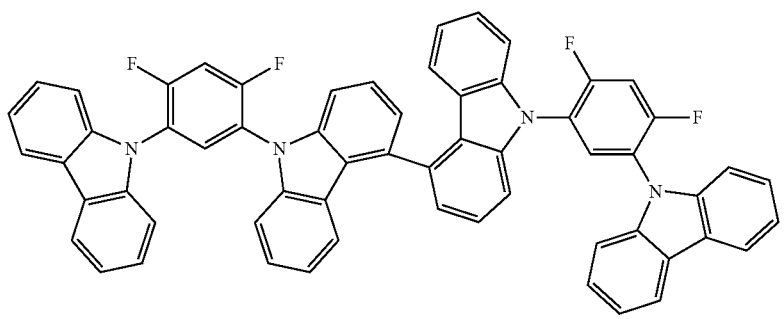
17

18
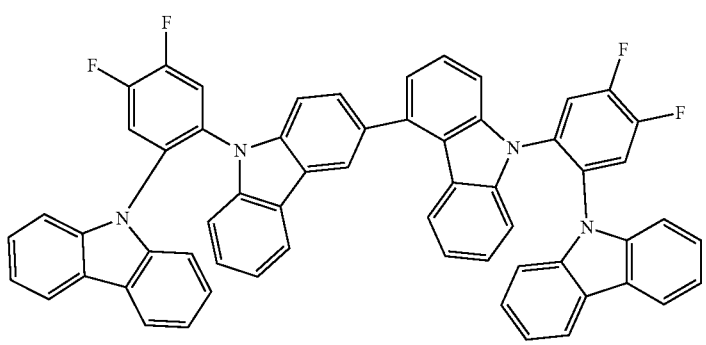
19
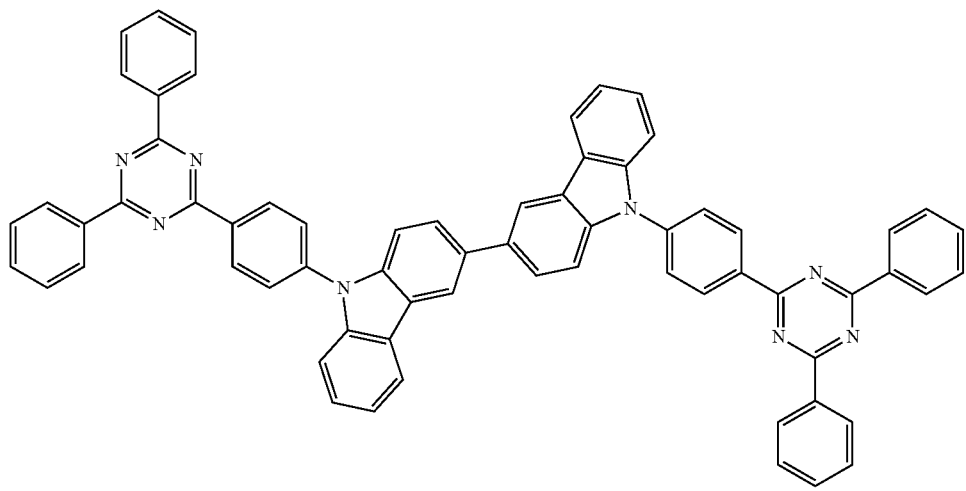
20
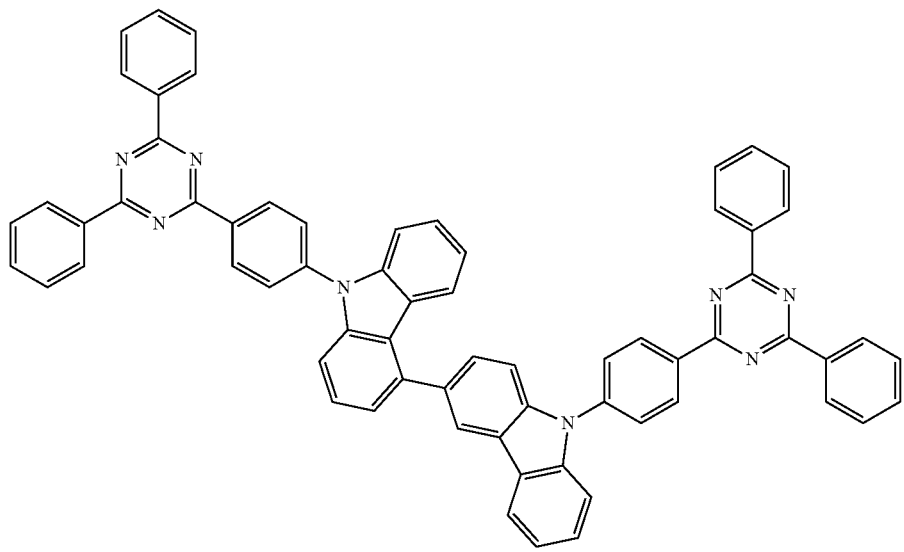

-continued
21
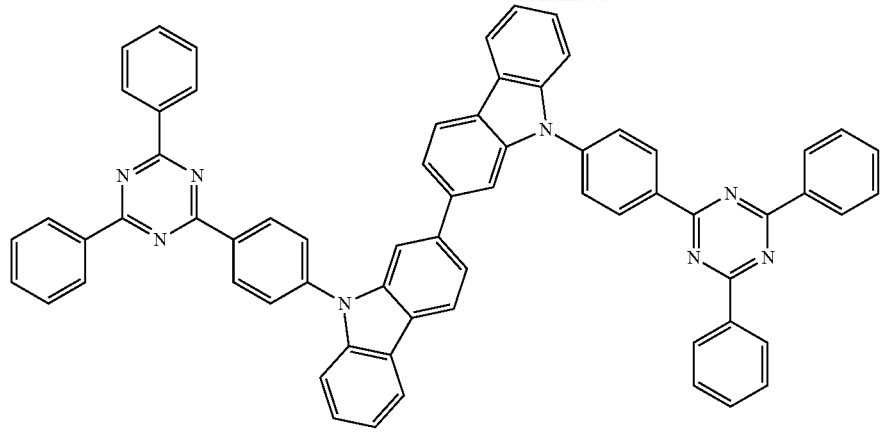
22
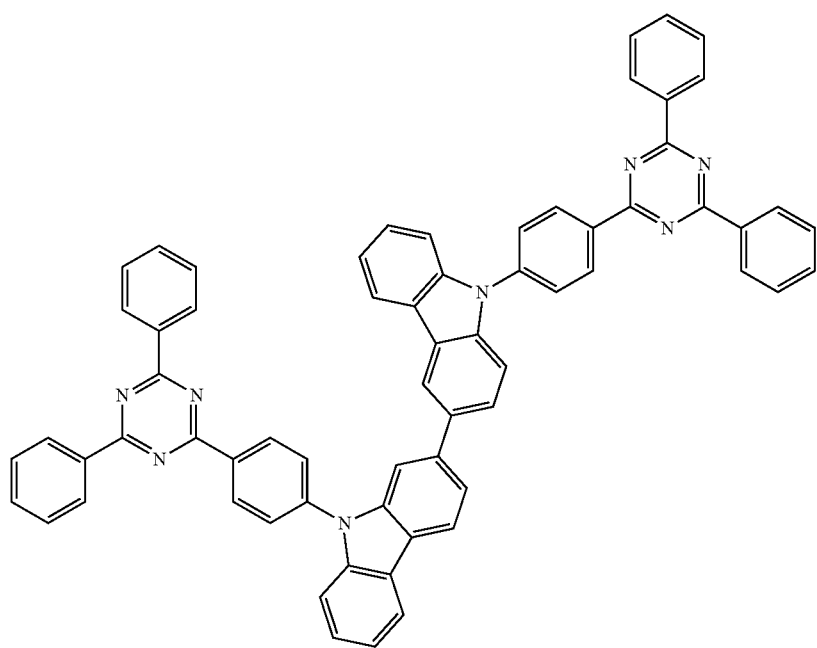

-continued
23
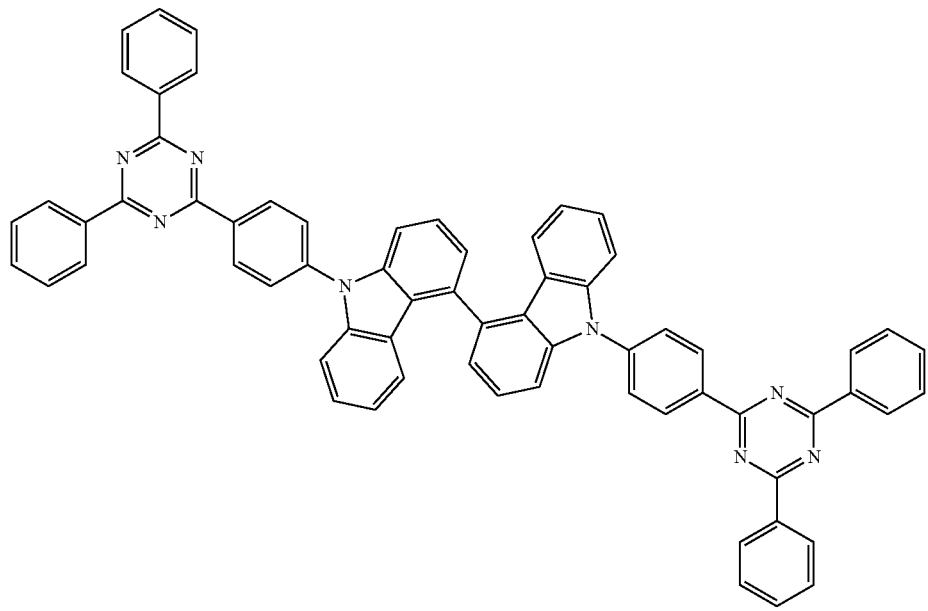
24
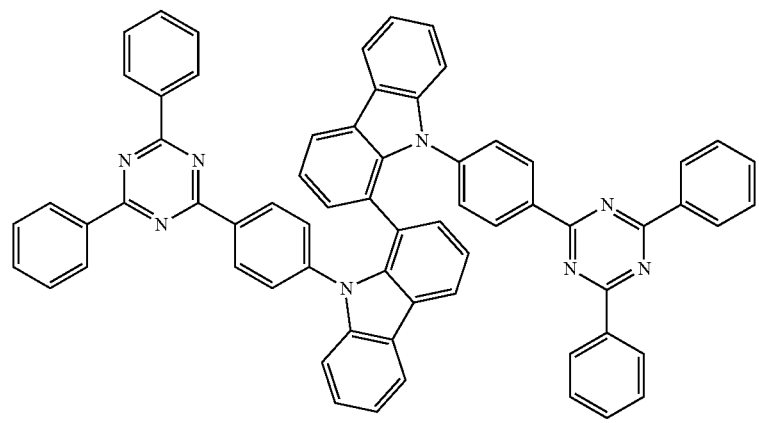
25
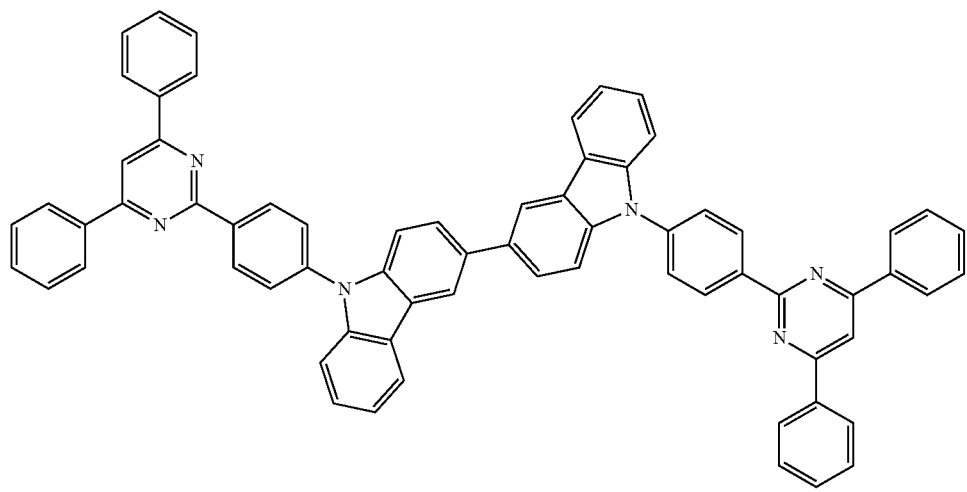

26
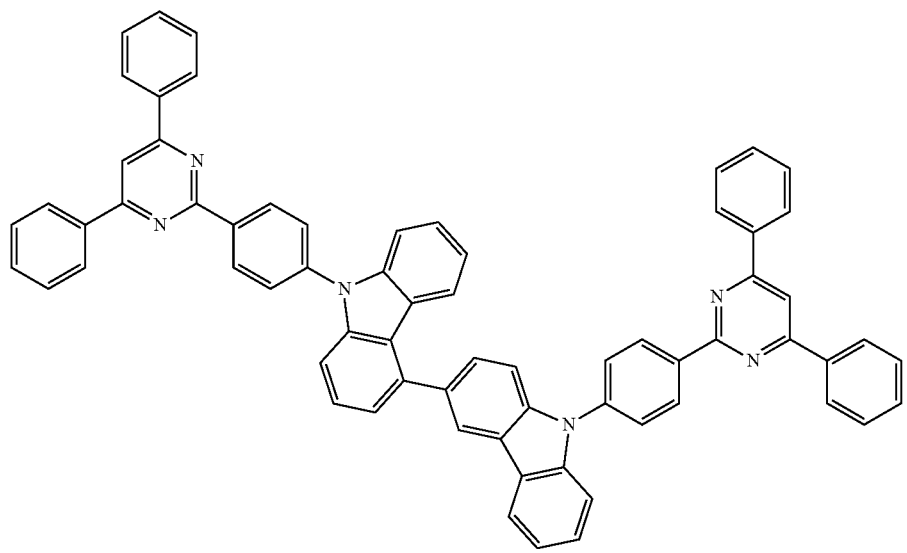
27
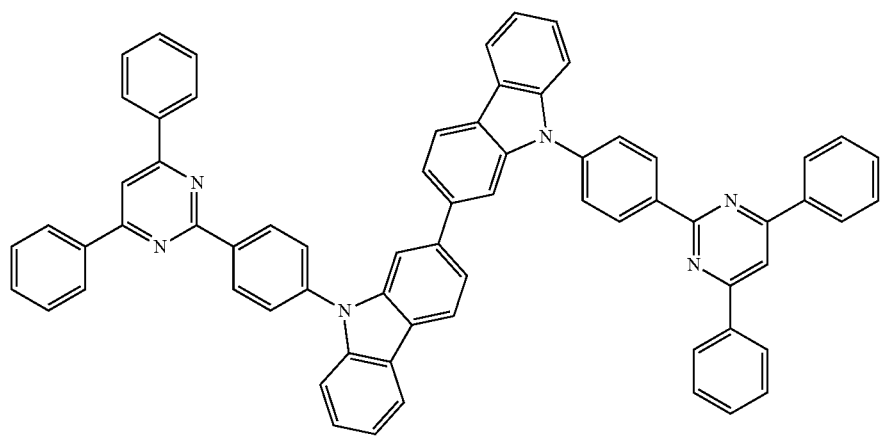
28
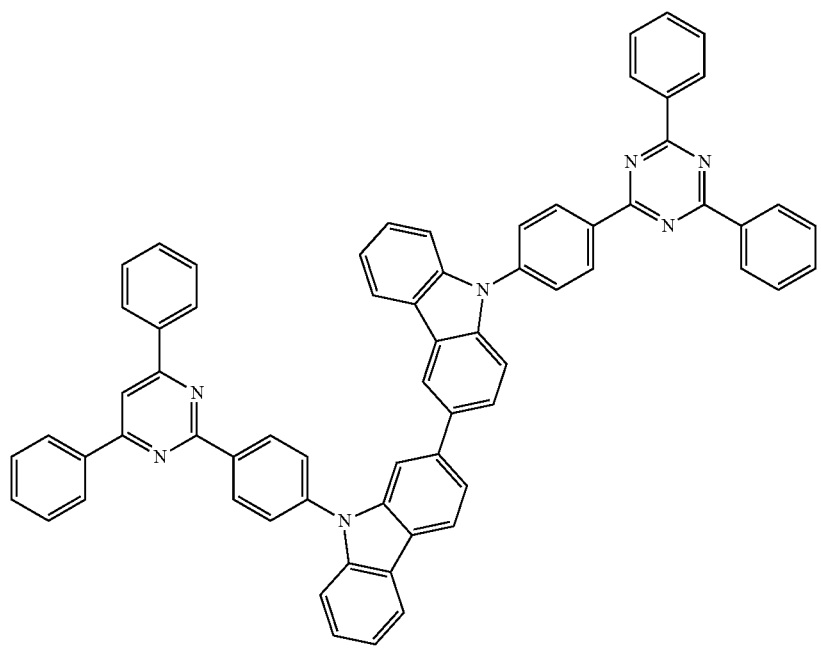

29
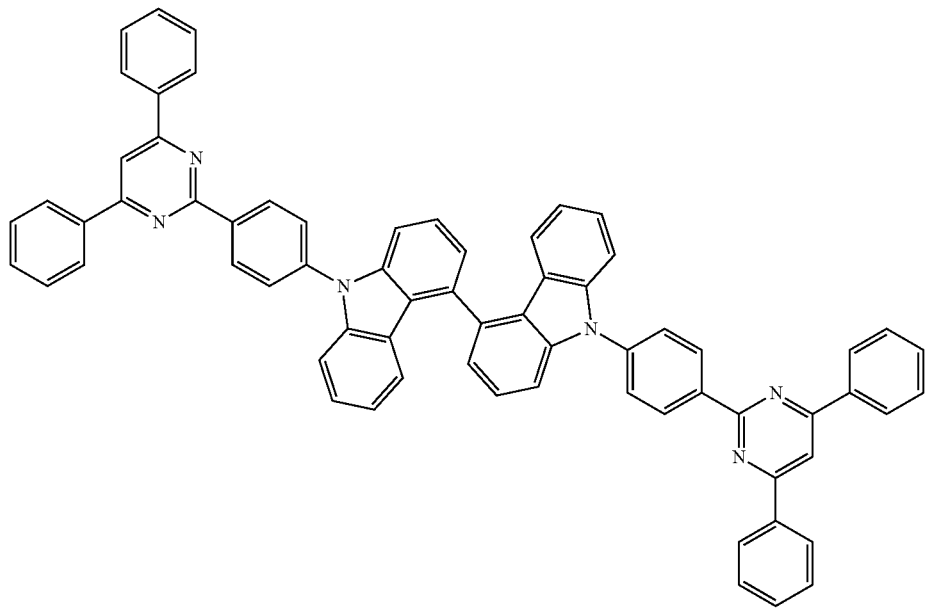
30
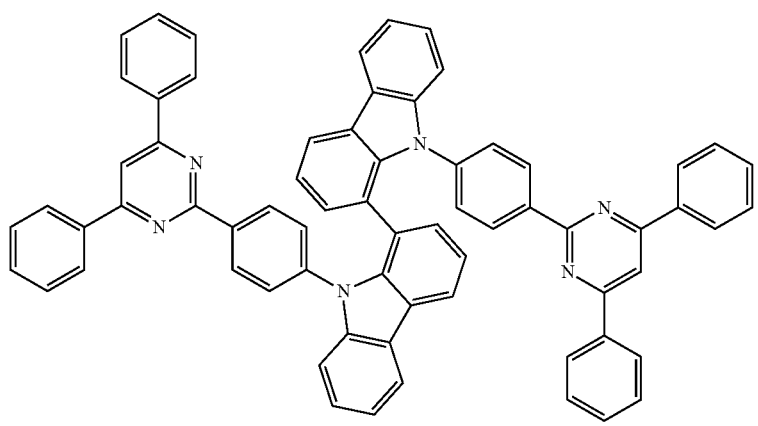
31
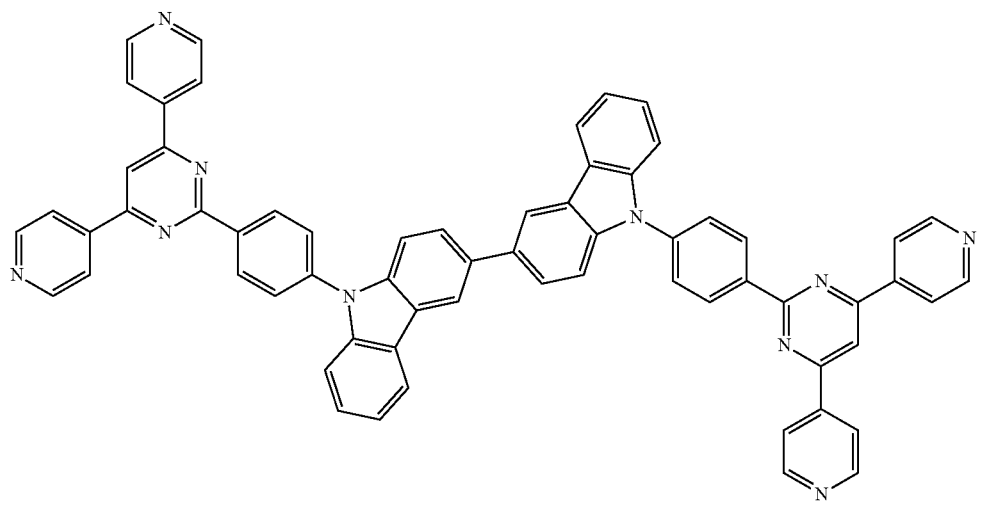

-continued
32
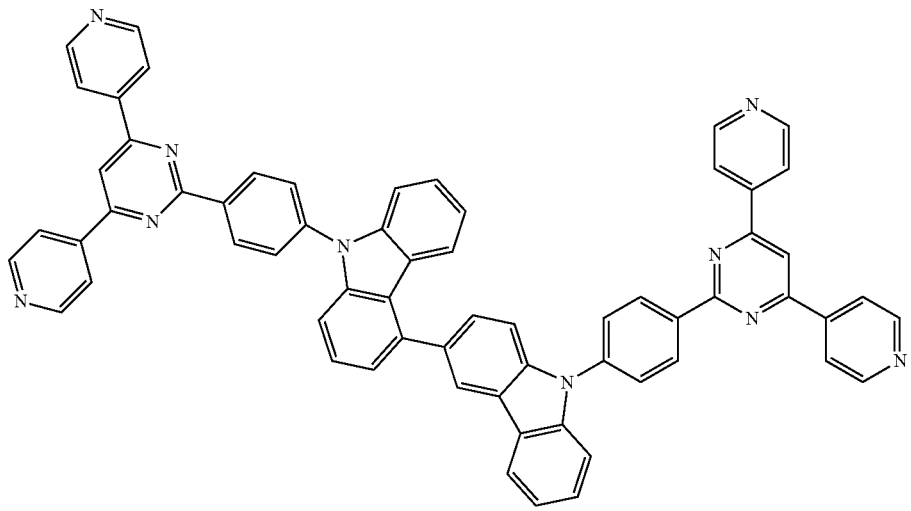
33
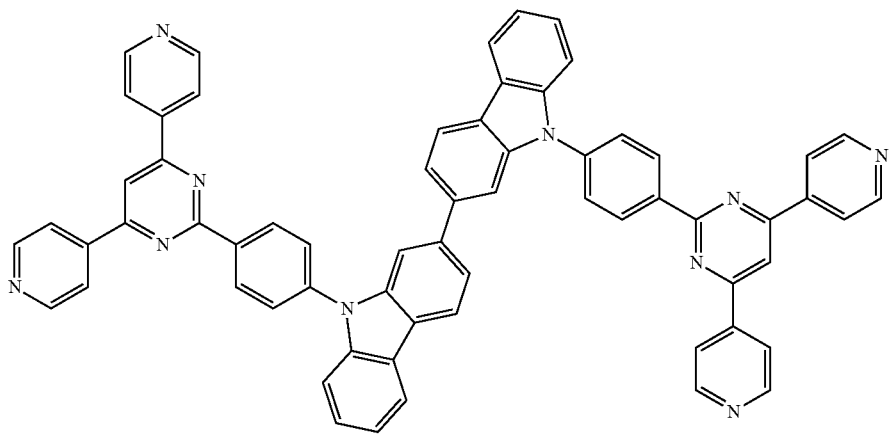
34
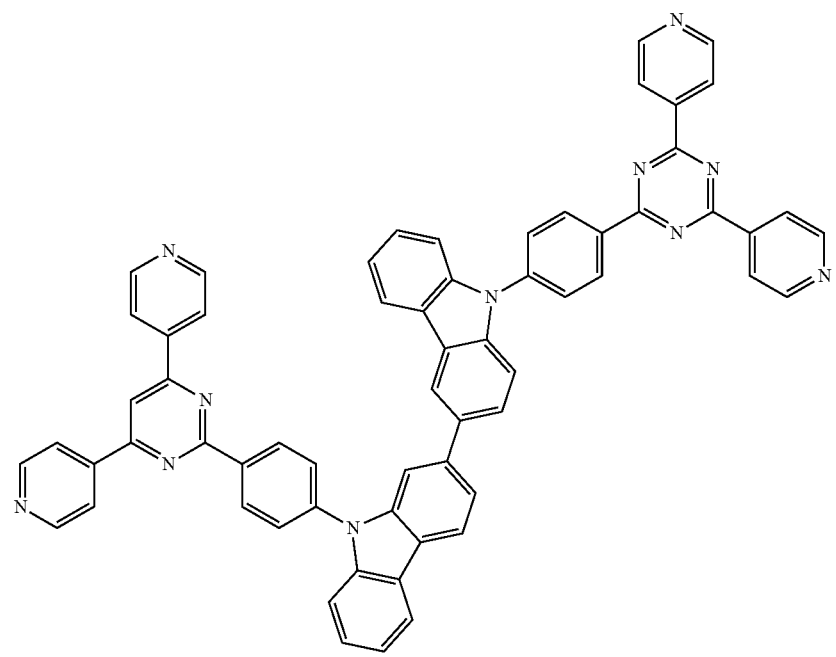

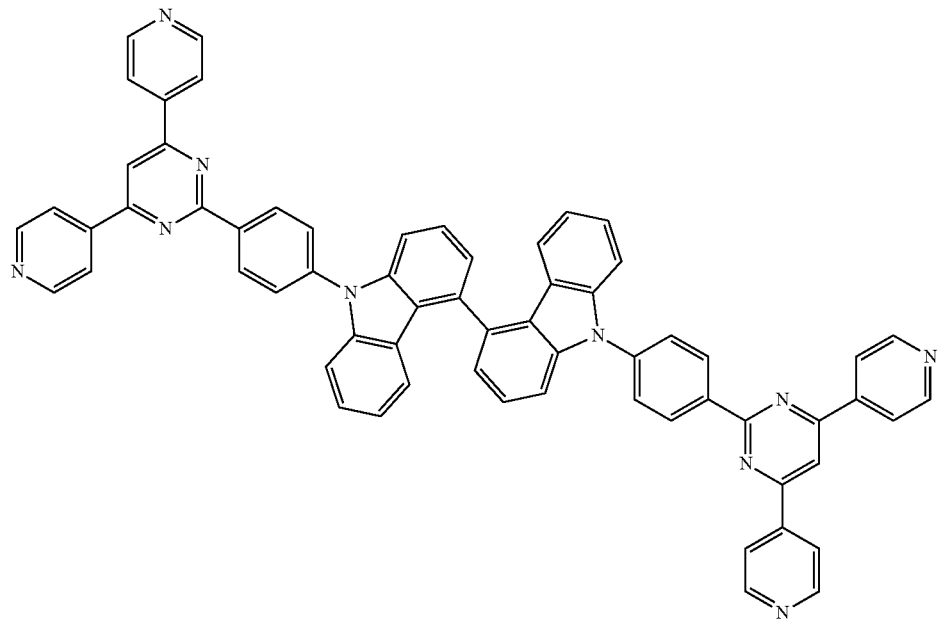
35
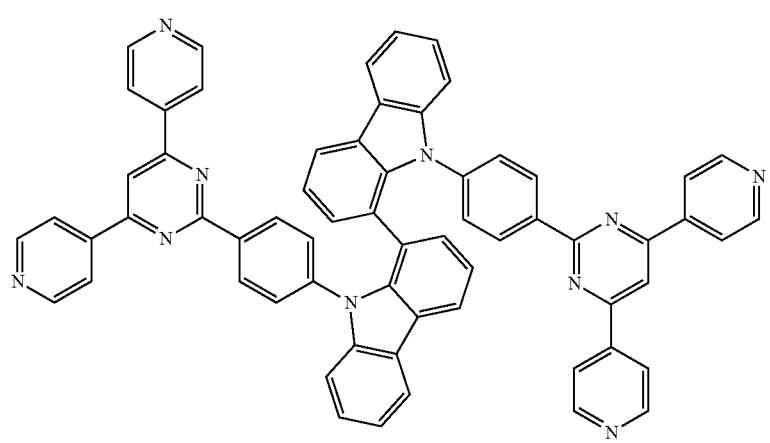
36
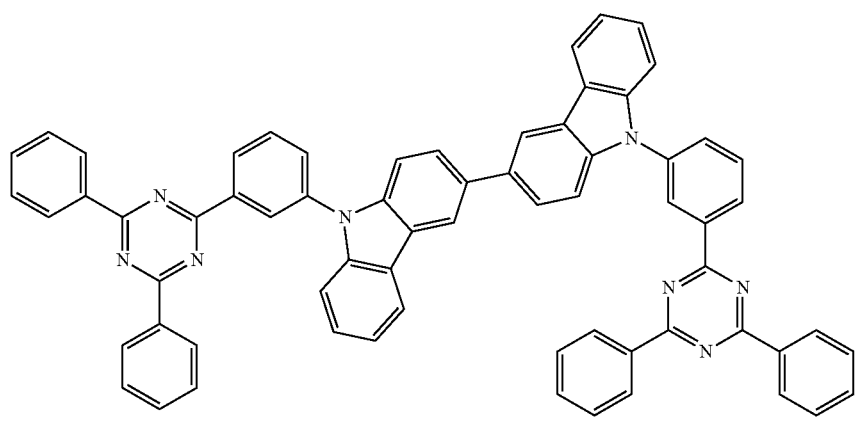
37

38
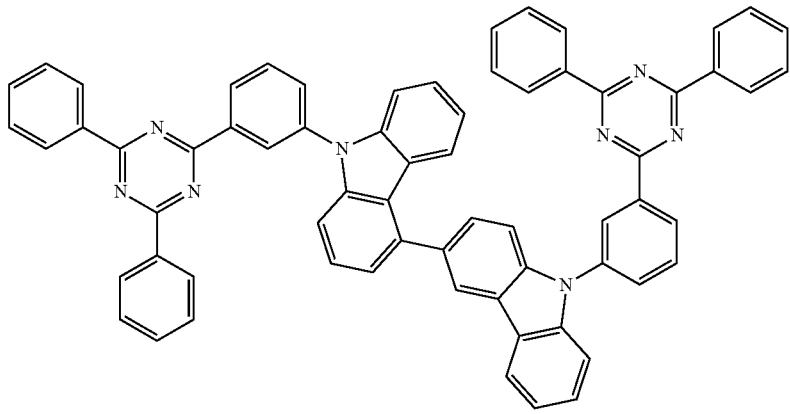
39
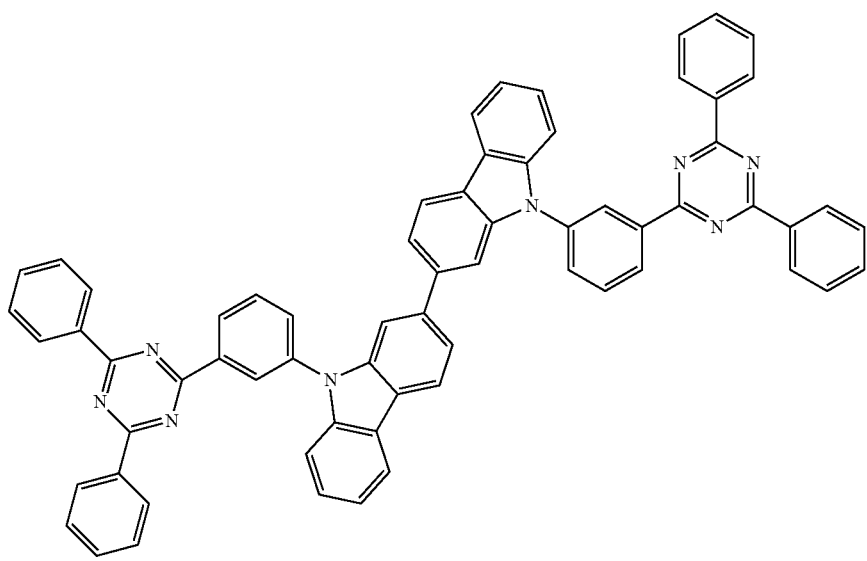
40
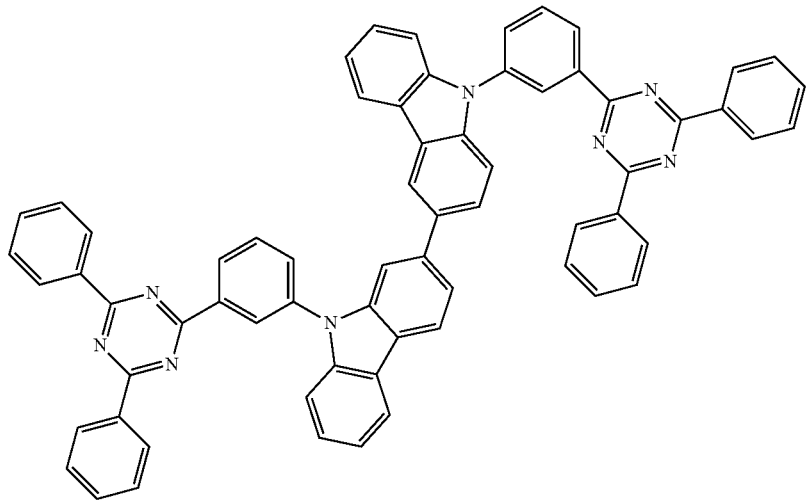

41
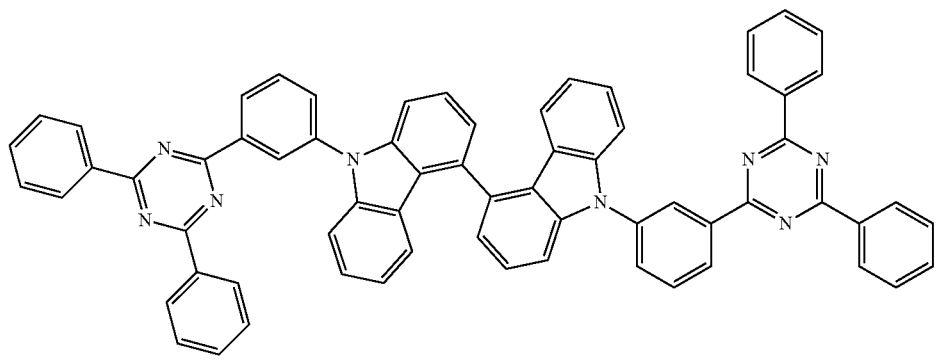
42
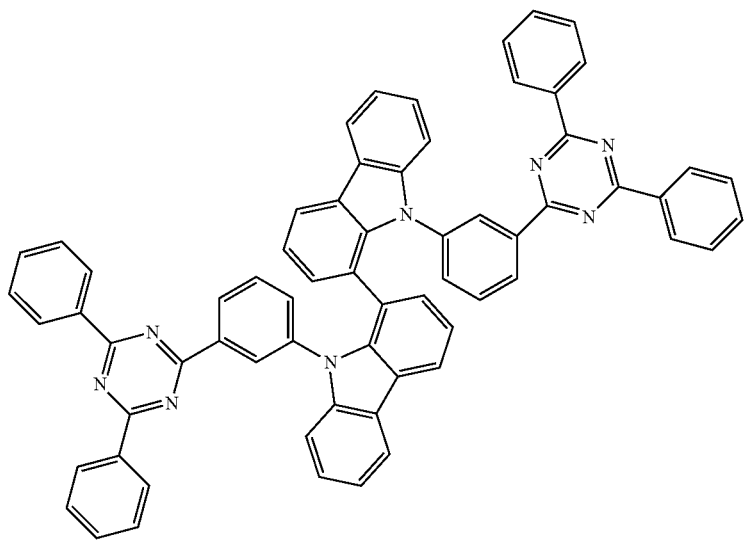
43 44
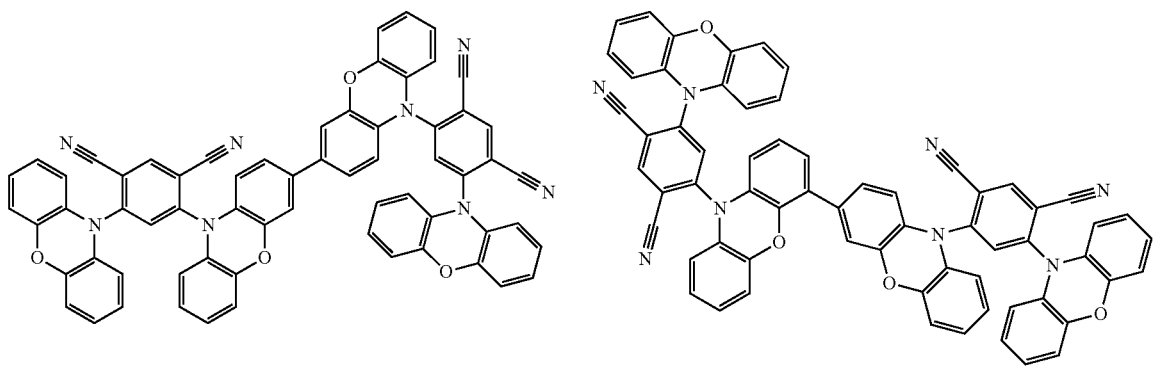
45 46
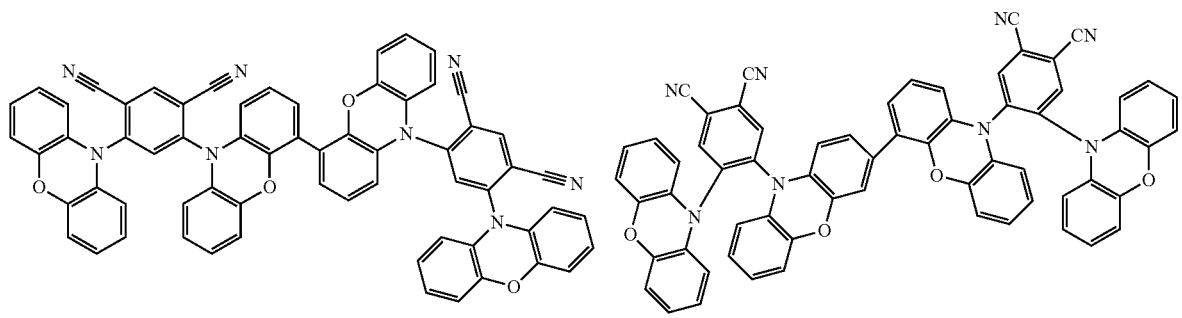

-continued
47
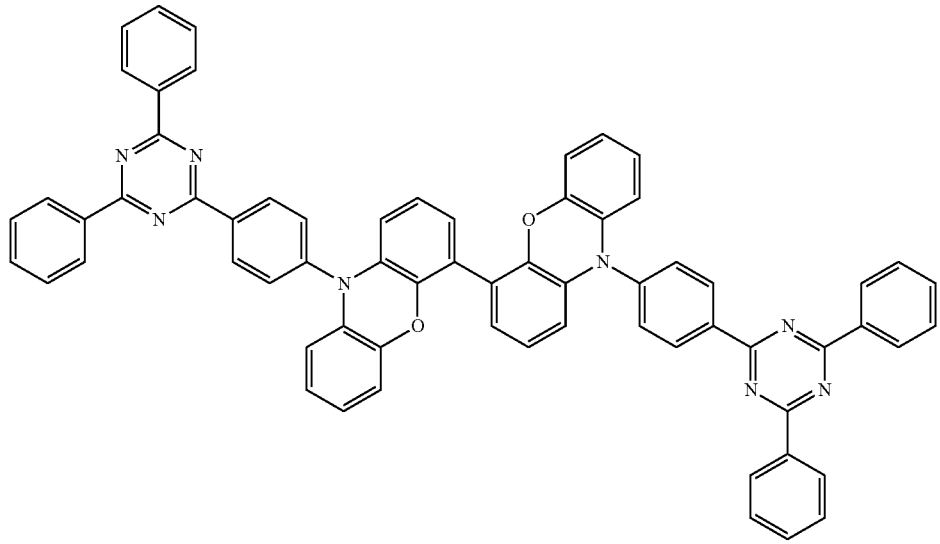
48
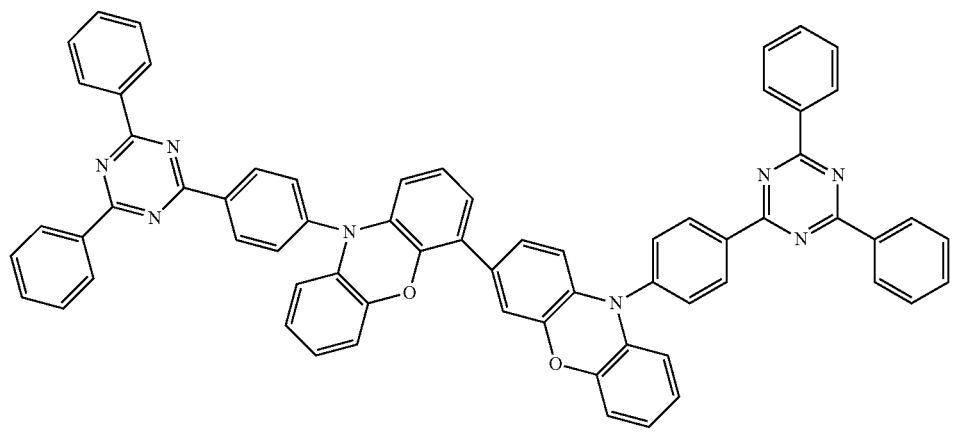
49
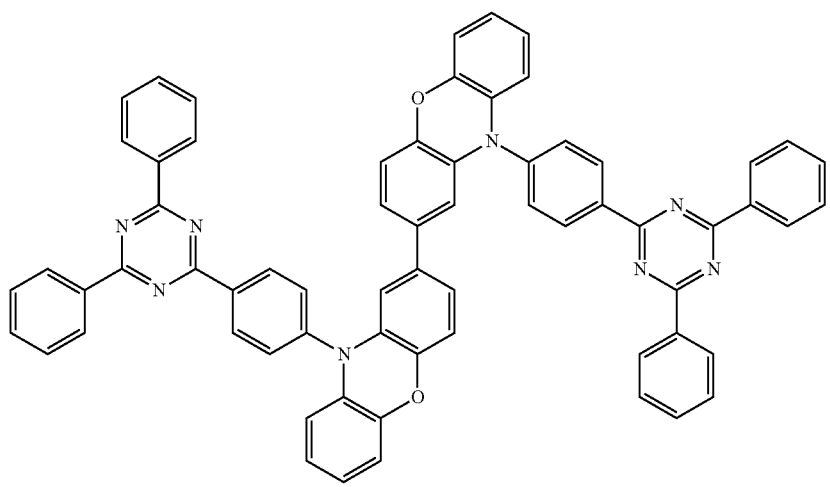

50
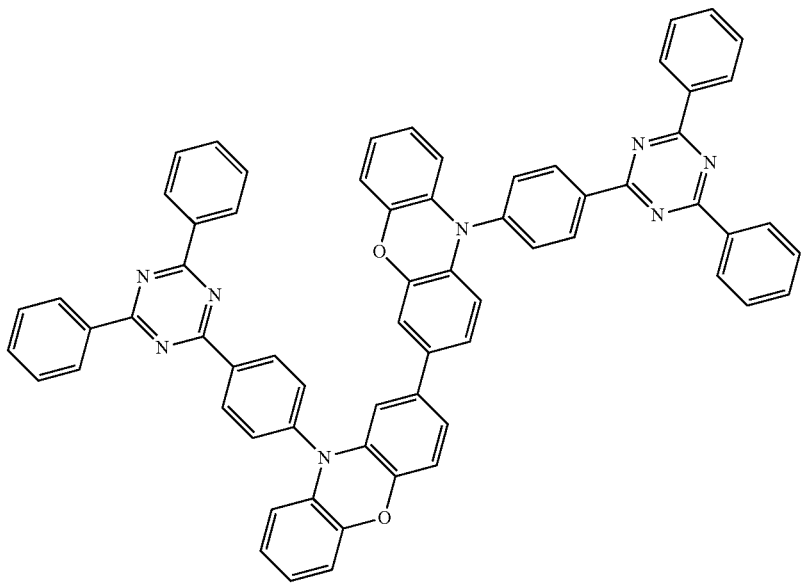
51
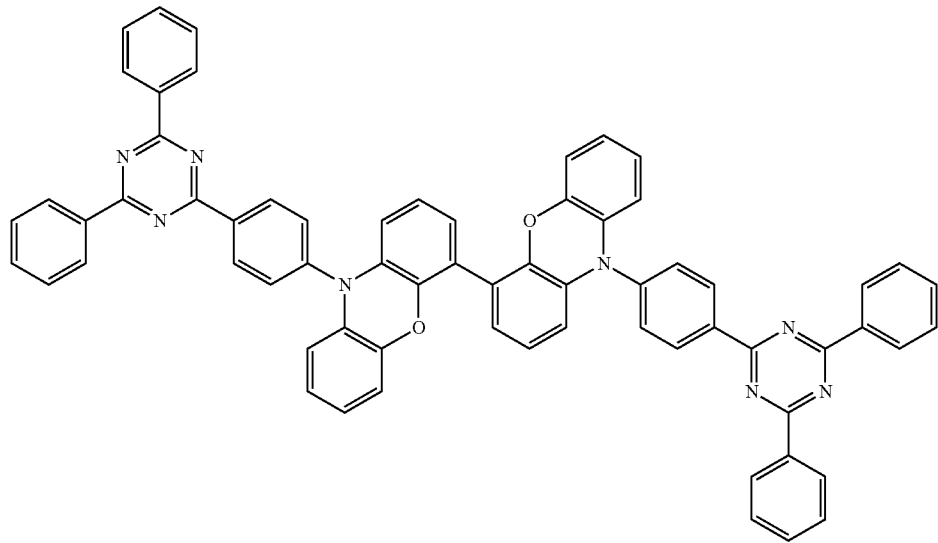
52 53
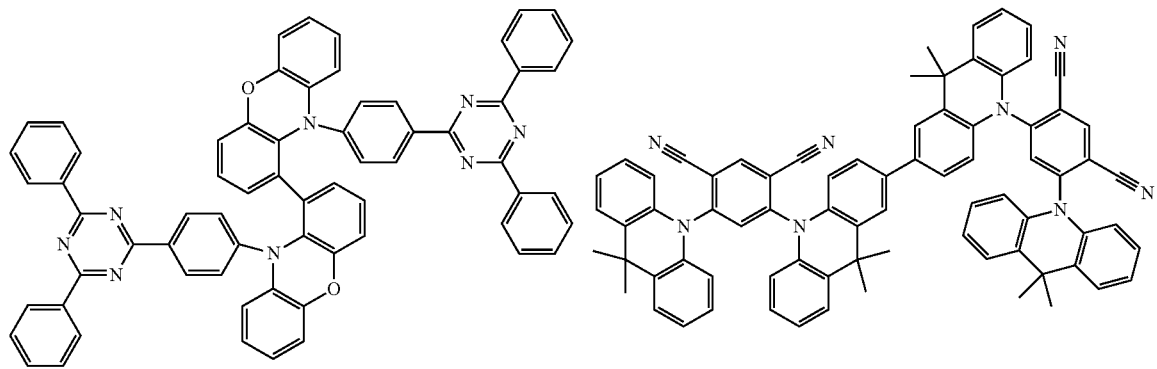

-continued
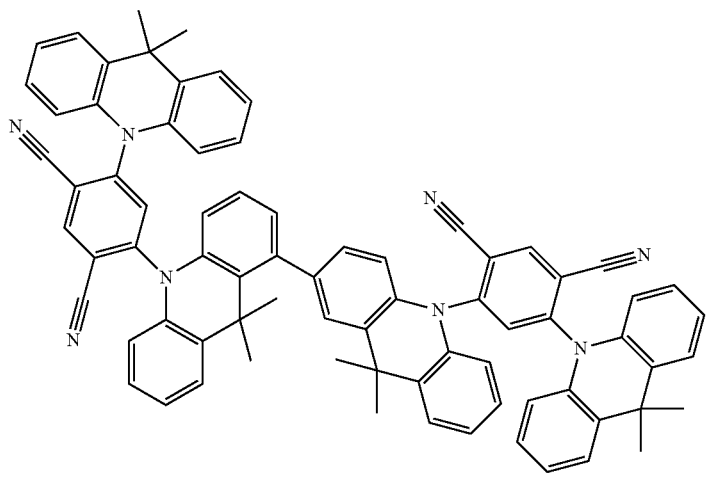
54
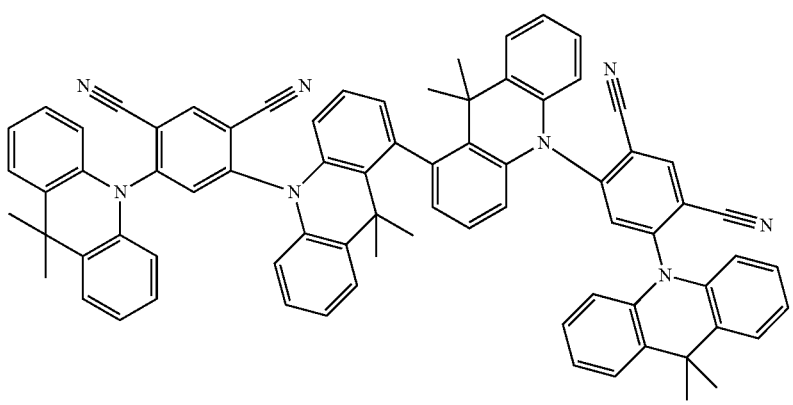
55
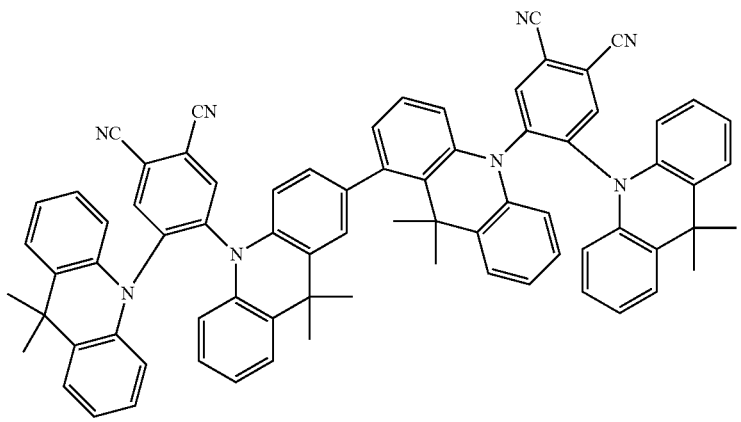
56

57
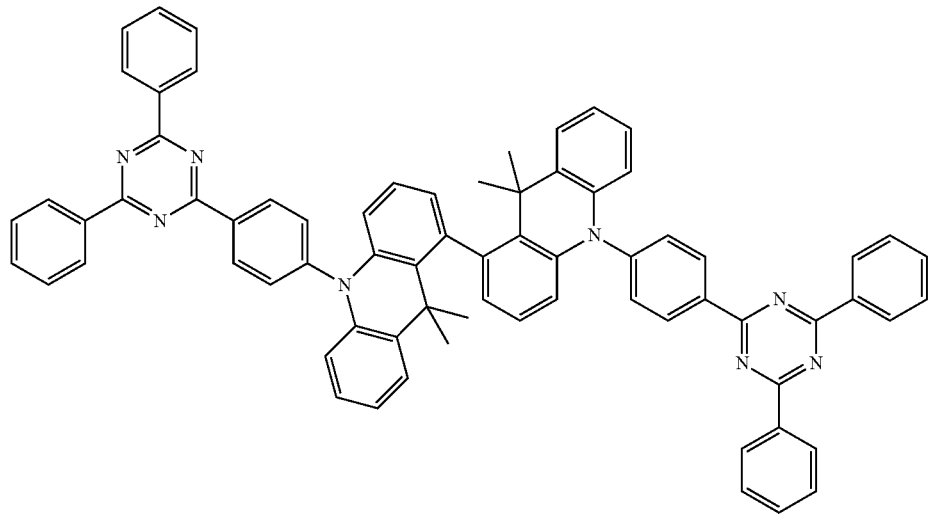
58
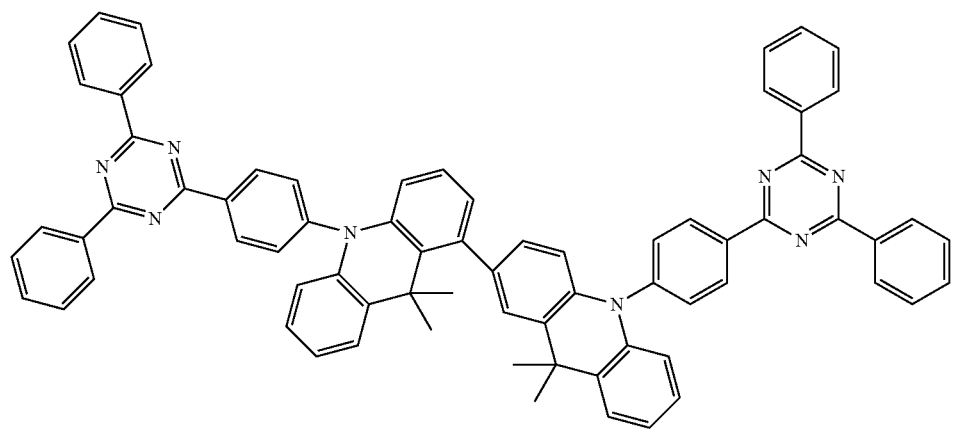
59
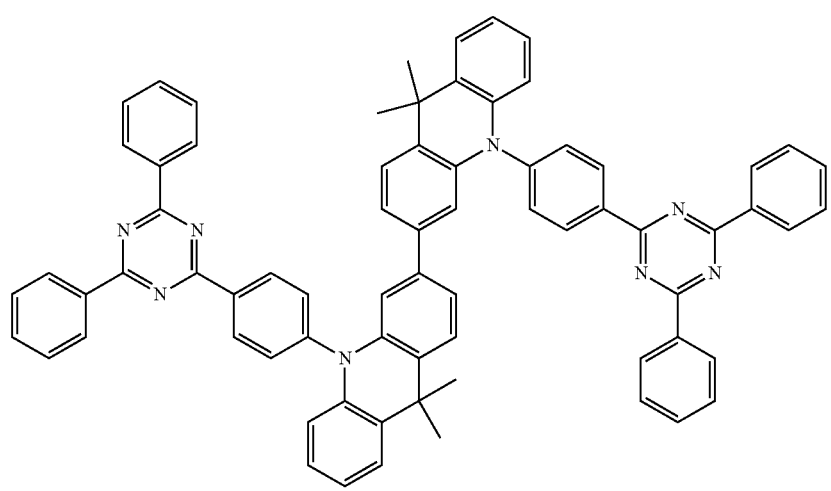

-continued
60
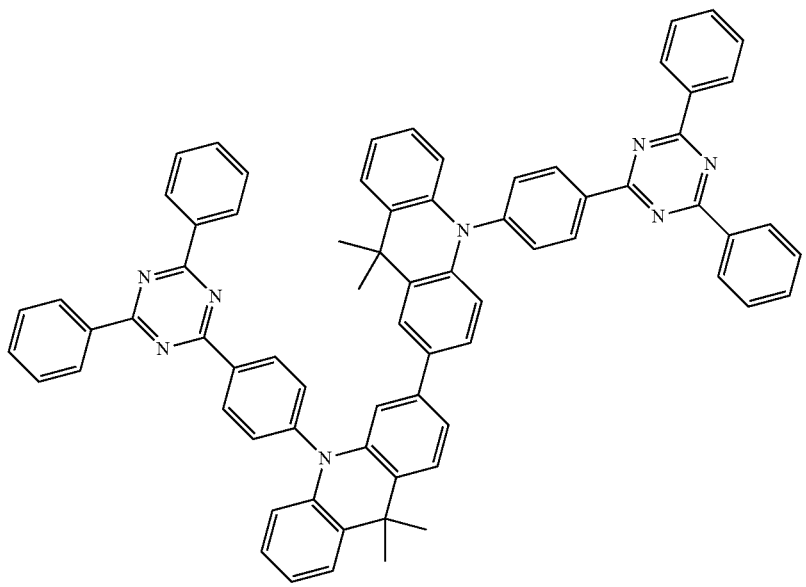
61
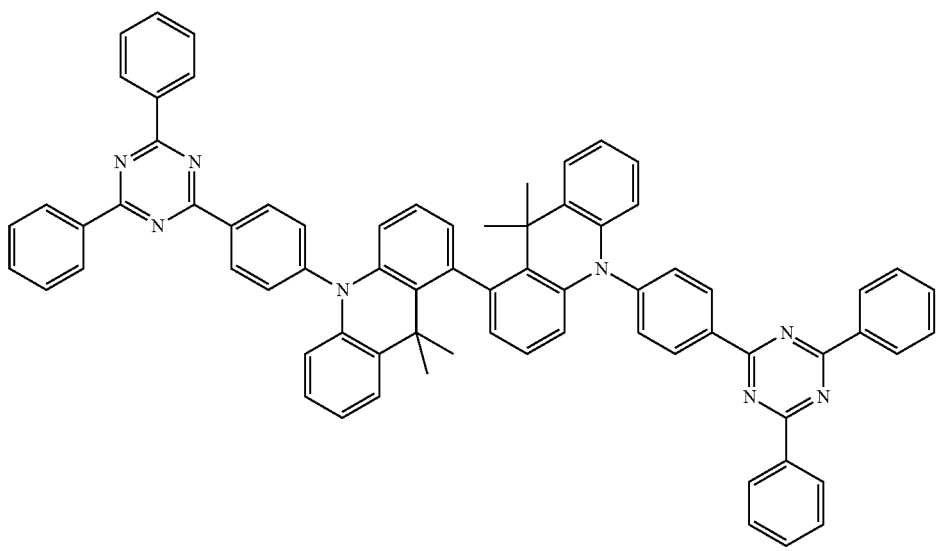
62 63
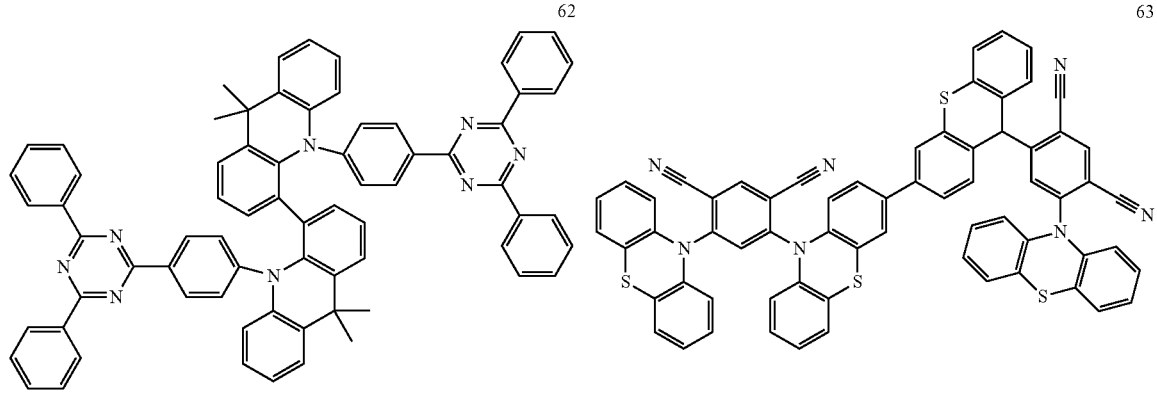

64
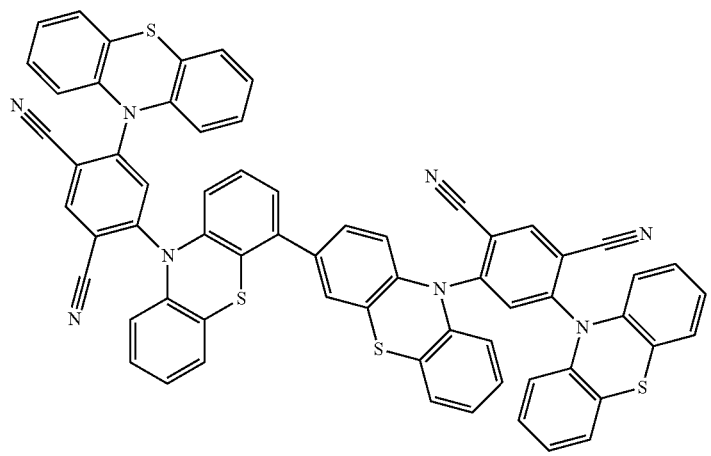
65
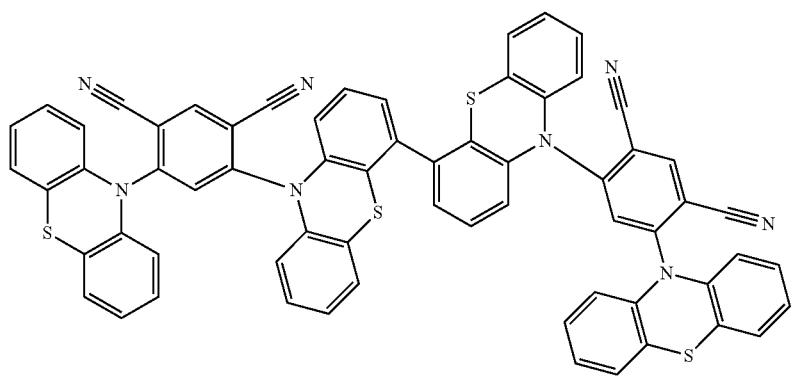
66
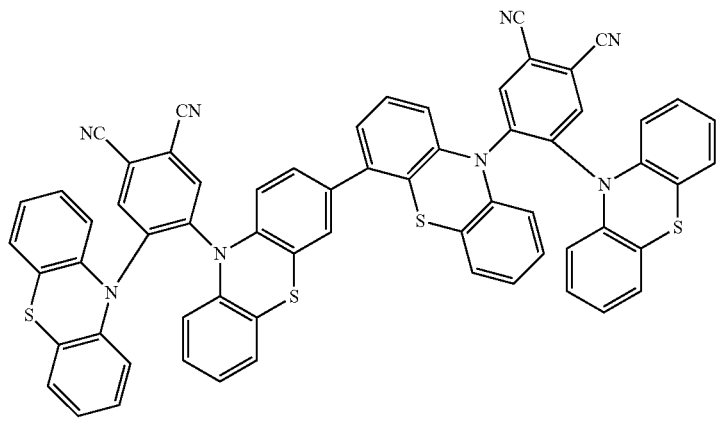

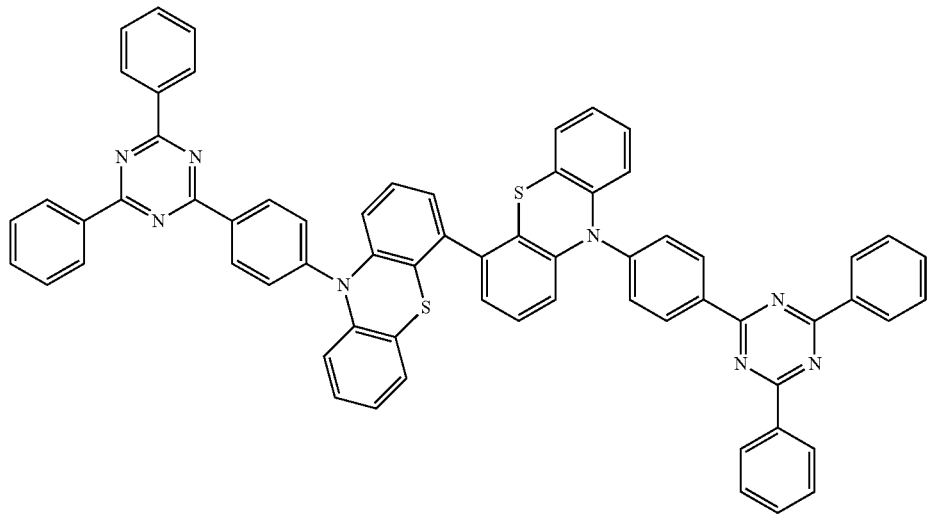
67
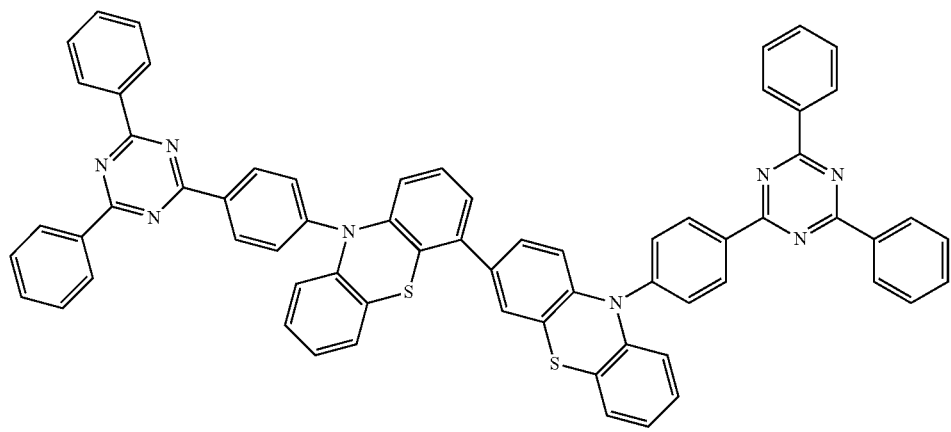
68
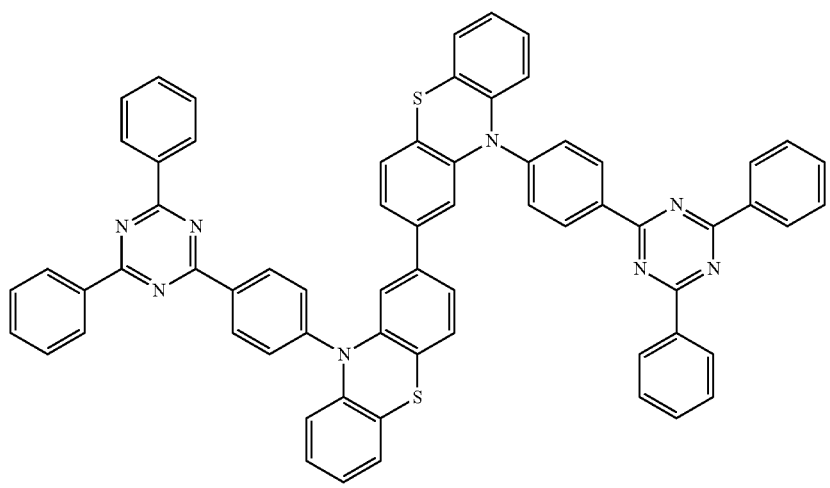
69

70
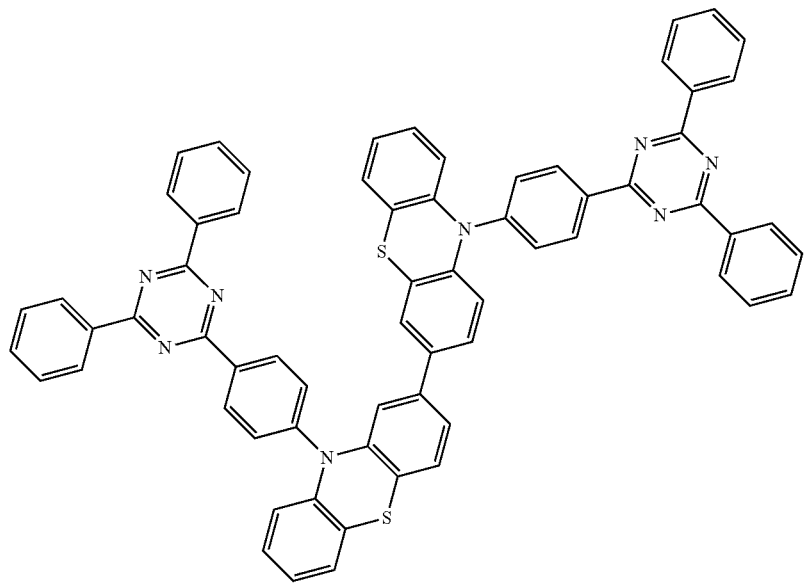
71
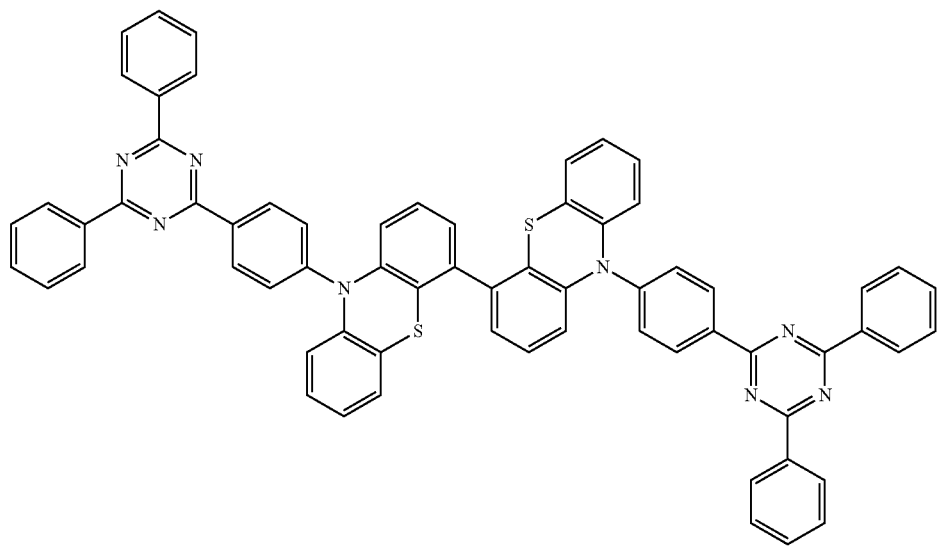
72
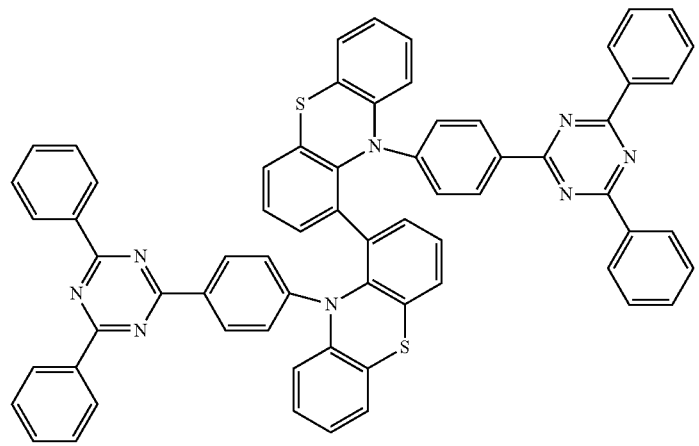

-continued
73
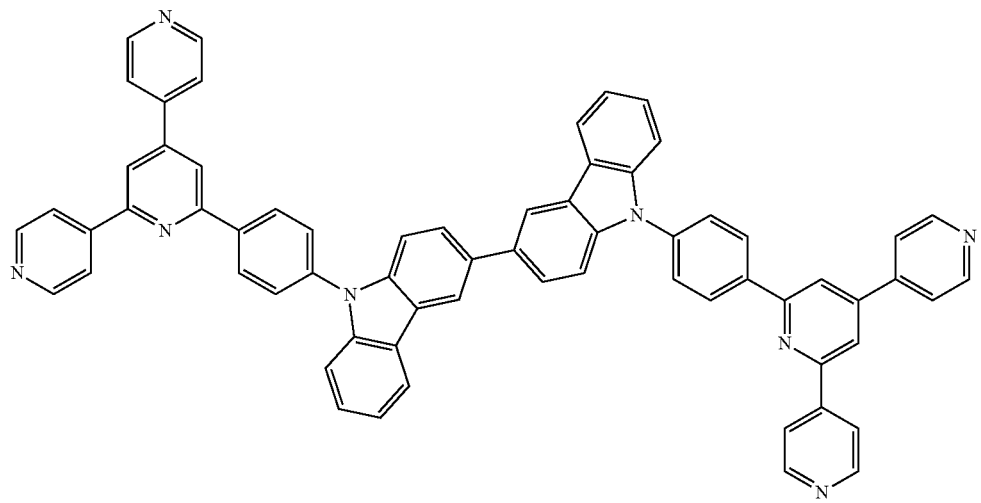
74
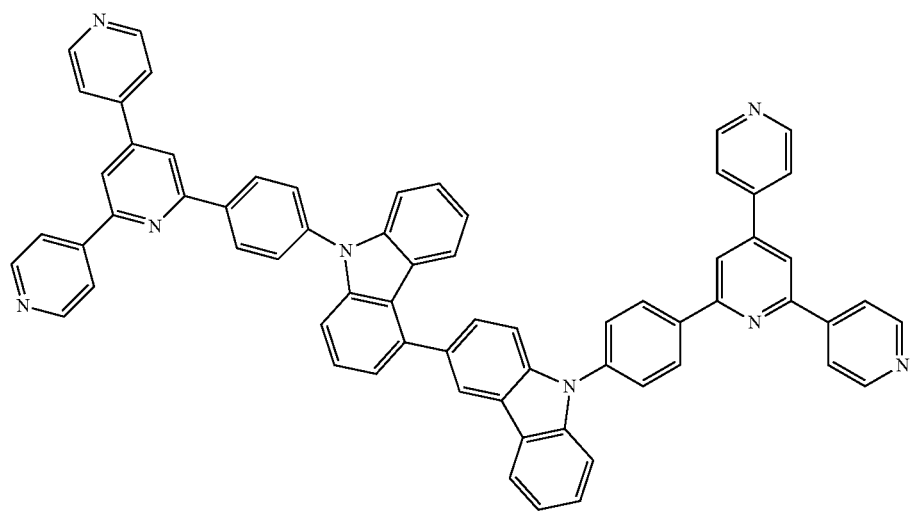
75
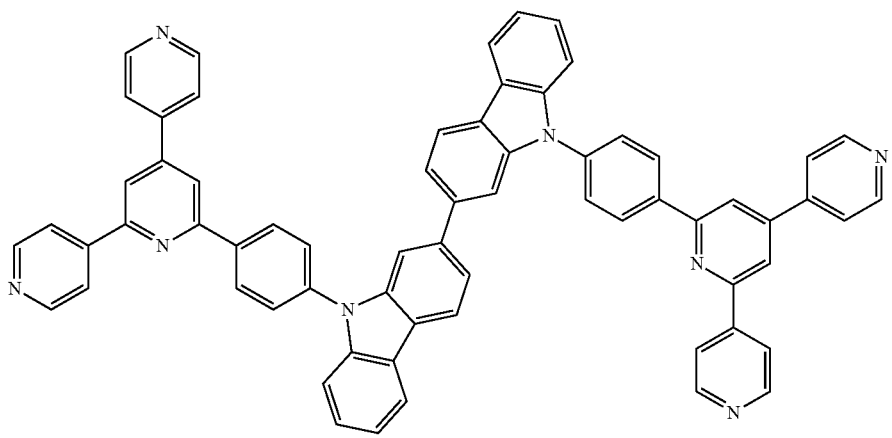

76
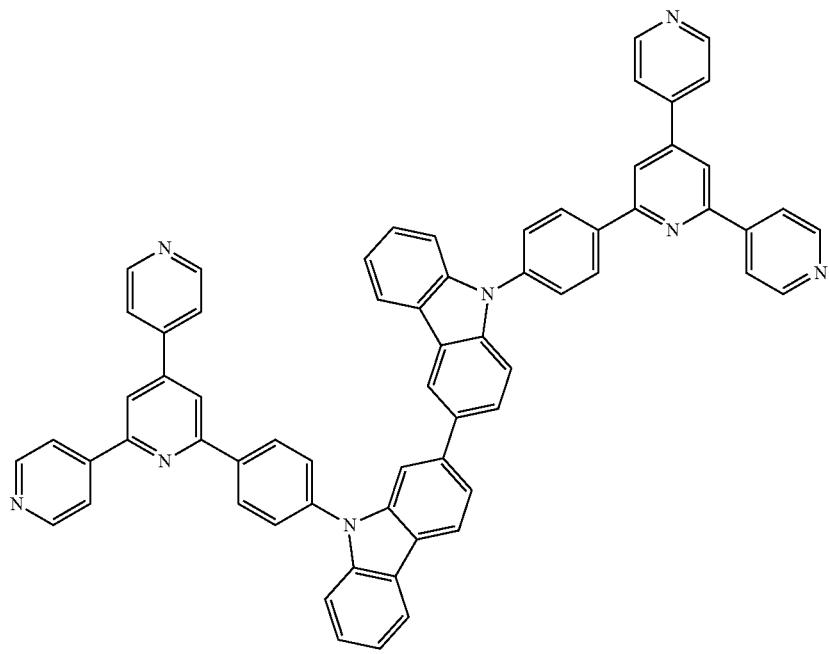
77
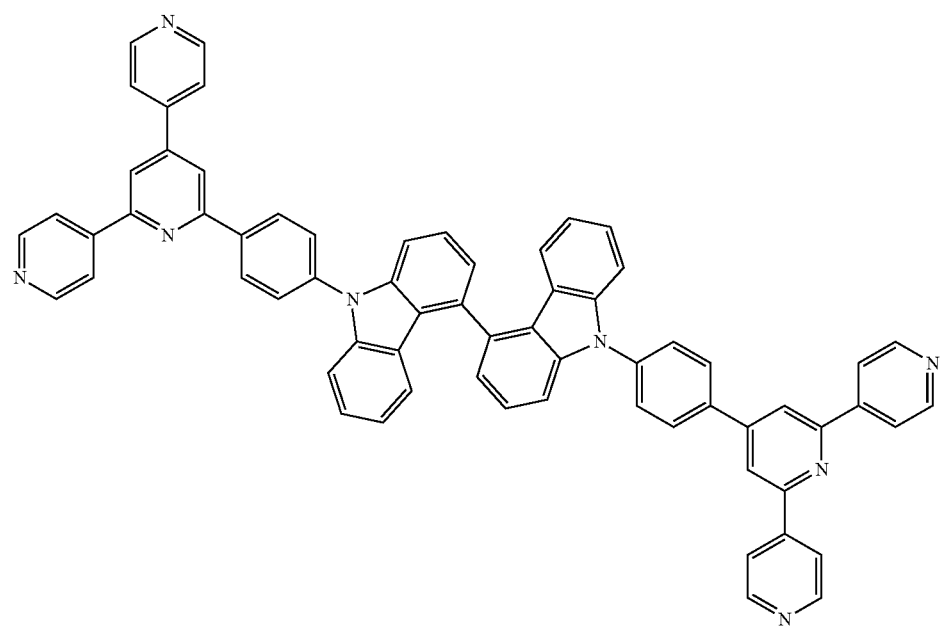

-continued
78
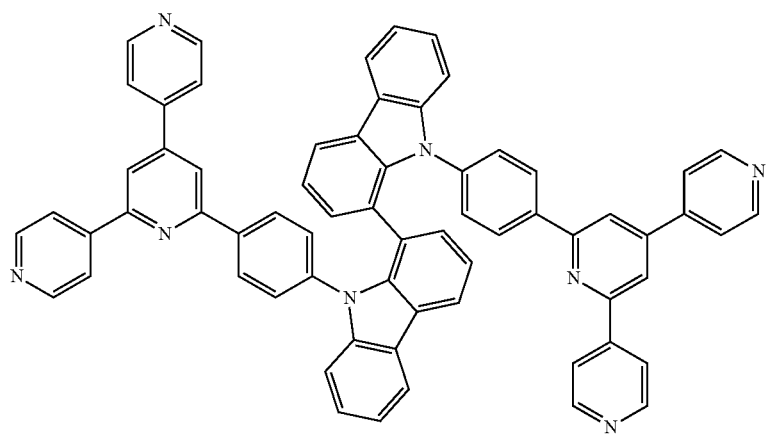
79
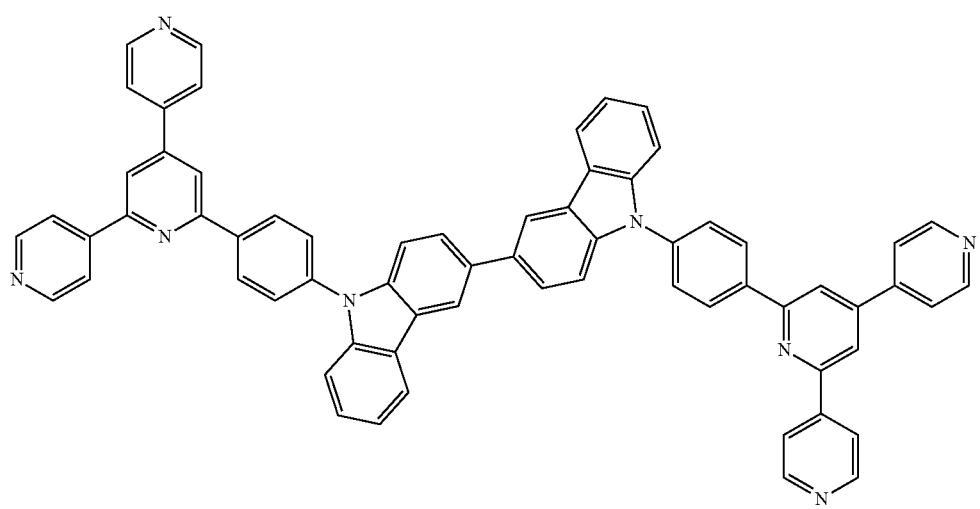
80
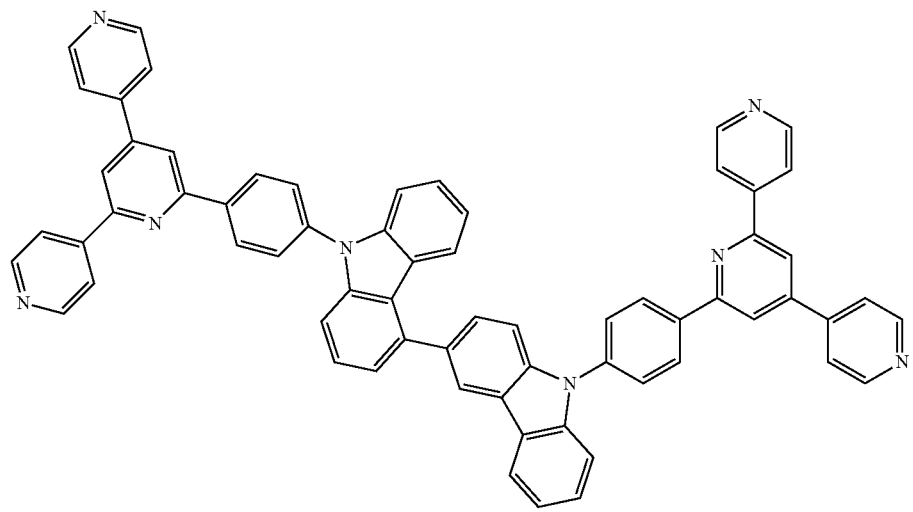

81
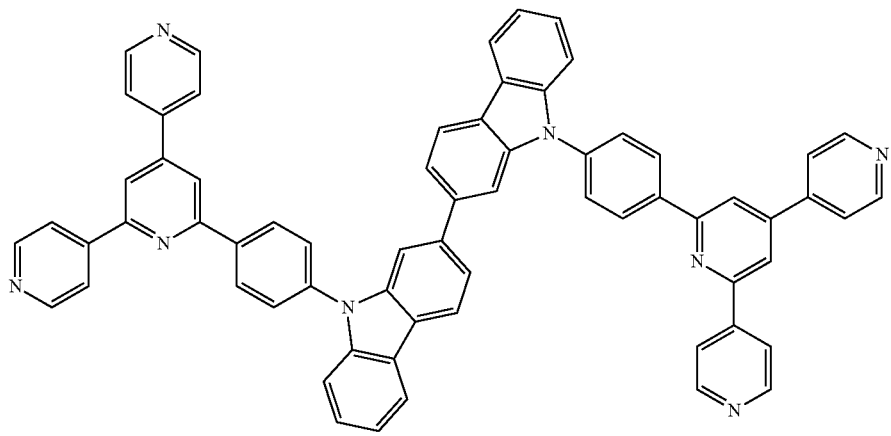
82
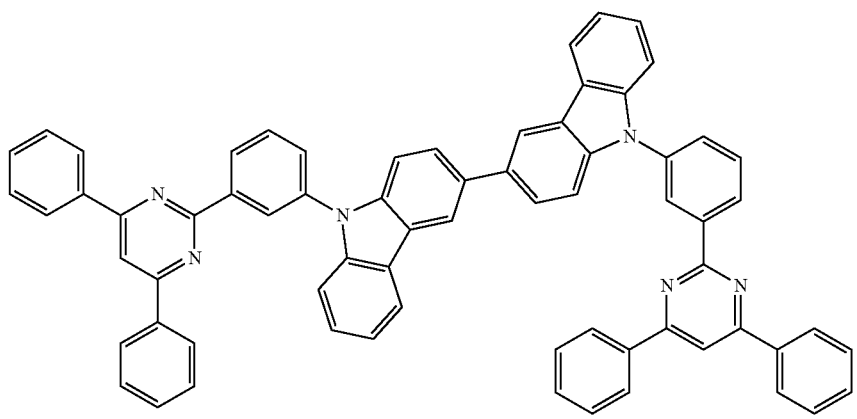
83
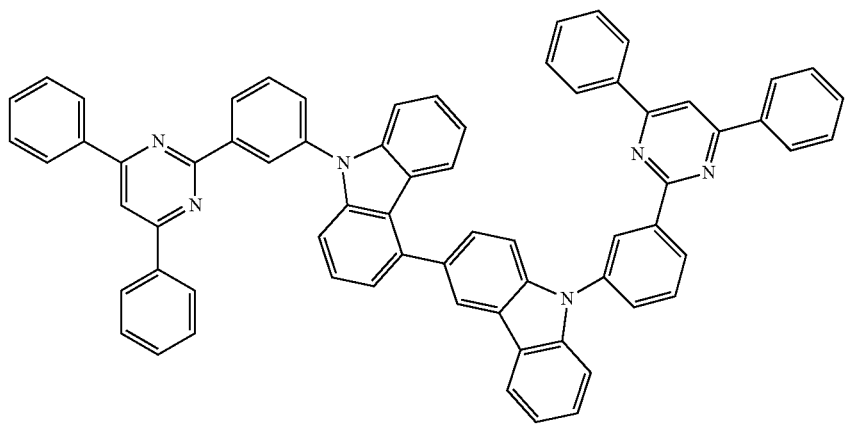

84
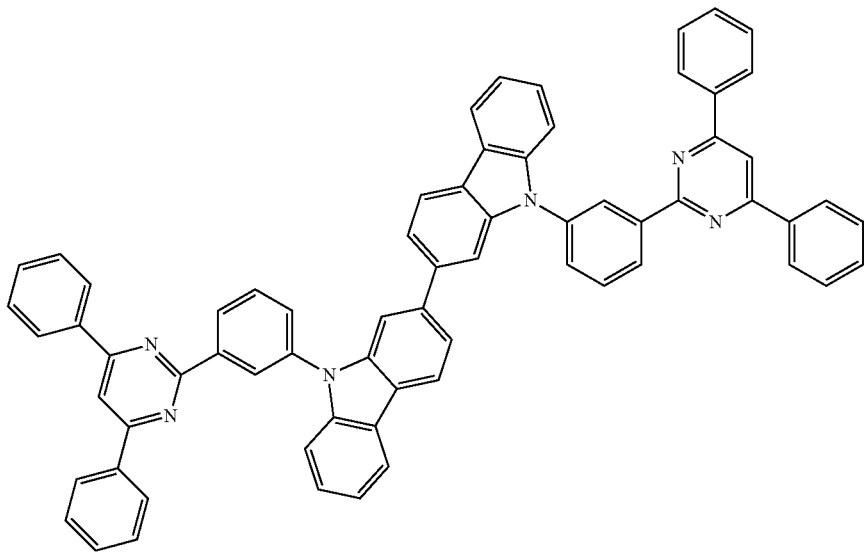
85
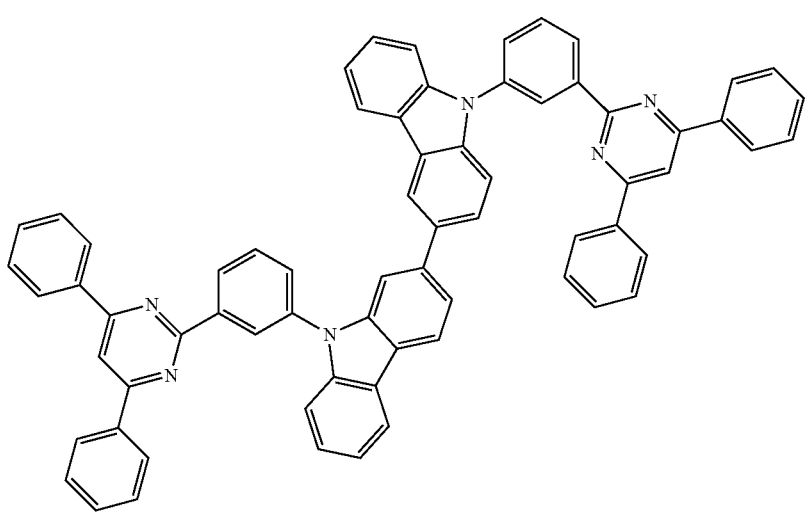
86
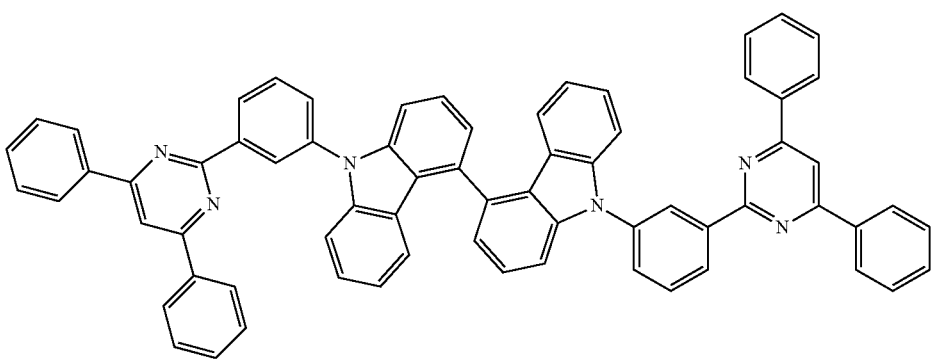

87
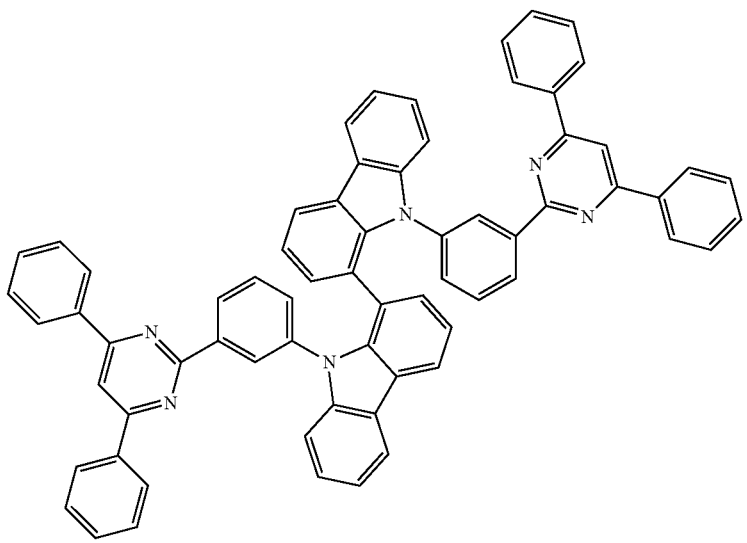
88
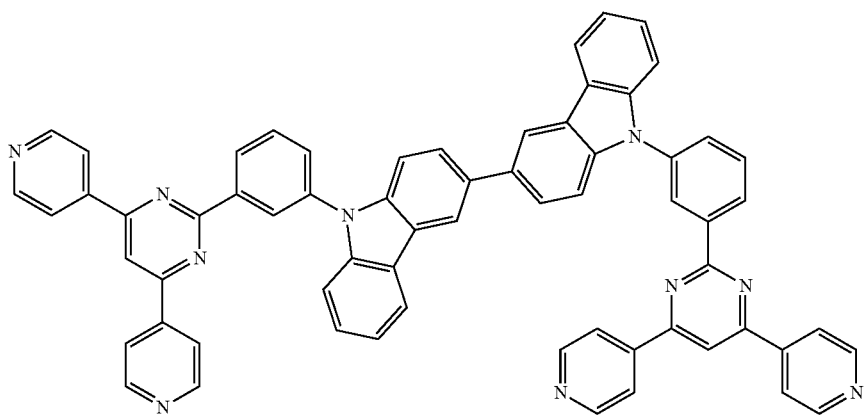
89
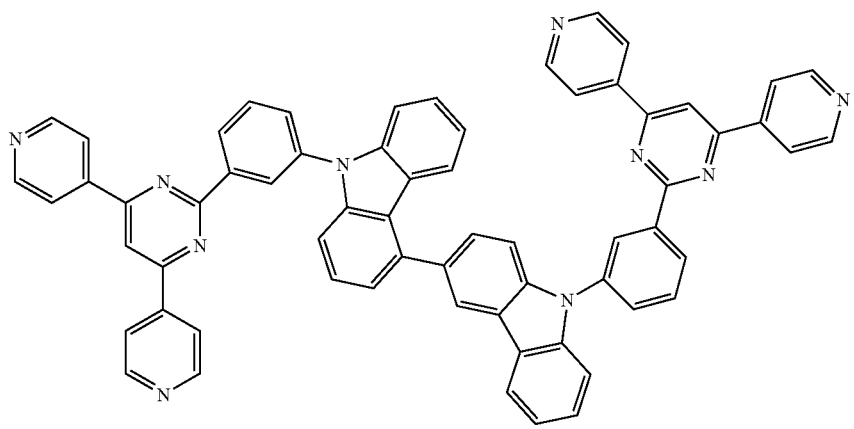

-continued
90
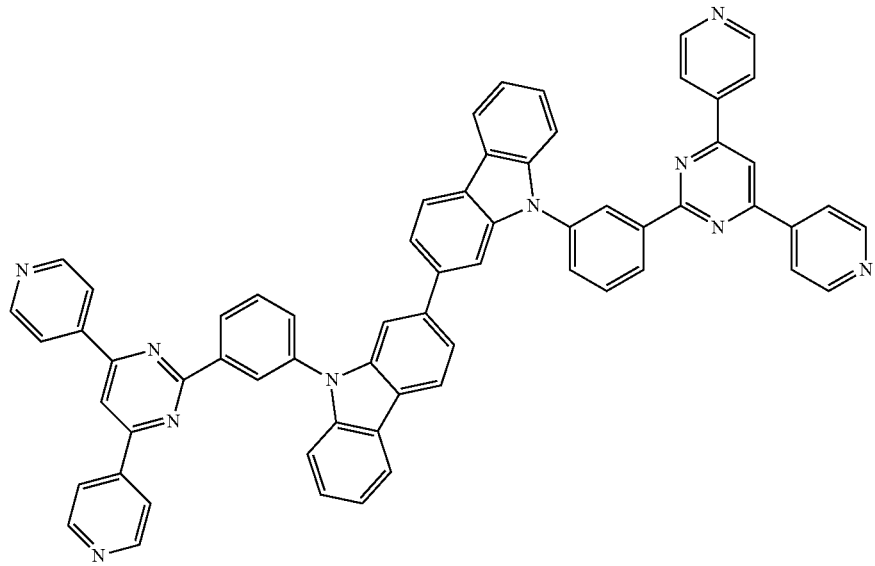
91
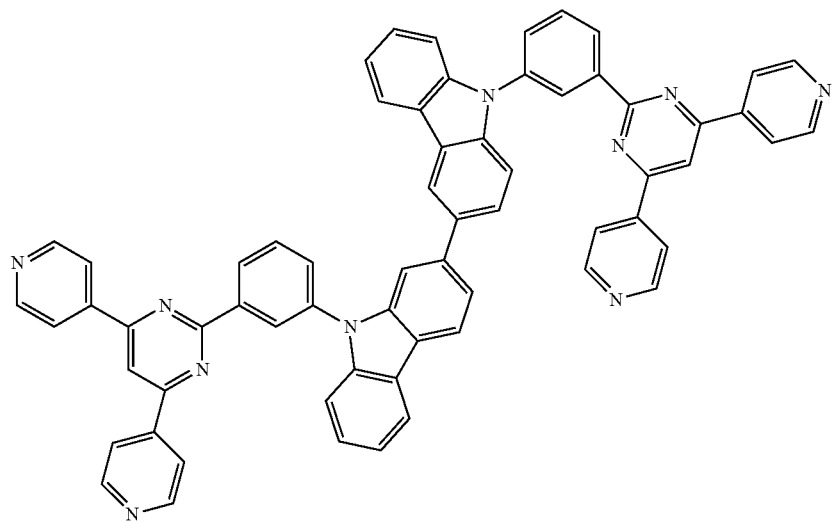
92
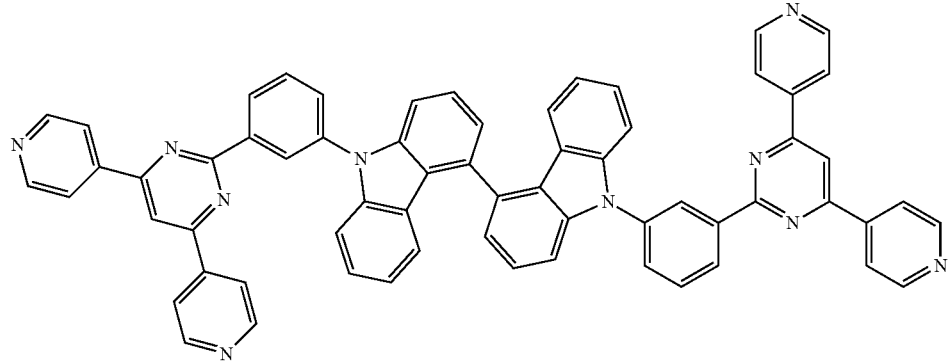

-continued

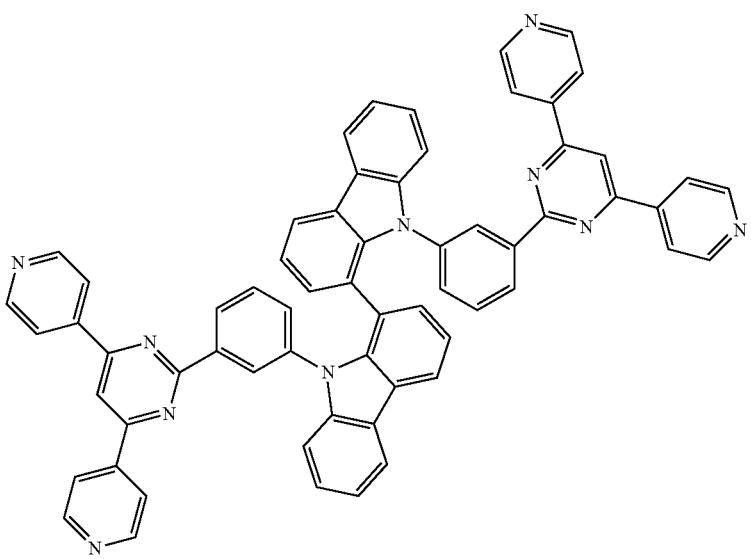

93

Hereinafter, an organic optoelectronic diode including the dopant is described.

The organic optoelectronic device may be any device to convert electrical energy into photoenergy and vice versa without particular limitation, and may be, for example an organic photoelectric device, an organic light emitting diode, an organic solar cell, and an organic photo conductor drum.

The organic optoelectronic device may include an anode and a cathode facing each other, at least one organic layer between the anode and the cathode, and the organic layer includes at least one host and the dopant.

Herein, an organic light emitting diode as one example of an organic optoelectronic device is described referring to drawings.

FIG. 1 is a cross-sectional view of an organic light emitting diode according to an embodiment.

Referring to FIG. 1, an organic light emitting diode 100 according to an embodiment includes an anode 110 and a cathode 120 and an organic layer 105 between the anode 110 and the cathode 120.

The anode 110 may be made of a conductor having a high work function to help hole injection, and may be for example a metal, a metal oxide and/or a conductive polymer. The anode 110 may be for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDT), polypyrrole, and polyaniline, but is not limited thereto.

The cathode 120 may be made of a conductor having a low work function to help electron injection, and may be for example a metal, a metal oxide and/or a conductive polymer. The cathode 120 may be for example a metal such as magnesium, calcium, sodium, potassium, titanium, indium, yttrium, lithium, gadolinium, aluminum silver, tin, lead, cesium, barium, and the like, or an alloy thereof; a multilayer structure material such as LiF/Al, $LiO_2$/Al, LiF/Ca, LiF/Al, and $BaF_2$/Ca, but is not limited thereto.

The organic layer 105 includes a light emitting layer 130 including at least one host and the dopant.

The host may be a single host or a mixed host including two or more. The host may be selected from material having a larger energy bandgap than the dopant.

The dopant is the same as described above and is mixed with a host and receives energy from the host to emit light in a specific wavelength region. As described above, the dopant may be a fluorescent dopant having high efficiency and color purity capable of replacing a phosphorescent dopant including a heavy metal.

The dopant may be included in a smaller amount than the host. For example, the dopant may be included in an amount of about 0.01 to 40 wt %, within the range about 0.01 to 30 wt %, and within the range about 0.01 to 20 wt % based on a total amount of the host and the dopant.

The organic layer 105 may be formed using a dry film formation method or a solution process. The dry film formation method may be for example a chemical vapor deposition (CVD) method, sputtering, plasma plating, and ion plating, and two or more compounds may be simultaneously formed into a film or compound having the same deposition temperature may be mixed and formed into a film. The solution process may be for example inkjet printing, spin coating, slit coating, bar coating and/or dip coating.

Figure 2:
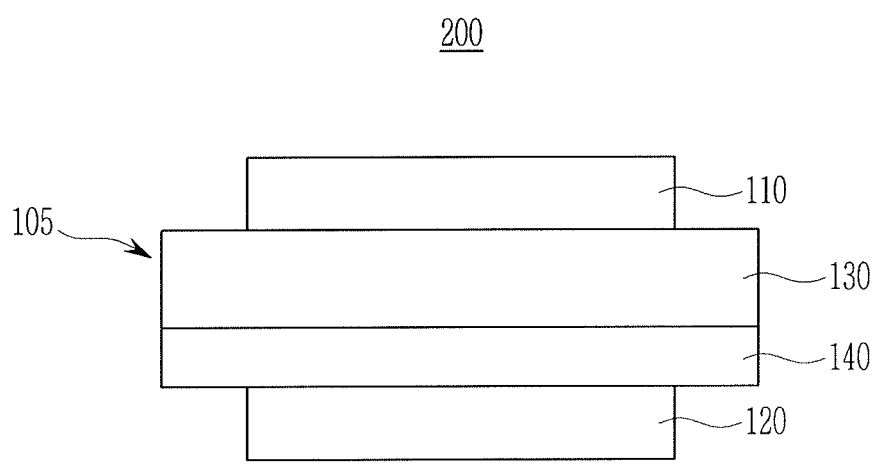
FIG. 2 is a cross-sectional view of an organic light emitting diode according to another embodiment.

FIG. 2 is a cross-sectional view of an organic light emitting diode according to another embodiment.

Referring to FIG. 2, an organic light emitting diode 200 of the present embodiment includes an anode 110 and a cathode 120 and an organic layer 105 disposed between the anode 110 and the cathode 120 like the embodiment.

The organic layer 105 includes a light emitting layer 130 and an auxiliary layer 140 disposed between the light emitting layer 130 and the cathode 120. The auxiliary layer 140 may facilitate injection and transport of charge carriers between the cathode and the light emitting layer 130. The auxiliary layer 140 may be for example an electron transport layer, an electron injection layer, and/or an electron transport auxiliary layer.

In FIGS. 1 and 2, the organic layer 105 may further include at least one auxiliary layer disposed between the anode 110 and the light emitting layer 130.

The organic light emitting diode may be applied to an organic light emitting diode display.

Hereinafter, the embodiments are illustrated in more detail with reference to examples. These examples, however, are not in any sense to be interpreted as limiting the scope of the invention.

Synthesis of Intermediate

Synthesis of Intermediate I-1

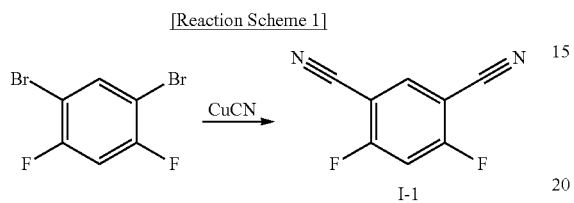

1,5-dibromo-2,4-difluorobenzene (5 g, 18.4 mmol) and copper (I) cyanide (CuCN) (4.9 g, 55.2 mmol) were added to dimethylformamide (90 ml), and the mixture was stirred under a nitrogen flow. Subsequently, the solution was heated up, refluxed and stirred for 14 hours, cooled down to room temperature, and filtered, and the filtered solution was treated with magnesium sulfate by using dichloromethane to remove moisture and purified through a column to obtain Intermediate I-1 (2.4 g). A yield was 80%.

Synthesis of Intermediate I-2

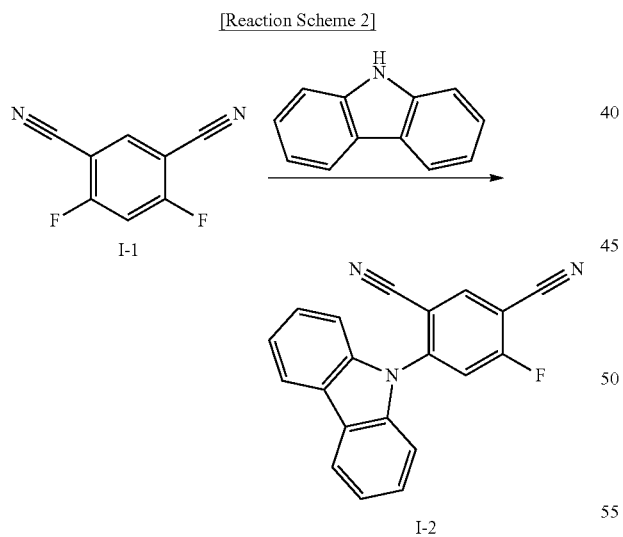

Sodium hydride (0.29 g, 7.2 mmol) was three times washed with hexane and dried udder vacuum for 2 hours. Subsequently, tetrahydrofuran (30 ml) was added thereto, and 30 minutes later, 9H-carbazole (1 g, 6.0 mmol) was added thereto. After minutes, Intermediate I-1 (0.98 g, 6.0 mmol) was added thereto. The solution was stirred at room temperature for 10 hours and then, treated with magnesium sulfate by using dichloromethane to remove moisture and wet-purified through a column to obtain Intermediate I-2 (0.7 g). A yield was 37%.

Synthesis of Intermediate I-3

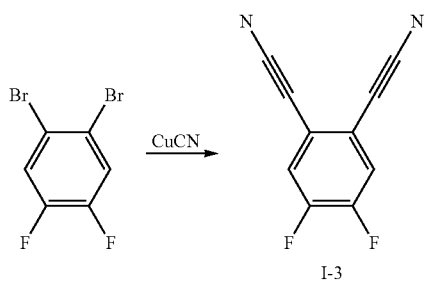

1,2-dibromo-4,5-difluorobenzene (5 g, 18.4 mmol) and copper (I) cyanide (CuCN) (4.9 g, 55.2 mmol) were added to dimethylformamide (90 ml), and the mixture was stirred under a nitrogen flow. Subsequently, the solution was heated up, refluxed and stirred for 14 hours, and cooled down to room temperature. After filtering a precipitate produced therein, the filtered solution was treated with magnesium sulfate by using dichloromethane to remove moisture and wet-purified through a column to obtain Intermediate I-3 (2.5 g). A yield was 83%.

Synthesis of Intermediate I-4

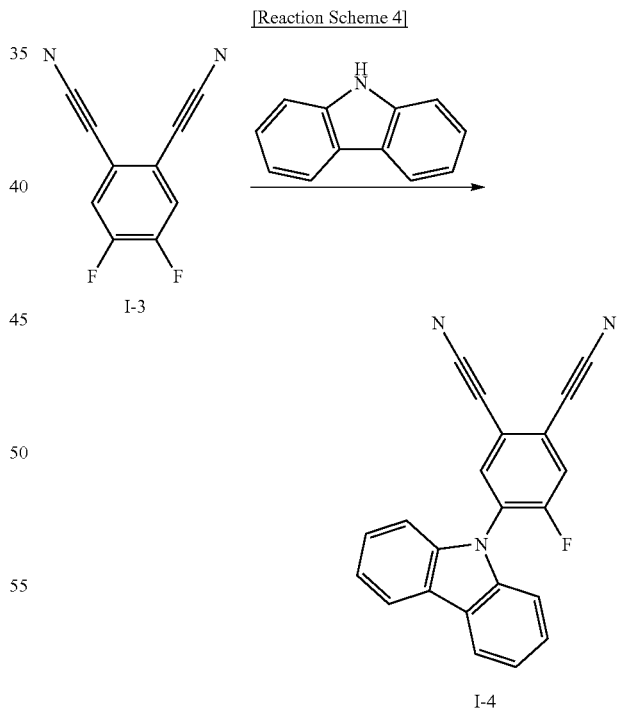

Sodium hydride (0.29 g, 7.2 mmol) was three times washed with hexane and then, dried under vacuum for 2 hours. Subsequently, tetrahydrofuran (30 ml) was added thereto, and after 30 minutes, 9H-carbazole (1 g, 6.0 mmol) was added thereto. After 10 minutes, Intermediate I-3 (0.98 g, 6.0 mmol) was added thereto. Subsequently, the solution was stirred at room temperature for 10 hours and treated with magnesium sulfate by using dichloromethane to remove moisture and wet-purified through a column to obtain Intermediate I-4 (0.6 g). A yield was 33%.

Synthesis of Intermediate I-5

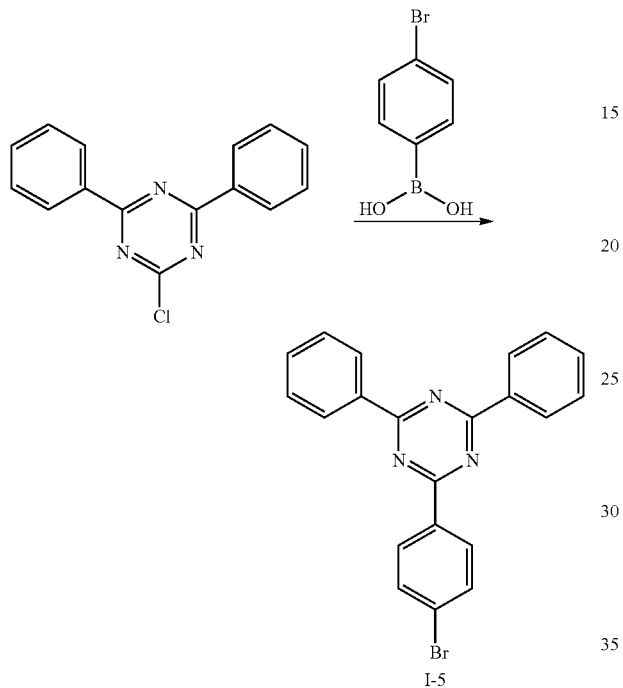

2-chloro-4,6-diphenyl-1,3,5-triazine (5 g, 18.6 mmol) and (4-bromophenyl)boronic acid (4.88 g, 24.3 mmol) were added to tetrahydrofuran (80 ml), and 2 M potassium carbonate (40 ml) was added thereto. Subsequently, tetrakis (triphenylphosphine)palladium (0) (0.65 g, 0.6 mmol) was added thereto, and the obtained mixture was heated up, refluxed and stirred for 3 hours, and cooled down to room temperature. Subsequently, a precipitate therein was filtered. The filtered precipitate was washed by using dichloromethane and hexane and then, purified through sublimation to obtain Intermediate I-5 (3.7 g). A yield was 51%.

Synthesis of Intermediate I-6

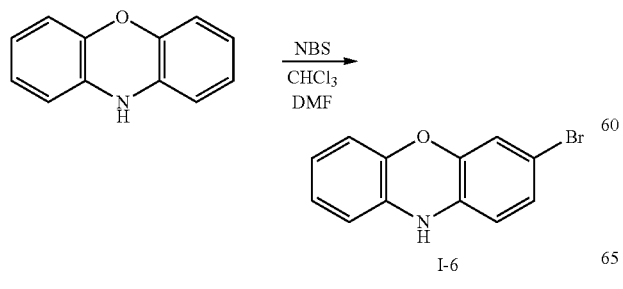

Phenoxazine (20 g, 109.16 mmol) was added to a mixed solution of a chloroform (200 ml) and dimethyl formamide (50 ml). N-bromosuccinimide (1 equivalent) was added thereto, and the obtained mixture was stirred at room temperature for 18 hours. Subsequently, a 1 M sodium thiosulfate solution (100 mL) was added to the reaction solution to separate layers, and an organic layer was separated therefrom. The organic layer was concentrated, and the concentrated residue was purified through silica gel column by using hexane and ethylacetate as an eluting solvent to obtain Intermediate I-6 (12.8 g).

Synthesis of Intermediate I-7

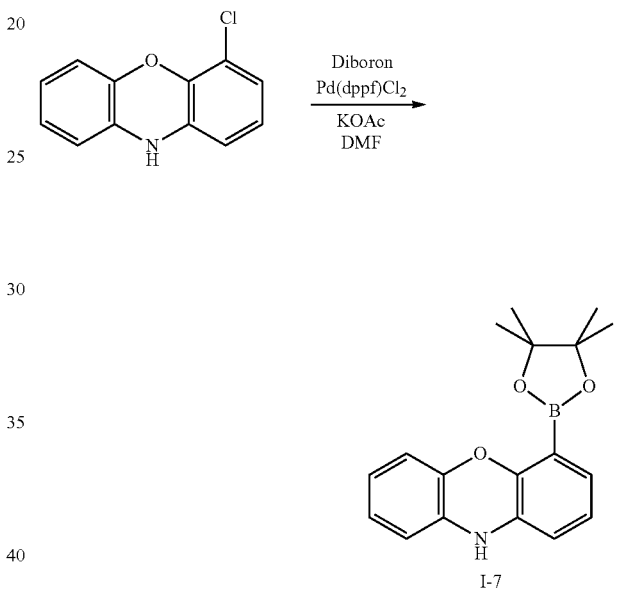

4-chlorophenoxazine (20 g, 91.89 mmol), bispinacolato diboron (1.2 equivalents), dichlorodiphenylphosphine palladium (0.05 equivalent), and potassium acetate (2 equivalent) were heated and refluxed for 19 hours. The reaction solution was cooled down and added to water (1.5 L) for solidification, and a solid precipitated therein was filtered. The solid was washed with water (500 mL) and methanol (500 mL). The washed solid was collected and then, recrystallized with a toluene ethylacetate solvent to obtain Intermediate 44-3 (24 g).

Synthesis of Intermediate I-8

[Reaction Scheme 8]

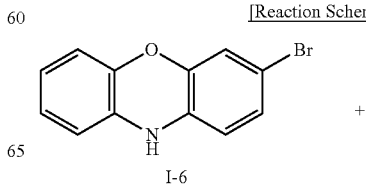

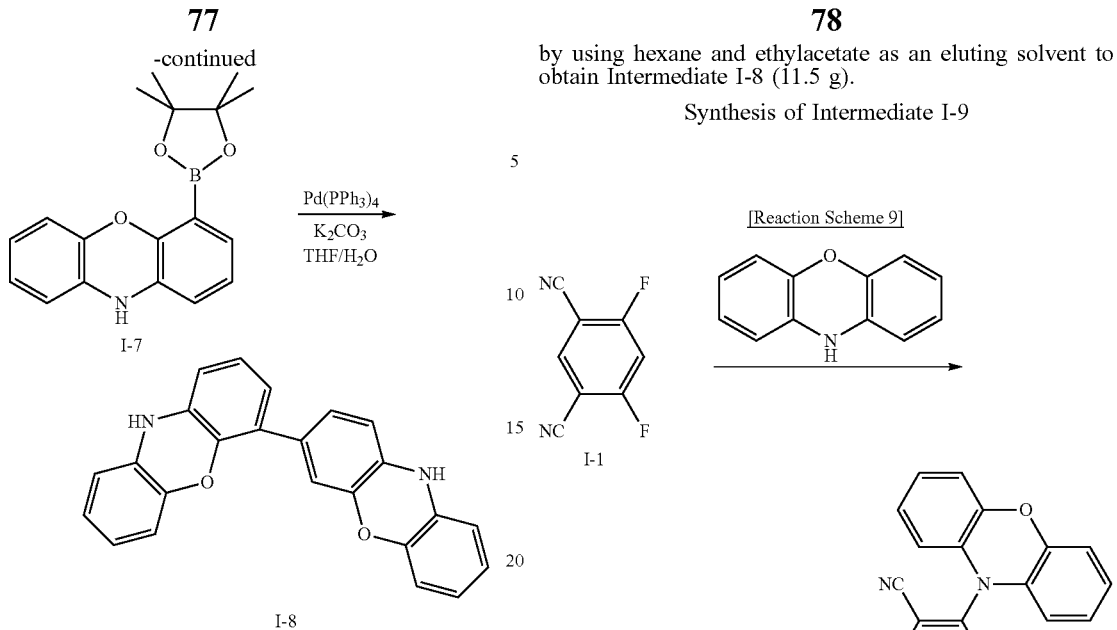

by using hexane and ethylacetate as an eluting solvent to obtain Intermediate I-8 (11.5 g).

Synthesis of Intermediate I-9

Intermediate I-6 (10 g, 38.15 mmol) was dissolved in a tetrahydrofuran solvent (100 mL) and distilled water (20 mL), Intermediate I-7 (1.1 equivalent), tetrakistriphenylphosphine palladium (0.03 equivalent), and potassium carbonate (3 equivalent) were added thereto, and the mixture was heated and refluxed for 18 hours. Subsequently, the reaction solution was cooled down to separate layers, and an organic layer was separated therefrom. Then, an aqueous layer was twice extracted with ethylacetate (50 mL), and an organic layer was collected and then, dried by adding anhydrous magnesium sulfate thereto and concentrated. The concentrated residue was purified through silica gel column Intermediate I-9 was synthesized according to the same method as the method of synthesizing Intermediate I-2 except for using phenoxazine instead of carbazole as a reactant.

Synthesis of Dopant

Synthesis Example 1: Dopant 1

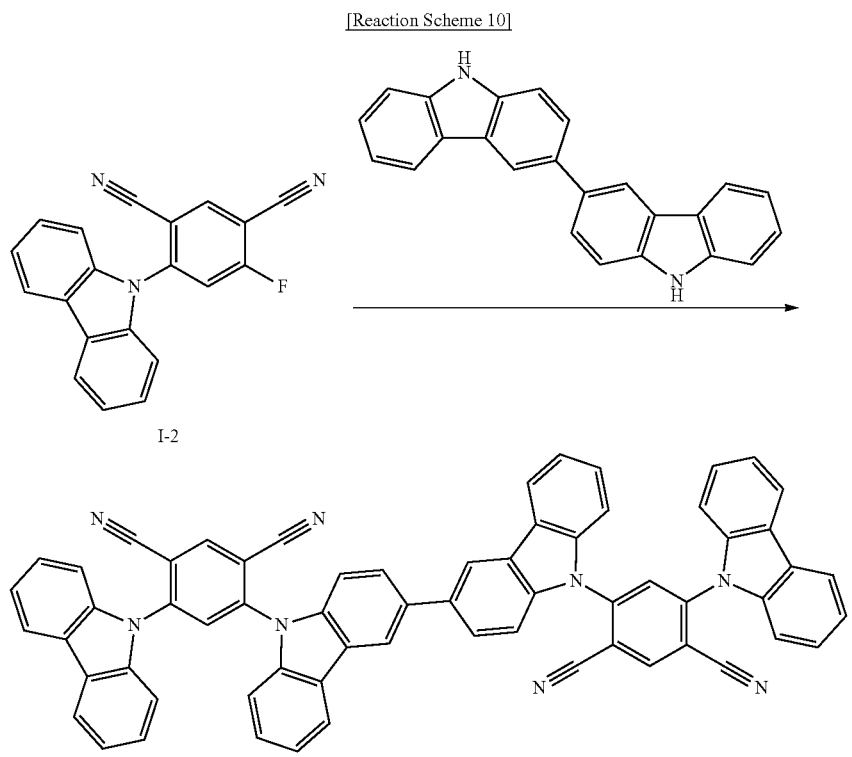

Sodium hydride (0.07 g, 1.8 mmol) was 3 times washed with hexane and then, dried under vacuum for 2 hours. Subsequently, tetrahydrofuran (20 ml) was added thereto, and after 30 minutes, 9H,9'H-3,3'-bicarbazole (0.25 g, 0.8 mmol) was added thereto. After 10 minutes, Intermediate I-2 (0.54 g, 1.7 mmol) was added thereto. Subsequently, the solution was stirred at room temperature for 10 hours, treated with magnesium sulfate by using ethylacetate to remove moisture, and then, wet-purified through a column and sublimated to obtain Dopant 1 (0.23 g). A yield was 55%.

Dopant 1: mass analysis (FAB) m/z 915 [(M+H)$^+$]. $^1$H NMR (400 MHz, CDCl$_3$): δ 8.52 (s, 2H), 8.41 (s, 2H), 8.22 (d, 2H, J=8.0 Hz), 8.14 (d, 4H, J=8.0 Hz), 8.02 (s, 2H), 7.81 (d, 2H, J=6.8 Hz), 7.54-7.38 (m, 20H).

Synthesis Example 2: Dopant 2

[Reaction Scheme 11]

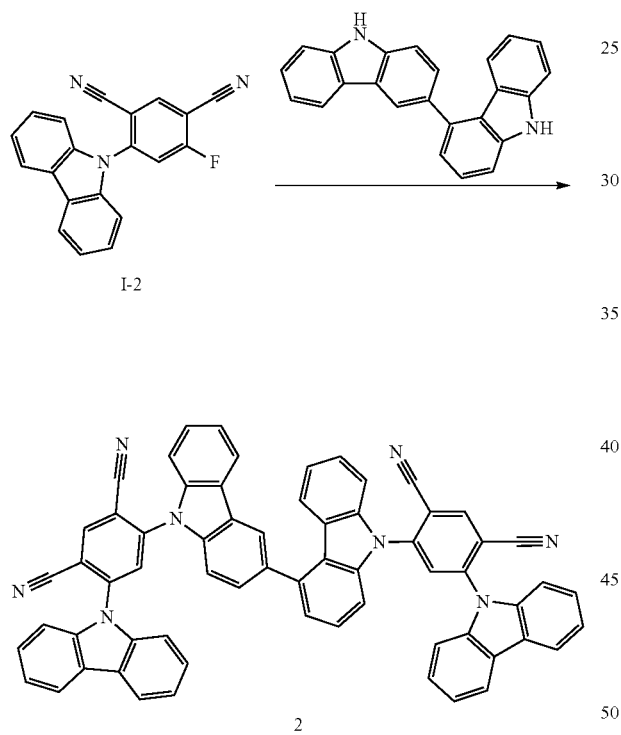

Sodium hydride (0.07 g, 1.8 mmol) was three times washed with hexane and dried under vacuum for 2 hours. Subsequently, tetrahydrofuran (20 ml) was added thereto, and after 30 minutes, 9H, 9'H-3,4'-bicarbazole (0.25 g, 0.8 mmol) was added thereto. After 10 minutes, Intermediate I-2 (0.54 g, 1.7 mmol) was added thereto. Subsequently, the solution was stirred at room temperature for 10 hours, treated with magnesium sulfate by using ethylacetate to remove moisture, and then, wet-purified through a column and sublimated to obtain Dopant 2 (0.19 g). A yield was 45%.

Dopant 2: mass analysis (FAB) m/z 915 [(M+H)$^+$]. $^1$H NMR (400 MHz, CDCl$_3$): δ 8.52 (d, 2H, J=5.2 Hz), 8.13 (d, 6H, J=7.2 Hz), 7.99 (s, 1H), 7.54-7.32 (m, 25H).

Synthesis Example 3: Dopant 3

[Reaction Scheme 12]

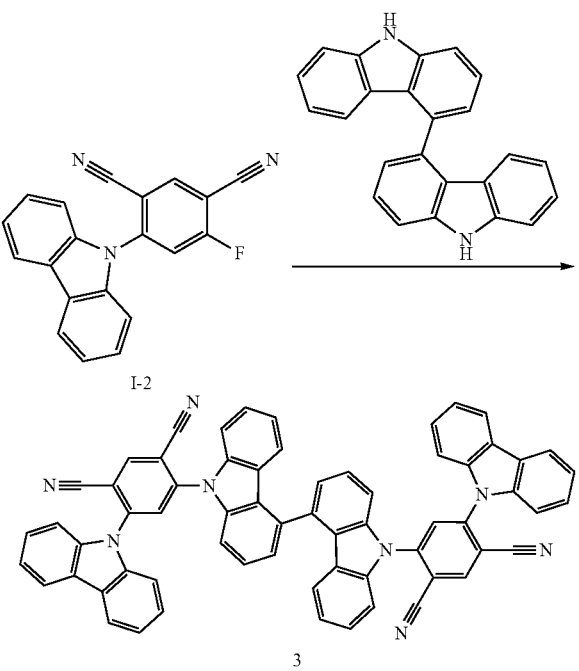

Sodium hydride (0.07 g, 1.8 mmol) was 3 times washed with hexane and dried under vacuum for 2 hours. Subsequently, tetrahydrofuran (20 ml) was added thereto, and after 30 minutes, 9H,9'H-4,4'-bicarbazole (0.25 g, 0.8 mmol) was added thereto. After 10 minutes, Intermediate I-2 (0.54 g, 1.7 mmol) was added thereto. Subsequently, the solution was stirred at room temperature for 10 hours, treated with magnesium sulfate by using ethylacetate to remove moisture, and wet-purified through a column and sublimated to obtain Dopant 3 (0.22 g). A yield was 52%.

Dopant 3: mass analysis (FAB) m/z 915 [(M+H)$^+$]. $^1$H NMR (400 MHz, CDCl$_3$): δ 8.54 (s, 2H), 8.18-8.15 (m, 4H), 8.10 (d, 1H, J=4.0 Hz), 8.05 (d, 1H, J=4.0 Hz), 7.69-7.28 (m, 22H), 7.00-6.78 (m, 4H).

Synthesis Example 4: Dopant 4

[Reaction Scheme 13]

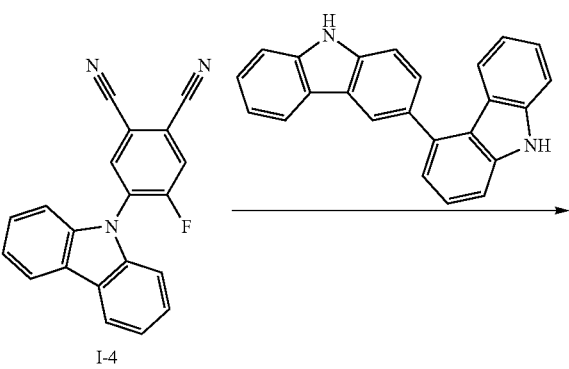

-continued

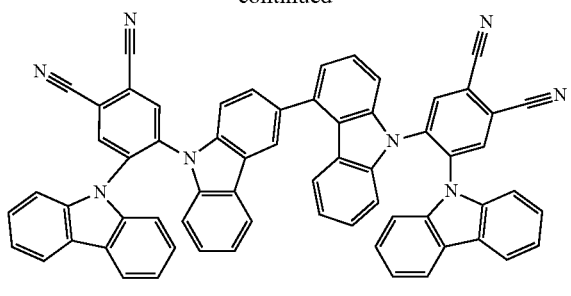

4

Sodium hydride (0.07 g, 1.8 mmol) was 3 times washed with hexane and dried under vacuum for 2 hours. Subsequently, tetrahydrofuran (20 ml) was added thereto, and after 30 minutes, 9H,9'H-3,4'-bicarbazole (0.25 g, 0.8 mmol) was added thereto. After 10 minutes, Intermediate I-4 (0.54 g, 1.7 mmol) was added thereto. Subsequently, the solution was stirred at room temperature for 10 hours, treated with magnesium sulfate by using ethylacetate to remove moisture, and then, wet-purified through a column and sublimated to obtain Dopant 4 (0.16 g). A yield was 31%.

Dopant 4: mass analysis (FAB) m/z 915 [(M+H)$^+$]. $^1$H NMR (400 MHz, CDCl$_3$): δ 8.40 (s, 1H), 8.34 (t, 3H, J=14.8 Hz), 7.83-7.72 (m, 5H), 7.24-6.89 (m, 25H).

Synthesis Example 5: Dopant 5

[Reaction Scheme 14]

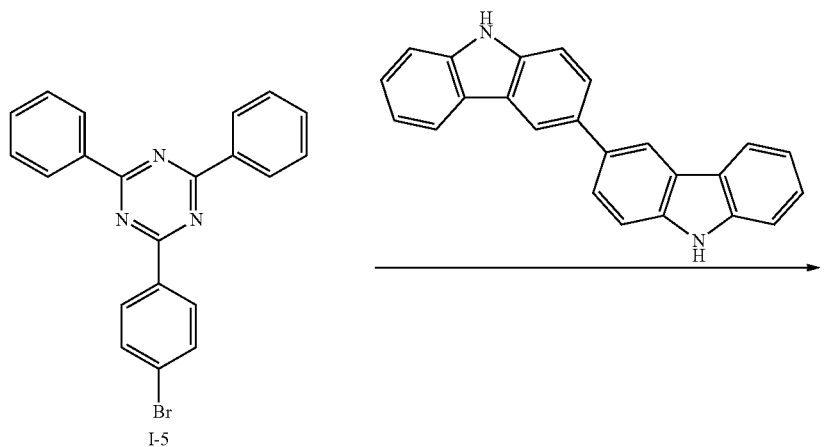

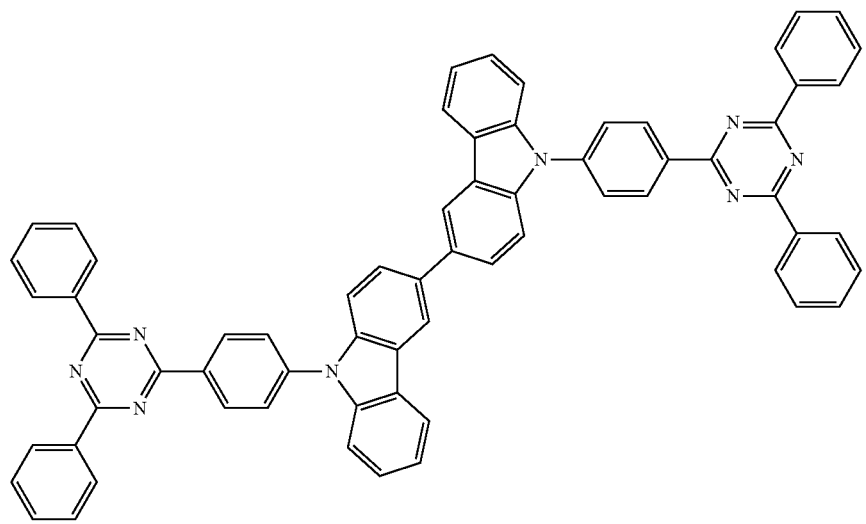

5

Intermediate I-5 (0.75 g, 1.9 mmol), 9H,9H'-3,3'-bicarbazole (0.28 g, 0.8 mmol), copper iodide (0.19 g, 1.0 mmol), and potassium phosphate (1.07 g, 5.1 mmol) were dried under vacuum for 2 hours, and 40 ml of 1,4-dioxane was added thereto. Subsequently, (±)-trans-1,2-diamino cyclohexane (0.11 g, 1.0 mmol) was added thereto, and the obtained mixture was heated up, refluxed and stirred for 12 hours, cooled down to room temperature, and filtered to obtain a precipitate. The filtered precipitate was washed with ethylacetate, dichloro methane, and hexane and then, sublimated to obtain Dopant 5 (0.6 g). A yield was 79%.

Dopant 5: mass analysis (FAB) m/z 948 [(M+H)+]. $^1$H NMR (400 MHz, CDCl$_3$): δ 9.07 (d, 4H, J=8.8 Hz), 8.84 (d, 8H, J=8.4 Hz), 8.51 (s, 2H), 8.28 (d, 2H, J=7.6 Hz), 7.90-7.84 (m, 6H), 7.69-7.60 (m, 16H), 7.49 (t, 2H, J=15.6 Hz), 7.38 (t, 2H, J=15.2 Hz).

Synthesis Example 6: Dopant 6

Intermediate I-5 (0.40 g, 1.0 mmol), 9H,9H'-3,4'-bicarbazole (0.15 g, 0.5 mmol), copper iodide (0.10 g, 0.5 mmol), and potassium phosphate (0.57 g, 2.7 mmol) were dried under vacuum for 2 hours, and 1,4-dioxane (40 ml) was added thereto. Subsequently, (±)-trans-1,2-diamino cyclohexane (0.06 g, 0.5 mmol) was added thereto, and the obtained mixture was refluxed and stirred for 12 hours, cooled down to room temperature, and filtered to obtain a precipitate. The filtered precipitate was washed by using ethylacetate, dichloro methane, and hexane and then, sublimated to obtain Dopant 6 (0.3 g). A yield was 70%.

Dopant 6: mass analysis (FAB) m/z 948 [(M+H)+]. $^1$H NMR (400 MHz, CDCl$_3$): δ 9.11-9.06 (m, 4H), 8.86-8.83 (m, 8H), 8.48 (s, 1H), 8.19 (d, 2H, J=7.6 Hz), 7.96 (d, 2H, J=8.4 Hz), 7.87 (d, 2H, J=6.8 Hz), 7.81-7.74 (m, 2H), 7.68-7.49 (m, 18H), 7.39-7.33 (m, 3H), 7.02 (t, 1H, J=14.8 Hz).

[Reaction Scheme 15]

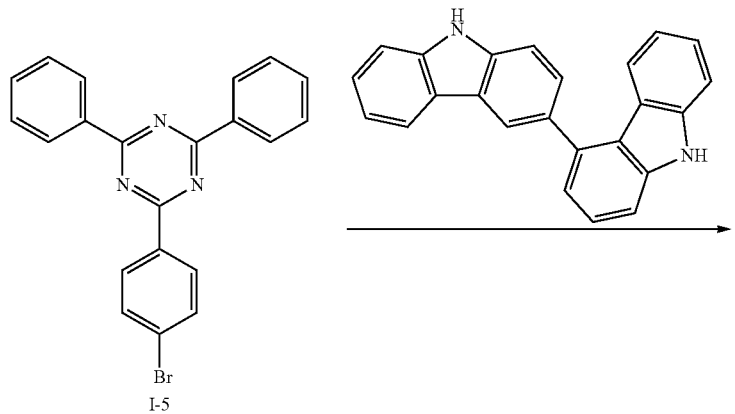

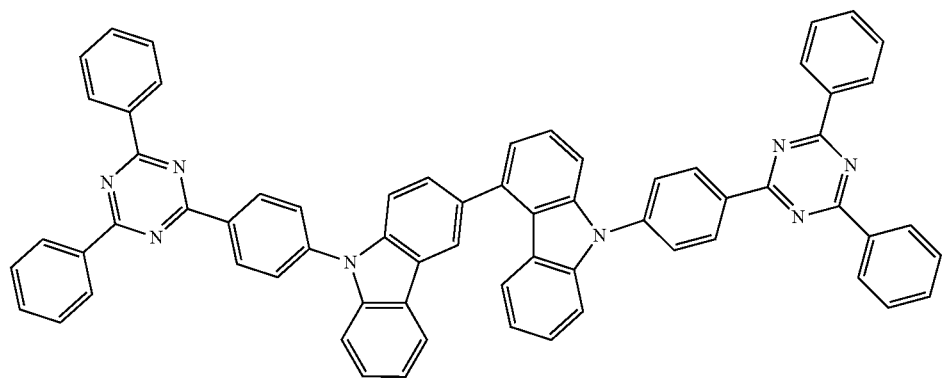

Synthesis Example 7: Dopant 7

[Reaction Scheme 16]

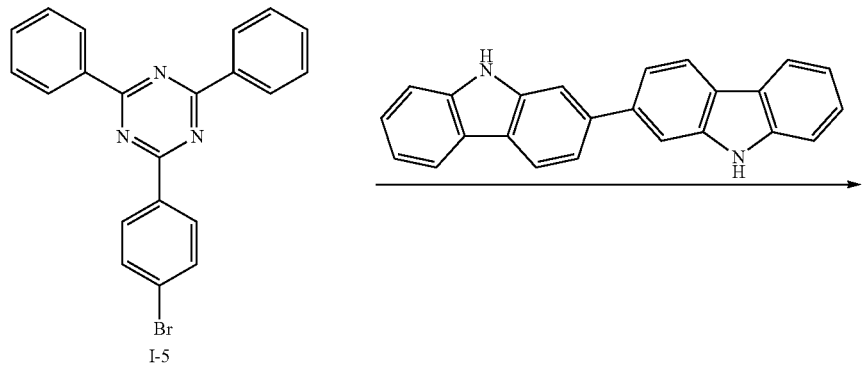

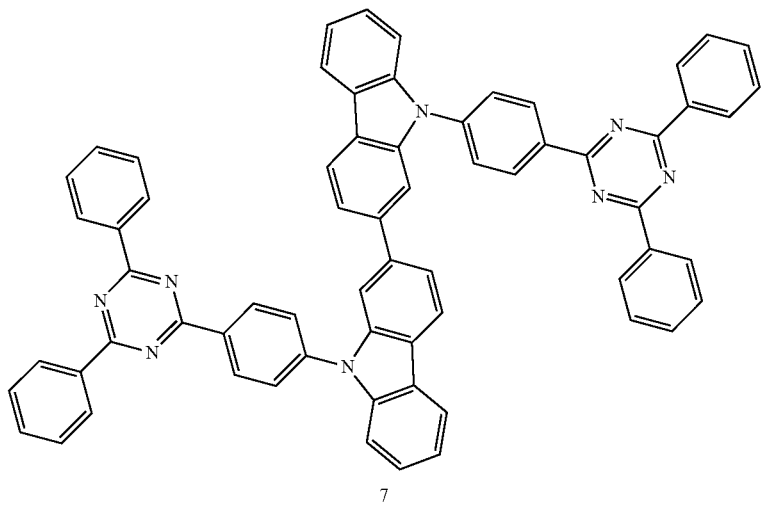

Intermediate I-5 (0.67 g, 1.7 mmol), 9H,9H'-2,2'-bicarbazole (0.25 g, 0.7 mmol), copper iodide (0.17 g, 0.9 mmol), and potassium phosphate (0.96 g, 4.5 mmol) were dried under vacuum for 2 hours, and 1,4-dioxane (40 ml) was added thereto. Subsequently, (±)-trans-1,2-diamino cyclohexane (0.10 g, 0.9 mmol) was added thereto, and the obtained mixture was heated up, refluxed and stirred for 12 hours, cooled down to room temperature, and filtered to obtain a precipitate. The filtered precipitate was washed by using ethylacetate, dichloro methane, and hexane and purified through sublimation to obtain Dopant 7 (0.2 g). A yield was 34%.

Dopant 7: mass analysis (FAB) m/z 948 [(M+H)$^+$]. $^1$H NMR (400 MHz, DMSO): δ 9.02 (d, 1H, J=8.4 Hz), 8.78 (d, 1H, J=7.2 Hz), 8.72-8.69 (m, 4H), 8.55-8.53 (m, 5H), 8.39-8.29 (m, 4H), 8.14 (d, 2H, J=8.8 Hz), 8.07-8.01 (m, 3H), 7.93-7.88 (m, 3H), 7.83-7.69 (m, 5H), 7.65-7.48 (m, 12H), 7.38-7.34 (m, 2H).

Synthesis Example 8: Dopant 8
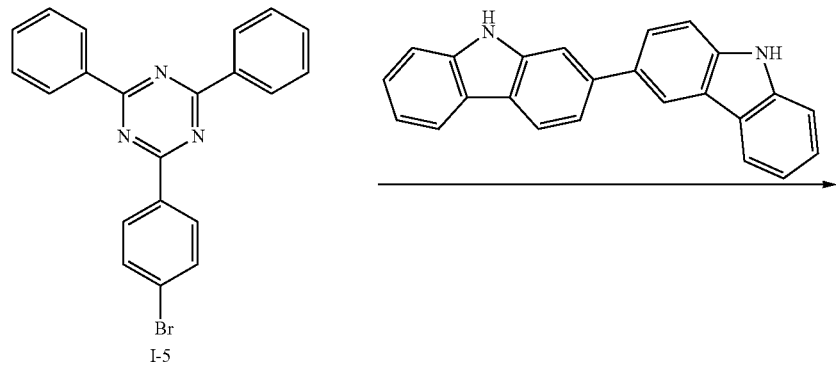
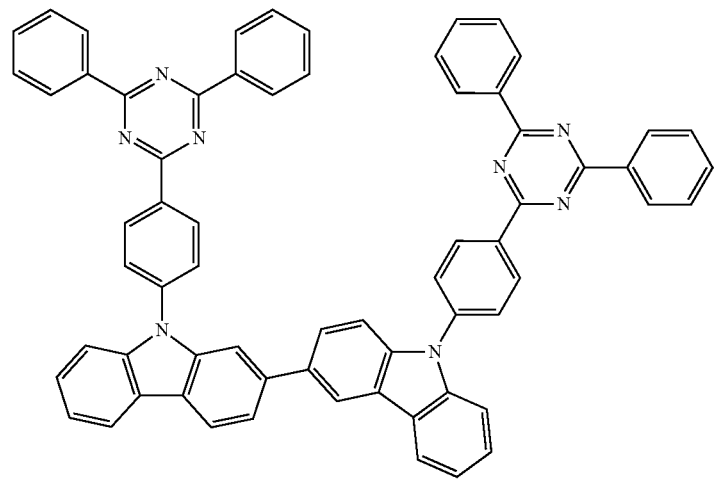
8

Intermediate I-5 (0.67 g, 1.7 mmol), 9H,9H'-2,3'-bicarbazole (0.25 g, 0.7 mmol), copper iodide (0.17 g, 0.9 mmol), and potassium phosphate (0.96 g, 4.5 mmol) were dried under vacuum for 2 hours, and 1,4-dioxane (40 ml) was added thereto. Subsequently, (±)-trans-1,2-diamino cyclohexane (0.10 g, 0.9 mmol) was added thereto, and the obtained mixture was heated up, refluxed and stirred for 12 hours, cooled down to room temperature, and filtered to collect a precipitate. The filtered precipitate was washed by using ethylacetate, dichloro methane, and hexane and then, sublimated to obtain Dopant 8 (0.48 g). A yield was 68%.

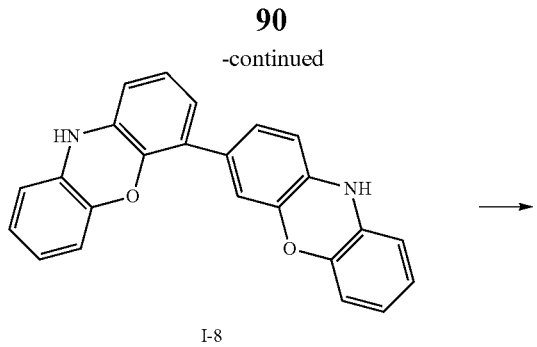

I-8

Dopant 8: mass analysis (FAB) m/z 948 [(M+H)⁺]. ¹H NMR (400 MHz, CDCl₃): δ 9.07 (d, 2H, J=8.8 Hz), 9.03 (d, 2H, J=8.0 Hz), 8.84-8.81 (m, 8H), 8.43 (s, 1H), 8.28-8.20 (m, 3H), 7.91 (d, 2H, J=8.8 Hz), 7.87-7.83 (m, 3H), 7.79-7.73 (m, 2H), 7.66-7.31 (m, 19H).

Synthesis Example 9: Dopant 44

[Reaction Scheme 18]

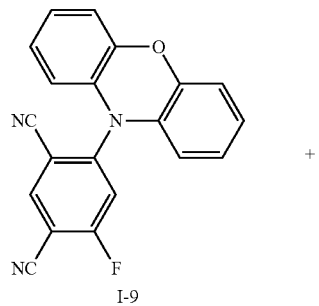

I-9

+

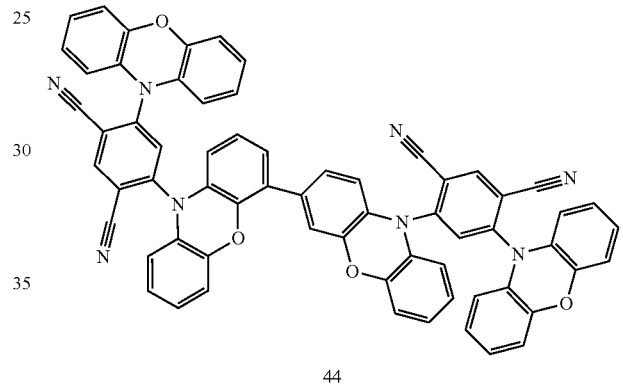

44

Intermediate I-9 and Intermediate I-8 were used to synthesize Dopant 44 in the same method as Synthesis Example 2.

Dopant 44: mass analysis (FAB) m/z 980 [(M+H)⁺]

Synthesis Example 10: Dopant 48

[Reaction Scheme 19]

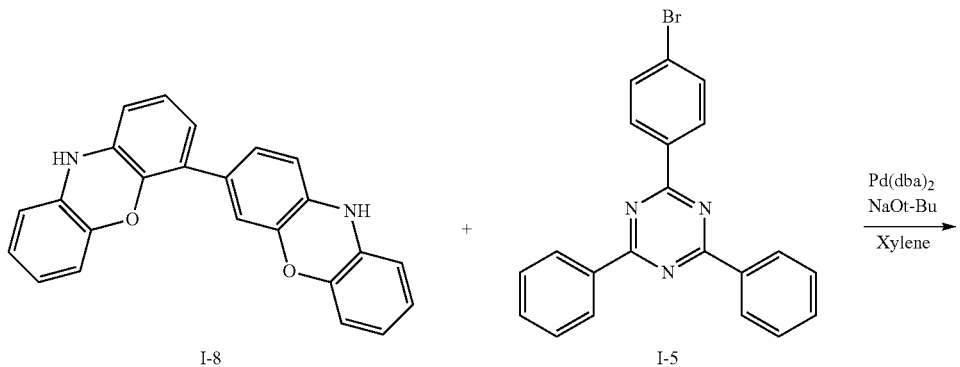

I-8

+

I-5

Pd(dba)₂
NaOt-Bu
Xylene

-continued

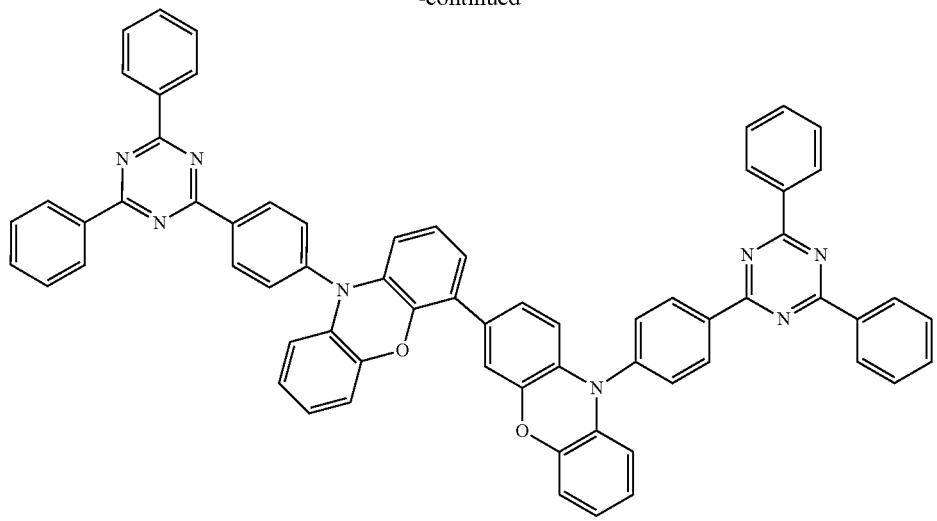

48

Intermediate I-8 and Intermediate I-5 were used to synthesize Dopant 48 in the same method as Synthesis Example 6.

Dopant 48: mass analysis (FAB) m/z 980 [(M+H)⁺]

Evaluation 1

An energy level of each dopant according to Synthesis Example 1 to 6 was evaluated.

The energy level of each dopant was measured by using an IVIUM equipment in a cyclic voltammetry method. An edge (1) of a graph obtained by coating a sample on a carbon electrode after setting a concentration at 0.1 mole by dissolving tetrabutyl ammoniumperchloride in an acetonitrile solution and changing a voltage in an order of 0 V→3 V→0 V was measured. Then, an edge (2) of another graph obtained by changing the voltage in an order of 0 V→−4→4 V→0 V was measured. HOMO energy (3) was obtained by using each measurement based on mCP as a reference value, subtracting a mCP measurement value from 6.1, and adding (1) thereto, and bandgap energy (4) was obtained by (1)+(2). LUMO energy (5) was obtained by (3)-(4). Silver (Ag) was used as a reference electrode, platinum (Pt) was used as a counter electrode, and a carbon electrode was used as a working electrode.

Singlet energy was determined from a photoluminescence (PL) spectrum of a light emitting material by dispersing the light emitting material in polystyrene, and triplet energy was determined from a first phosphorescence peak of a low temperature photoluminescence (PL) spectrum.

The results are shown in Table 1.

TABLE 1

|  | HOMO | LUMO | Energy bandgap (eV) | $S^1$ (eV) | $T^1$ (eV) |
|---|---|---|---|---|---|
| Dopant 1 | −6.38 | −3.39 | 2.99 | 2.79 | 2.71 |
| Dopant 2 | −6.30 | −3.32 | 2.98 | 2.76 | 2.68 |
| Dopant 3 | −6.11 | −3.23 | 2.88 | 2.64 | 2.54 |
| Dopant 4 | −6.22 | −3.38 | 2.84 | 2.67 | 2.65 |
| Dopant 5 | −6.01 | −3.39 | 2.94 | 2.84 | 2.58 |
| Dopant 6 | −6.25 | −3.39 | 3.06 | 2.95 | 2.64 |

Referring to Table 1, the dopants according to Synthesis Examples 1 to 6 had high singlet energy (S1) of about 2.60 to 3.00 eV, an energy bandgap of about 2.80 to 3.10 eV, and energy gap ($|S^1-T^1|$) between the singlet energy and the triplet energy in a range of about 0.01 to 0.35 eV. Accordingly, the dopants according to Synthesis Examples 1 to 6 may advantageously work for reversed intersystem crossing (RISC) of excitons into blue fluorescent light emission.

Manufacture of Organic Light Emitting Diode

Device Example 1-1

Each thin film was vacuum-deposited under a vacuum degree of 5.0×10⁻⁴ Pa on a glass substrate on which 100 nm-thick ITO is laminated. First, PEDOT:PSS (Sigma Aldrich, 60 nm), TAPC (4,4'-cyclohexylidenebis[N,N-bis(4-methylphenyl)benzenamine], EM INDEX, 10 nm), TCTA (4,4',4''-tris(carbazol-9-yl)-triphenylamine, EM INDEX, 10 nm), and mCP (1,3-bis(N-carbazolyl)benzene, EM INDEX, 10 nm) were sequentially formed on the ITO. Subsequently, a mixed host of mCP and DPEPO (bis(2-(diphenylphosphino)phenyl)ether oxide, 25 nm) and Dopant 1 obtained in Synthesis Example 1 were co-deposited to form a 25 nm-thick light emitting layer. Herein, Dopant 1 was set to be 10 wt % based on a total amount of the light emitting layer. Subsequently TSP01 (diphenyl-4-triphenylsilylphenyl-phosphine oxide, P&H Tech, 20-nm), TPBi (1,3,5-tris(1-phenyl-1H-benzimidazol-2-yl)benzene, EM INDEX, 30 nm) were sequentially formed, and then lithium fluoride (LiF, 0.8 nm) was vacuum-deposited and an aluminum (Al) cathode (100 nm) was formed to manufacture an organic light emitting diode.

Device Example 1-2

An organic light emitting diode was manufactured according to the same method as Device Example 1-1 except for using Dopant 1 in an amount of 15 wt % based on the entire amount of a light emitting layer.

Device Example 1-3

An organic light emitting diode was manufactured according to the same method as Device Example 1-1 except for using Dopant 1 in an amount of 20 wt % based on the entire amount of a light emitting layer.

Device Example 2-1

An organic light emitting diode was manufactured according to the same method as Device Example 1-1 except for using Dopant 2 obtained in Synthesis Example 2 instead of Dopant 1 in an amount of 5 wt % based on the entire amount of a light emitting layer.

Device Example 2-2

An organic light emitting diode was manufactured according to the same method as Device Example 2-1 except for using Dopant 2 in an amount of 10 wt % based on the entire amount of a light emitting layer.

Device Example 2-3

An organic light emitting diode was manufactured according to the same method as Device Example 2-1 except for using Dopant 2 in an amount of 15 wt % based on the entire amount of a light emitting layer.

Device Example 3-1

An organic light emitting diode was manufactured according to the same method as Device Example 1-1 except for using Dopant 3 obtained in Synthesis Example 3 instead of Dopant 1.

Device Example 3-2

An organic light emitting diode was manufactured according to the same method as Device Example 3-1 except for using Dopant 3 in an amount of 15 wt % based on the entire amount of a light emitting layer.

Device Example 3-3

An organic light emitting diode was manufactured according to the same method as Device Example 3-1 except for using Dopant 3 in an amount of 20 wt % based on the entire amount of a light emitting layer.

Device Example 3-4

An organic light emitting diode was manufactured according to the same method as Device Example 3-1 except for using Dopant 3 in an amount of 30 wt % based on the entire amount of a light emitting layer.

Device Example 4-1

An organic light emitting diode was manufactured according to the same method as Device Example 1-1 except for using Dopant 4 obtained in Synthesis Example 4 instead of Dopant 1.

Device Example 4-2

An organic light emitting diode was manufactured according to the same method as Device Example 4-1 except for using Dopant 4 in an amount of 15 wt % based on the entire amount of a light emitting layer.

Device Example 4-3

An organic light emitting diode was manufactured according to the same method as Device Example 4-1 except for using Dopant 4 in an amount of 16 wt % based on the entire amount of a light emitting layer.

Device Example 5-1

An organic light emitting diode was manufactured according to the same method as Device Example 1-1 except for using Dopant 5 obtained in Synthesis Example 5 instead of Dopant 1.

Device Example 5-2

An organic light emitting diode was manufactured according to the same method as Device Example 5-1 except for using Dopant 5 in an amount of 20 wt % based on the entire amount of a light emitting layer.

Device Example 5-3

An organic light emitting diode was manufactured according to the same method as Device Example 5-1 except for using Dopant 5 in an amount of 30 wt % based on the entire amount of a light emitting layer.

Evaluation 2

Color coordinate and efficiency of the organic light emitting diodes according to Device Examples 1-1 to 5-3 were evaluated.

The results are shown in Table 2 and FIGS. 3 to 7.

Figure 3:
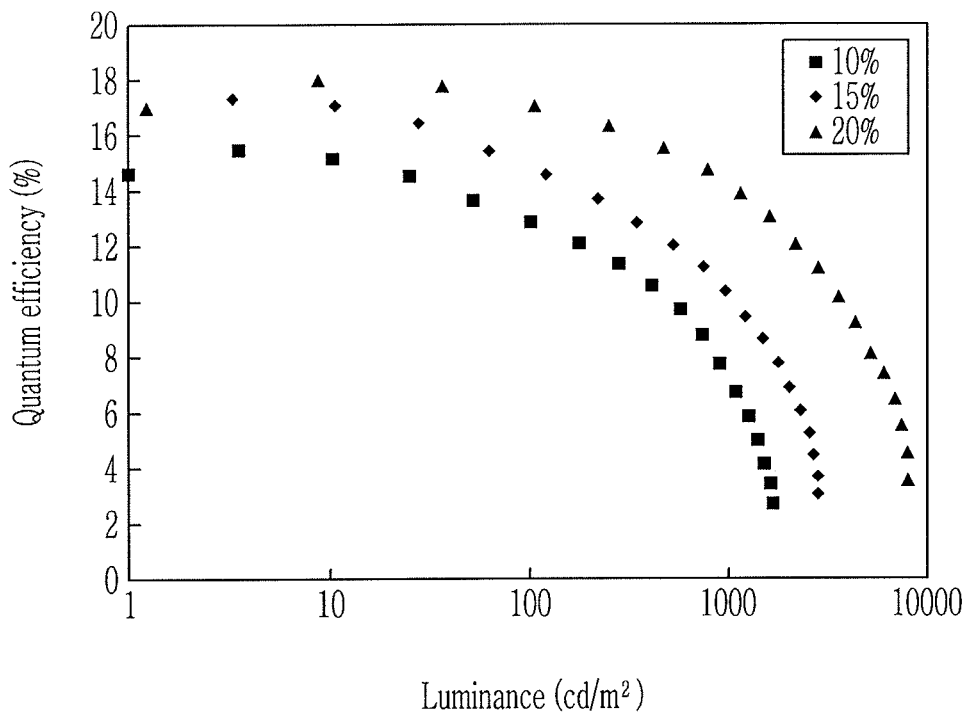
FIG. 3 is a graph showing quantum efficiency depending on luminance of the organic light emitting diodes according to Device Examples 1-1 to 1-3.
Figure 4:
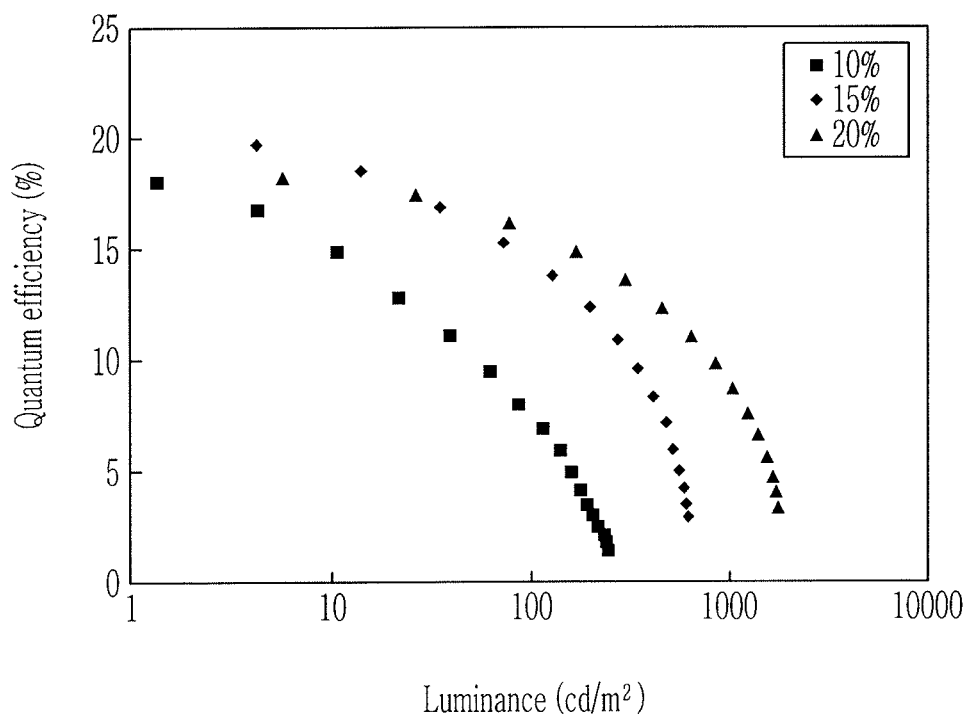
FIG. 4 is a graph showing quantum efficiency depending on luminance of the organic light emitting diodes according to Device Examples 2-1 to 2-3.
Figure 5:
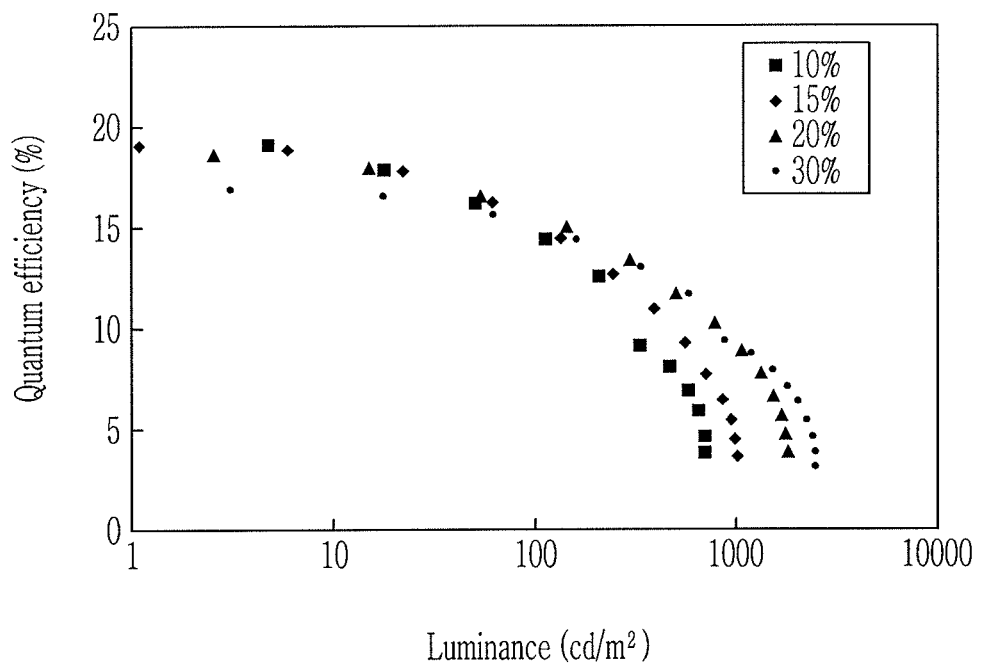
FIG. 5 is a graph showing quantum efficiency depending on luminance of the organic light emitting diodes according to Device Examples 3-1 to 3-4.
Figure 6:
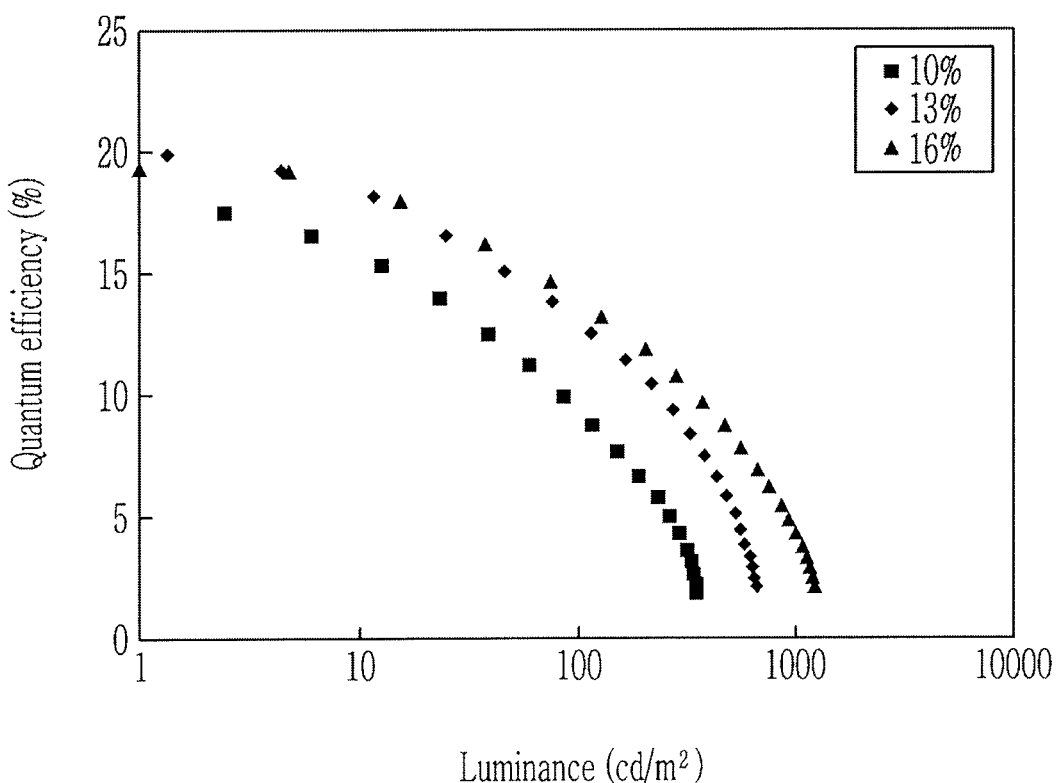
FIG. 6 is a graph showing quantum efficiency depending on luminance of the organic light emitting diodes according to Device Examples 4-1 to 4-3.
Figure 7:
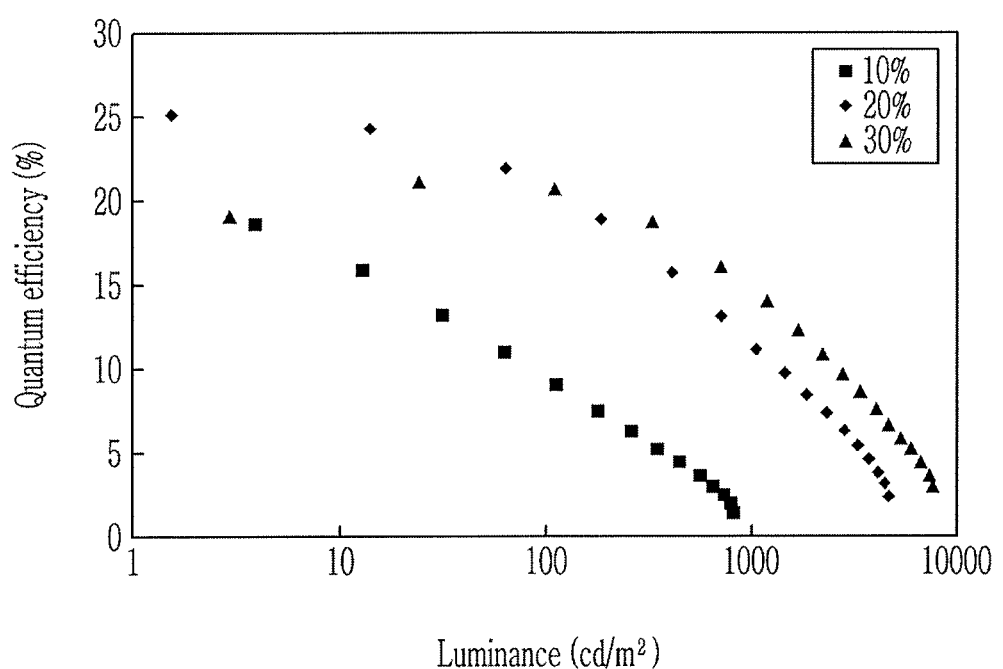
FIG. 7 is a graph showing quantum efficiency depending on luminance of the organic light emitting diodes according to Device Examples 5-1 to 5-3.

FIG. 3 is a graph showing quantum efficiency depending on luminance of the organic light emitting diodes according to Device Examples 1-1 to 1-3, FIG. 4 is a graph showing quantum efficiency depending on luminance of the organic light emitting diodes according to Device Examples 2-1 to 2-3, FIG. 5 is a graph showing quantum efficiency depending on luminance of the organic light emitting diodes according to Device Examples 3-1 to 3-4, FIG. 6 is a graph showing quantum efficiency depending on luminance of the organic light emitting diodes according to Device Examples 4-1 to 4-3, and FIG. 7 is a graph showing quantum efficiency depending on luminance of the organic light emitting diodes according to Device Examples 5-1 to 5-3.

TABLE 2

| Nos. | Color coordinate (x, y) | Maximum quantum efficiency (%) | Maximum power efficiency (lm/W) | Maximum current efficiency (cd/A) |
| --- | --- | --- | --- | --- |
| Device Example 1-1 | (0.25, 0.46) | 15.4 | 23.9 | 40.4 |
| Device Example 1-2 | (0.26, 0.48) | 17.3 | 30.6 | 47.0 |
| Device Example 1-3 | (0.29, 0.52) | 17.9 | 38.0 | 51.7 |
| Device Example 2-1 | (0.17, 0.26) | 18.4 | 18.2 | 29.0 |
| Device Example 2-2 | (0.17, 0.29) | 20.5 | 25.9 | 37.1 |
| Device Example 2-3 | (0.18, 0.31) | 18.1 | 28.8 | 37.1 |
| Device Example 3-1 | (0.16, 0.23) | 19.5 | 23.0 | 32.9 |
| Device Example 3-2 | (0.16, 0.24) | 19.0 | 23.0 | 33.0 |
| Device Example 3-3 | (0.17, 0.28) | 18.5 | 24.9 | 35.6 |
| Device Example 3-4 | (0.18, 0.31) | 17.6 | 27.7 | 35.3 |
| Device Example 4-1 | (0.21, 0.41) | 18.0 | 24.2 | 42.4 |
| Device Example 4-2 | (0.22, 0.43) | 19.8 | 31.3 | 49.2 |
| Device Example 4-3 | (0.23, 0.45) | 19.3 | 35.0 | 50.1 |
| Device Example 5-1 | (0.20, 0.33) | 20.6 | 39.1 | 45.7 |
| Device Example 5-2 | (0.23, 0.42) | 25.0 | 57.7 | 64.3 |
| Device Example 5-3 | (0.25, 0.47) | 21.1 | 46.9 | 57.3 |

Referring to Table 2 and FIGS. 3 to 7, the organic light emitting diodes according to Device Examples 1-1 to 5-3 showed sufficient efficiency characteristics.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: anode
120: cathode
130: light emitting layer
140: auxiliary layer

The invention claimed is:
1. An organic optoelectronic device, comprising:
an anode and a cathode facing each other, and a light emitting layer disposed between the anode and the cathode, the light emitting layer including:
a host, and
a dopant, the dopant being a compound of Group 1 [Grou 1'] wherein:
the host is selected from the compound having a larger energy bandgap than the dopant,
the dopant is included in an amount of 0.01 wt % to 40 wt % based on a total amount of the host and the dopant, provided that the dopant is included in a smaller amount than the host,

[Group 1]

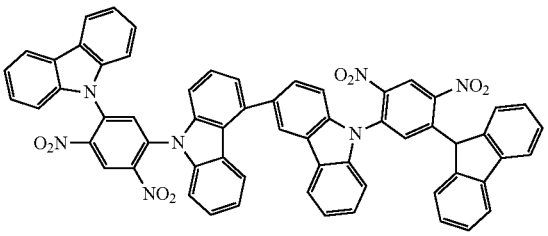

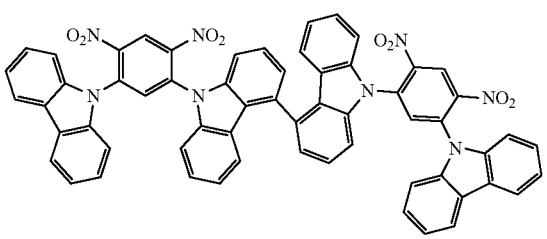

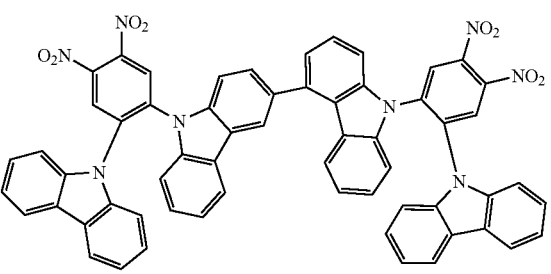

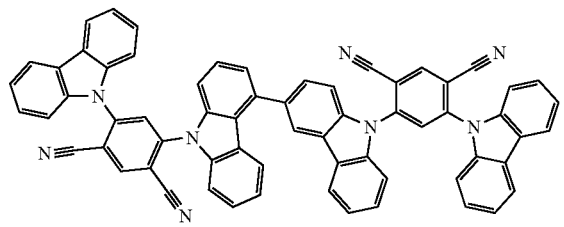

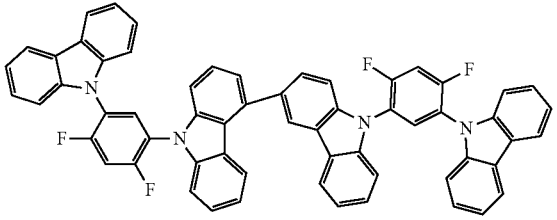

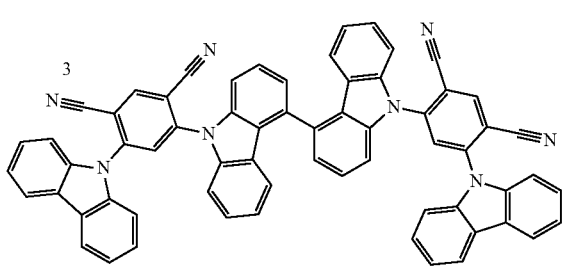

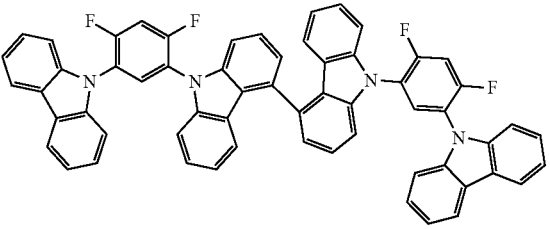

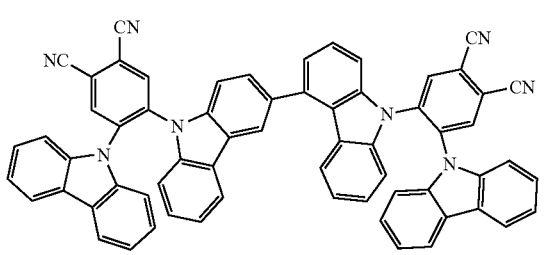

2. A display device comprising the organic optoelectronic device of claim 1.

\* \* \* \* \*